US006916777B2

(12) United States Patent
Connor et al.

(10) Patent No.: US 6,916,777 B2
(45) Date of Patent: Jul. 12, 2005

(54) FATTY ACIDS, SOAPS, SURFACTANT SYSTEMS, AND CONSUMER PRODUCTS BASED THEREON

(75) Inventors: Daniel Stedman Connor, Cincinnati, OH (US); Jeffrey John Scheibel, Loveland, OH (US); Deborah Jean Back, Cleves, OH (US); Toan Trinh, Maineville, OH (US); Phillip Kyle Vinson, Fairfield, OH (US); Roland George Severson, Cincinnati, OH (US); Thomas Anthony Cripe, Loveland, OH (US); James Charles Theophile Roger Burckett-St. Laurent, Lasne (BE); Mark Robert Sivik, Mason, OH (US); Errol Hoffman Wahl, Cincinnati, OH (US); Gayle Marie Frankenbach, Cincinnati, OH (US); Marc Johan Declercq, Strombeek-Bever (BE); Hugo Jean Marie Demeyere, Merchtem (BE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/422,744

(22) Filed: Apr. 24, 2003

(65) Prior Publication Data
US 2004/0097392 A1 May 20, 2004

Related U.S. Application Data

(62) Division of application No. 09/507,823, filed on Feb. 22, 2000, now Pat. No. 6,395,701, which is a continuation of application No. PCT/US98/22054, filed on Oct. 19, 1998.
(60) Provisional application No. 60/063,603, filed on Oct. 23, 1997.

(51) Int. Cl.[7] ............................................... C11D 9/00
(52) U.S. Cl. ..................... 510/500; 510/515; 554/52; 554/107
(58) Field of Search .................. 554/52, 107; 510/500, 510/515

(56) References Cited

U.S. PATENT DOCUMENTS

| 3,335,053 A | 8/1967 | Weitzel |
| 3,408,373 A | 10/1968 | Ault et al.. |
| 3,676,338 A | 7/1972 | Fries et al. |
| 3,926,828 A | 12/1975 | O'Neill et al. |
| T980,002 | 3/1979 | Hsieh et al. |
| 4,417,995 A | * 11/1983 | Lips et al. .................. 510/522 |
| 4,454,049 A | 6/1984 | MacGilp et al. |
| 4,808,322 A | 2/1989 | McLaughlin |
| 4,832,856 A | 5/1989 | Rutzen et al. |
| 5,223,628 A | * 6/1993 | Whittlinger .............. 548/349.1 |
| 5,232,613 A | 8/1993 | Bacon et al. |
| 5,405,542 A | 4/1995 | Trinh et al. |
| 5,476,597 A | 12/1995 | Sakata et al. |
| 5,476,649 A | 12/1995 | Naito et al. |
| 5,502,077 A | 3/1996 | Breivik et al. |
| 5,631,215 A | 5/1997 | Kinsman |
| 5,656,667 A | 8/1997 | Breivik et al. |
| 5,698,594 A | 12/1997 | Breivik et al. |
| 5,716,692 A | 2/1998 | Warner et al. |
| 5,736,503 A | 4/1998 | Vinson |
| 5,747,443 A | 5/1998 | Wahl et al. |
| 6,255,504 B1 | 7/2001 | Roberts et al. |
| 6,395,701 B1 | 5/2002 | Connor et al. |
| 6,602,845 B2 | 8/2003 | Connor et al. |

FOREIGN PATENT DOCUMENTS

| DE | 24 31 571 | 1/1976 |
| EP | 043 689 | 5/1992 |
| EP | 0 773 284 | 5/1997 |
| FR | 2351938 | 12/1977 |
| GB | 1 213 333 | 11/1970 |
| GB | 1442468 | 1/1976 |
| GB | 2237108 | 4/1991 |
| JP | 54-097609 | 8/1979 |
| JP | 63-088123 | 4/1988 |
| JP | 02-207018 | 8/1990 |
| JP | 05-48500 | 6/1993 |
| JP | 52142008 | 11/1997 |
| WO | WO 94/12608 | 6/1994 |
| WO | WO 95/35411 | 12/1995 |
| WO | WO 97/07680 | 3/1997 |
| WO | WO 97/34972 | 9/1997 |
| WO | WO 98/07679 | 2/1998 |

OTHER PUBLICATIONS

Cason, J., et al., "Branched–Chain Fatty Acids. II. Syntheses in the $C_{19}$ and $C_{25}$ Series. Preparation of Keto Esters", Journal of the American Chemical Society, vol. 66, (1944), pp. 46–50.

Juárez, P., et al. "A Microsomal Fatty acid Synthetase from the Integument of *Biattella Germanica* Synthesizes Methyl–Branched Fatty Acids, Precursors to Hydrocarbon and Contact Sex Pheromone", Archives of Biochemistry and Biophysics, vol. 293, No. 2, (Mar., 1992), pp. 333–341.

N. Nicolaides, et al., "The Saturated Methyl Branched Fatty Acids of Adult Human Skin surface Lipid", Biomedical Mass Spectrometry, vol. 4, No. 6 (1977), pp 337–347.

Ratnayake, W.M.N., "Novel Branched–Chain Fatty Acids in Certain Fish Oils", Lipids, vol. 24, No. 7 (1989), pp. 630–637.

Nicolaides, N., "The Structures of the Branched Fatty Acids in the Wax Esters of Vemix Caseosa", Lipids, vol. 6, No. 12 (Dec., 1971), pp. 901–905.

(Continued)

Primary Examiner—John R. Hardee
(74) Attorney, Agent, or Firm—Jason J. Camp; David V. Upite

(57) ABSTRACT

Novel fatty acids and derivatives thereof such as salts, new surfactant systems comprising one or more of these compounds, consumer products such as laundry products, personal care products, pharmaceutical compositions, industrial cleaners, and the like comprising said compounds or surfactant systems.

9 Claims, No Drawings

OTHER PUBLICATIONS

Kirk, Raymond E. and Donald F. Othmer, "Encyclopedia of Chemical Technology", 1$^{st}$ Edition (1951), Interscience Publishers, vol. 6, pp. 262–266.

"Fatty Acids, Their Chemistry, Properties, Production and Uses", Markley, Klare S., ed., interscience, NY (1960–1968), Part 1, pp. 48–68, 104, 112–113, 122, 170–183, 277–279, 358, 361, 411, 529–530, 542;, Part 2, p. 1348; Part 3, pp. 1758, 1774, 1791–1795, 1799–1806, 1809,1811, 1820–1821, 1838–1858, 1864–1866, 1903–1920, 1929, 1996, 2095–2096, 2212–2213; Part 4, pp. 2528–2538, 2593; Part 5, pp. 3136–3138, 3260, 3267, 3287–3299, 3421, 3458.

"Fatty Acids", Pryde, E.H., Ed., American Oil Chemists' Society (1979), pp. 2–5, 48–69.

Gunstone, F.D., "An Introduction to the Chemistry and Biochemistry of Fatty Acids and Their Glycerides", Chapman and Hall, London (1958), pp. 24–25, 46, 56–57, 183–184.

Thiel, V. et al., "Mid–chain branched alkanoic acids from "living fossil" demosponges: a link to ancient sedimentary lipids?", Organic Geochemistry, vol. 30 (1999), pp. 1–14.

* cited by examiner

FATTY ACIDS, SOAPS, SURFACTANT SYSTEMS, AND CONSUMER PRODUCTS BASED THEREON

CROSS REFERENCE

This is a divisional application of U.S. patent applicatiion Ser. No. 09/507,823, filed Feb. 22, 2000, now U.S. Pat. No. 6,395,701.

FIELD OF THE INVENTION

The present invention relates to certain novel fatty acids and derivatives thereof such as salts, to new surfactant systems comprising one or more of these compounds, and to consumer products such as laundry products, personal care products, pharmaceutical compositions, industrial cleaners, and the like comprising said compounds or surfactant systems.

BACKGROUND OF THE INVENTION

Fatty acids and soaps have a long history tracing into antiquity. The art was highly advanced at the turn of the last century (See, for example, "Modern Soaps, Candles and Glycerin", L. L. Lamborn, Van Nostrand, N.Y., 1906). Weighty tomes such as "Industrial Oil and Fat Products", A. E. Bailey, Interscience, New York, 1951 and "Fatty Acids", Ed. Klare S. Markley, Parts 1–5, Interscience, N.Y., 1960–1968 provide a systematic entry-point to the art. "Fatty Acids", Ed. E. H. Pryde, American Oil Chemists' Society, 1979, discusses fatty acids including some mention of branched types. Structures, separations and synthesis of fatty acids, including some branched examples, are laid out by F. D. Gunstone in "An Introduction to the Chemistry and Biochemistry of Fatty Acids and their Glycerides", Chapman and Hall, London, 1958. Substantial contributions to methods of synthesis of branched fatty acids were made by James Cason; see, for example, J. Amer. Chem. Soc., Vol. 66, (1944), p.46. Certain branched mixed fatty acids with high levels of impurities were known in wartime Germany, and have several disadvantages. See Bailey cited supra at pages 504–506.

Fatty acids, including branched types, can be isolated from naturally occurring materials such as vegetable, animal, fish, bird or insect oils or bacteria and can be isolated from human skin lipids. Likewise they can be made from petrochemical starting-materials.

Naturally occurring complex mixtures of esters which in principle can be hydrolyzed to fatty acid mixtures for example include those disclosed by Juarez et al, Archives of Biochemistry and Biophysics, Vol. 293, pp. 331–341 (1992); by Nicolaides et al in Biomedical Mass Spectrometry, Vol. 4., pp. 337–47 (1977); and by Ratnayake et al in Lipids, Vol. 24, pp 630–637 (1989). See also Nicolaides et al., Lipids, Vol. 6., pp. 901–905 (1971). Though such disclosures typically identify numerous monomethyl or polymethyl branched fatty acid derivatives as being present in natural systems, useful amounts of individual compounds are typically not secured.

Fatty acids and their derivatives, including certain branched types, have an enormous utility to man and have been used in applications ranging from laundry cleaning agents to anticonvulsive drugs, dermal lotions and cosmetics. See, for example, commonly assigned WO 94/12608 published Jun. 9, 1994. Such derivatives can have limitations, for example off-odors; further, it has not always been recognized which structures (e.g., primary or secondary carboxyl) are of greatest utility. Some branched fatty acids, more particularly, have been shown to have unusual properties, such as low melting points relative to equal carbon number linear analogs. In view of the age and extent of the art, improvements are becoming more difficult to achieve and what at first may appear to be small advances may carry great weight.

Commercially described branched fatty acids of varying availability include a few from Exxon, Shell, Henkel, Sasol and others; see the technical publications of these suppliers. Many of such materials contain quaternary carbon atoms. Perhaps the most common branched fatty acid type useful as a surfactant but too costly and limited in availability for high-volume applications and moreover, lacking in formulation flexibility, is isostearic acid; there are also some short-chain types, for example 2-ethylhexanoic acid, but these are relatively unuseful as surface-active agents. In short, there is a severe limitation in flexibility to the formulator when this handful of currently commercial types of branched fatty acid or mixture is relied on.

There is therefore an ongoing need for improvement in the field of branched fatty acid compositions. Accordingly, it is an object herein to provide such improvements, particularly novel fatty acids, soaps and derivatives, especially those capable of improving one or more of the following technological systems: surfactants and surfactant systems; cosurfactants; builders; antifoams; emollients and skin feel agents; particularly important is to accomplish improvements useful for the formulator of consumer products such as personal care products and laundry and cleaning products.

BACKGROUND ART

As noted, certain branched-chain fatty acids have been known for some time in the art. See, for example, "Fatty Acids (Branched-Chain)" in Kirk-Othmer's Encyclopedia of Chemical Technology, 1st. Edition, (1951), Interscience Publishers, Vol. 6, at pages 262–266, WO9807680, WO9807679 and references cited therein including, for example, several papers by Cason et al.

Known branched-chain fatty acids (for example those recognized by Chemical Abstracts by Registry numbers or those which can be found by manual searching of the older Chemical Abstracts) are nonlimitingly illustrated by: 2-, 3-, 4-, 5-, 6-, 7-, 8- and 9-methyldecanoic acid; 2-, 3-, 4-, 5-, 6-, 7-, 8-, 9- and 10-methylundecanoic acid; 2-, 3-, 4-, 5-, 6-, 7-, 8-, 9-, 10- and 11-methyldodecanoic acid; 2-, 3-, 4-, 5-, 8-, 9-, 11- and 12-methyltridecanoic acid; 2-, 3-, 4-, 5-, 6-, 7-, 8-, 9-, 10-, 11-, 12- and 13-methyltetradecanoic acid; 2-, 3-, 4-, 6-, 7-, 10-, 11-, 12-, 13- and 14-methylpentadecanoic acid; 2-, 3-, 4-, 5-, 6-, 7-, 8-, 9-, 10-, 11-, 12-, 13-, 14- and 15-methylhexadecanoic acid; 2-, 3-, 4-, 5-, 6-, 7-, 8-, 9-, 10-, 11-, 12-, 13-, 14-, 15- and 16-methylheptadecanoic acid; 2-, 3-, 4-, 5-, 6-, 7-, 8-, 9-, 10-, 11-, 12-, 13-, 14-, 15-, 16- and 17-methyloctadecanoic acid; 2-, 3-, 4-, 10-, 17- and 18-methylnonadecanoic acid.

In particular with respect to the above compounds, 11-methylpentadecanoic acid, 8-methyloctadecanoic acid and 14-methyloctadecanoic acid have been disclosed in U.S. Pat. No. 4,997,456 and commonly assigned U.S. Pat. Nos. 4,000,340 and 4,076,633 disclose 15-methyloctadecanoic acid.

Also known in the art and identified by Chemical Abstracts through registry numbers or locatable in early Chemical Abstracts are: 2,2-, 2,3-, and 2,4-dimethyldecanoic acid; 2,2-, 2,3-, 2,4-, 2,6- and 2,8-dimethylundecanoic acid; 2,2-, 2,3-, 2,4-, 2,6-, 2,8- and 2,10-dimethyldodecanoic acid; 2,4-, 2,5-, 2,6-, 2,8- and 2,10-dimethyltridecanoic acid; 2,2-, 2,3-, 2,4-, 2,6-, 2,8-, and 2,10-dimethyltetradecanoic acid, 2,4-, 2,6-, 2,10-, 2,12- and 2,14-dimethylpentadecanoic acid; 2,2-, 2,4-, 2,6-, 2,10-, 2,12- and 2,14-dimethylhexadecanoic acid; 2,2-, 2,4-, 2,5-, 2,6- and 2,10-dimethylheptadecanoic acid; 2,2-, 2,3-, 2,4- and 2,9-dimethyloctadecanoic acid; and 2,2-dimethylnonadecanoic acid.

Also known in the art and identified by Chemical Abstracts through registry numbers or locatable in early Chemical Abstracts are: 3,3-, 4,4- and 5,9-dimethyldecanoic acid; 3,3-, 3,5-, 3,7-, 3,9-, 4,8-, 9,9- and 10,10-dimethylundecanoic acid; 3,3-, 3,5-, 3,7-, 3,9-, 3,11-, 4,8- and 4,10-dimethyldodecanoic acid; 3,3-, 3,4-, 3,5-, 3,7-, 3,9-, 3,11-, 4,8-, 5,7-, 10,10- and 12,12-dimethyltridecanoic acid; 3,3-, 3,5-, 3,7-, 3,9-, 3,11-, 4,4-, 4,8-, 5,7-, 5,9-, 6,10-, 7,8-, 6,12-, 6,13-, 8,8-, 9,13- and 10,13-dimethyltetradecanoic acid; 3,3-, 3,5-, 3,6-, 3,7-, 3,9-, 3,11-, 3,13-, 4,8-, 4,10-, 5,9-, 6,8-, 6,10- and 14,14-dimethylpentadecanoic acid; 3,3-, 3,7-, 4,8-, 4,10-, 4,14-, 5,9-, 6,12-, 7,9-, 8,12-, 8,14-, 11,15- and 15,15-dimethylhexadecanoic acid; 3,3-, 5,9-, 8,10- and 12,16-dimethylheptadecanoic acid; 3,3-, 7,9-, 9,10-, 9,11- and 17,17-dimethyloctadecanoic acid; and 3,3-dimethylnonadecanoic acid. In a few cases, the acids must be extracted from natural mixtures of fatty esters.

As referred to in Kirk Othmer's article supra, other branched fatty acids known in the literature include: 2,9-dimethyloctadecanoic acid, 14-ethylhexadecanoic acid, 15-ethylheptadecanoic acid, and 12-n-hexyloctadecanoic acid. There are also numerous known examples of branched fatty acids containing quaternary carbon atoms, for example, any of the known 2,2-dimethyl substituted long-chain fatty acids specifically named hereinabove.

The known trimethyl-substituted fatty acids, having chemical abstracts registry numbers, include: 2,5,9-trimethyldecanoic acid; 2,4,5-, 2,4,6- and 2,6,10-trimethylundecanoic acid; 2,4,6-, 2,4,8-, 2,6,10- and 3,7,11-trimethyldodecanoic acid; 4,8,12-, 3,7,9-, 3,5,9-, 2,4,10-, 2,4,8-, 2,4,6-, 2,6,10- and 4,8,12-trimethyltridecanoic acid; 2,4,6-, 2,4,8-, 2,6,10-, 3,6,13-, 3,7,9-, 3,7,11- and 5,9,13-trimethyltetradecanoic acid; 2,4,6-, 2,4,8-, 3,4,7-, 3,5,9-, 3,7,9-, 3,7,11-, 3,9,11-, 3,14,14- and 6,10,14-trimethylpentadecanoic acid; 2,3,4- and 2,4,8-trimethylhexadecanoic acid; 4,8,12-trimethylheptadecanoic acid; 2,4,8-trimethyloctadecanoic acid; and 4,8,12-trimethyloctadecanoic acid.

The known polymethyl-substituted fatty acids include: 2,4,6,8-tetramethylundecanoic acid; 2,4,6,8,10-pentamethyldodecanoic acid; 3,7,9,11- and 3,5,9,11-tetramethyltridecanoic acid; 2,2,4,6,8,10-hexamethyltridecanoic acid; 3,9,11,13-, 3,7,11,13-, 3,7,9,11-, 2,4,6,10-, 3,5,11,13-, 3,5,9,11-, 2,4,8,10- and 3,3,12,12-tetramethyltetradecanoic acid; 2,6,10,14-tetramethylpentadecanoic acid; 2,6,10,14- and 3,7,11,15-tetramethylhexadecanoic acid; 4,8,12,16-tetramethyl heptadecanoic acid; 5,7,13,17-tetramethyloctadecanoic acid; and 2,2,17,17-tetramethyloctadecanoic acid.

Known monoethyl-substituted fatty acids include: 2-, 4- and 6-ethyldecanoic acid; 2-ethylundecanoic acid; 2-, 4-, 6- and 10-ethyldodecanoic acid; 2-ethyltridecanoic acid; 2-, 4- and 6-ethyltetradecanoic acid; 4- and 13-ethylpentadecanoic acid; 2-ethylhexadecanoic acid; 2- and 15-ethylheptadecanoic acid; 2-, 3-, 9-, 12- and 16-ethyloctadecanoic acid; and 2-ethylnonadecanoic acid.

Known monopropyl-substituted fatty acids include: 2-propyldecanoic acid, 2- and 3-propylundecanoic acid; 2- and 6-propyldodecanoic acid; 2-propyltridecanoic acid; 2- and 3-propyltetradecanoic acid; 2- and 3-propylpentadecanoic acid; 2-, 3- and 4-propylhexadecanoic acid; 2-propylheptadecanoic acid; and 2-propyloctadecanoic acid.

Other known substituted fatty acids include 2-ethyl-6-ethyl, 2,2-diethyl and 2-ethyl-6-methyldecanoic acid; 2-ethyl-6,8-dimethyl, 2-ethyl-4,6-dimethyl and 2-ethyl-6-methylundecanoic acid; 2-ethyl-4,6,10-trimethyl, 2-ethyl-6,10-dimethyl, 2-ethyl-6,8-dimethyl, 2-ethyl-4,6-dimethyl and 2-ethyl-6-methyldodecanoic acid; 2,8-diethyl-12-methyl, 2-ethyl-12-methyl and 2-ethyl-10-methyltridecanoic acid; 2,10-diethyl-6-methyl, 2-ethyl-6,10-dimethyl, 2-ethyl-6,8-dimethyl, and 2-ethyl-4,8-dimethyltetradecanoic acid.

Yet other substituted fatty acids known in the art include: 2,2-diethyl and 6-ethyl-2,4-dimethyldecanoic acid; 4-ethyl-5-methyl and 3-ethyl-3-methylundecanoic acid; 2,2-diethyldodecanoic acid; 3-ethyl-3-methyltridecanoic acid; 3-ethyl-3-methylpentadecanoic acid; 4,6-diethylhexadecanoic acid; 4,6-diethyl and 2-ethyl-2-propyloctadecanoic acid; and 3-ethyl-3-methylnonadecanoic acid.

In referring especially to the early literature, the following terms have been used as synonyms:

decanoic acid: capric acid
undecanoic acid: undecylic acid or hendecanoic acid
dodecanoic acid: lauric acid
tridecanoic acid: tridecoic acid
tetradecanoic acid: myristic acid
pentadecanoic acid: no early synonym
hexadecanoic acid: palmitic acid
heptadecanoic acid: margaric acid
octadecanoic acid: stearic acid
nonadecanoic acid: nonadecoic acid Additionally, with respect to substitution positions in fatty acids, the following greek letters used in the past are synonymous to the indicated numbered positions of substitution:

$\alpha=2, \beta=3, \gamma=4, \delta=5, \epsilon=6, \zeta=7, \eta=8, \theta=9, \iota=10, \kappa=11, \lambda=12, \mu=13, \nu=14, \xi=15, o=16, \pi=17, \rho 18, \sigma=19$.

Thus, for example, the modern term "2,2-dimethylheptadecanoic acid" and the older term $\alpha,\alpha$-dimethylmargaric acid" are perfectly synonymous.

SUMMARY OF THE INVENTION

The present invention encompasses improvements in consumer products, especially laundry detergents and cleaning products, made possible though innovation in fatty acids and their derivatives. Consumer products ranging from personal care products to cosmetics and paper products, into which the materials can be formulated, are encompassed.

More particularly, in one aspect, the invention encompasses a composition of matter comprising the acid, lower alkyl esters, stereoisomers, or salts of at least one branched carboxylic acid selected from the group consisting of:

(a) 2-, 3-, 4-, 5-, 6-, 7-, 8-, 9-, 10-, 12-, 13-, 14-, 15- 16-, 17- and 18-methylnonadecanoic acid; 2-, 3-, 4-, 5-, 6-, 7-, 8- and 9-methyldecanoic acid; 2-, 3-, 4-, 5-, 6-, 7-, 8-, 9- and 10-methylundecanoic acid; 2-, 3-, 4-, 5-, 6-, 7-, 8-, 9-, 10- and 11-methyldodecanoic acid; 2-, 3-, 4-, 5-, 6-, 7-, 8-, 9-, 10-, 11- and 12-methyltridecanoic acid; 2-, 3-, 4-, 5-, 6-, 7-, 8-, 9-, 10-, 11-, 12- and 13-methyltetradecanoic acid; 2-, 3-, 4-, 5-, 6-, 7-, 8-, 9-, 10-, 11-, 12-, 13- and 14-methylpentadecanoic acid; 2-, 3-, 4-, 5-, 6-, 7-, 8-, 9-, 10-, 11-, 12-, 13-, 14- and 15-methylhexadecanoic acid; 2-, 3-, 4-, 5-, 6-, 7-, 8-, 9-, 10-, 11-, 12-, 13-, 14-, 15- and 16-methylheptadecanoic acid; 2-, 3-, 4-, 5-, 6-, 7-, 8-, 9-, 10-, 11-, 12-, 13-, 14-, 15-, 16- and 17-methyloctadecanoic acid; and mixtures thereof;

(b) 2,5-, 2,7-, and 2,9-dimethyldecanoic acid; 2,5-, 2,7-, 2,9-, and 2,10-dimethylundecanoic acid; 2,5-, 2,7-, 2,9- and 2,11-dimethyldodecanoic acid; 2,3-, 2,7-, 2,9-, 2,11- and 2,12-dimethyltridecanoic acid; 2,5-, 2,7-, 2,9-, 2,11-, 2,12- and 2,13-dimethyltetradecanoic acid; 2,3-, 2,5-, 2,7-, 2,8-, 2,9-, 2,11- and 2,13-dimethylpentadecanoic acid; 2,3-, 2,5-, 2,7-, 2,8-, 2,9-, 2,11-, 2,13- and 2,15-dimethylhexadecanoic acid; 2,3-, 2,7-, 2,8-, 2,9-, 2,11-, 2,12-, 2,13-, 2,14-, 2,15- and 2,16-dimethylheptadecanoic acid; 2,5-, 2,6-, 2,7-, 2,8-, 2,10-, 2,11-, 2,12-, 2,13-, 2,14-, 2,15-, 2,16- and 2,17-dimethyloctadecanoic acid; and mixtures thereof;

(c) 3,4-, 3,5-, 3,6-, 3,8-, 3,9-, 4,5-, 4,7-, 4,9-, 5,6-, 5,7-, 5,8-, 6,7-, 6,8-, 6,9-, 7,8-, 7,9- and 8,9-, dimethyldecanoic acid; 3,4-, 3,6-, 3,8-, 3,10-, 4,5-, 4,6-, 4,7-, 4,9-, 4,10-, 5,6-, 5,7-, 5,8-, 5,9-, 5,10-, 6,7-, 6,8-, 6,9-, 6,10-, 7,8-, 7,9-, 7,10-, 8,9-, 8,10- and 9,10-, dimethylundecanoic acid; 3,4-, 3,6-, 3,8-, 3,10-, 4,5-, 4,6-, 4,7-, 4,9-, 4,11-, 5,6-, 5,7-, 5,8-, 5,9-, 5,10-, 5,11-, 6,7-, 6,8-, 6,9-, 6,10-, 6,11-, 7,8-, 7,9-, 7,10-, 7,11-, 8,9-, 8,10-, 8,11-, 9,10-, 9,11-, and 10,11-dimethyldodecanoic acid; 3,6-, 3,8-, 3,10-, 3,12-, 4,5-, 4,6-, 4,7-, 4,9-, 4,10-, 4,11-, 4,12-, 5,6-, 5,8-, 5,9-, 5,10-, 5,11-, 5,12-, 6,7-, 6,8-, 6,9-, 6,10-, 6,11-, 6,12-, 7,8-, 7,9-, 7,10-, 7,11-, 7,12-, 8,9-, 8,10-, 8,11-, 8,12-, 9,10-, 9,11-, 9,12-, 10,11-, 10,12- and 11,12-dimethyltridecanoic acid; 3,4-, 3,6-, 3,8-, 3,10-, 3,12-, 3,13-, 4,5-, 4,6-, 4,7-, 4,9-, 4,10-, 4,11-, 4,12-, 4,13-, 5,6-, 5,8-, 5,10-, 5,11-, 5,12-, 5,13-, 6,7-, 6,8-, 6,9-, 6,11-, 7,9-, 7,10-, 7,11-, 7,12-, 7,13-, 8,9-, 8,10-, 8,11-, 8,12-, 8,13-, 9,10-, 9,11-, 9,12-, 10,11-, 10,12-, 11,12-, 11,13- and 12,13-, dimethyltetradecanoic acid; 3,4-, 3,8-, 3,10-, 3,12-, 3,14-, 4,5-, 4,6-, 4,7-, 4,9-, 4,11-, 4,12-, 4,13-, 4,14-, 5,6-, 5,7-, 5,8-, 5,10-, 5,11-, 5,12-, 5,13-, 5,14-, 6,7-, 6,9-, 6,11-, 6,12-, 6,13-, 6,14-, 7,8-, 7,9-, 7,10-, 7,11-, 7,12-, 7,13-, 7,14-, 8,9-, 8,10-, 8,11-, 8,12-, 8,13-, 8,14-, 9,10-, 9,11-, 9,12-, 9,13-, 9,14-, 10,11-, 10,12-, 10,13-, 10,14-, 11,12-, 11,13-, 11,14-, 12,13-, 12,14- and 13,14-, dimethylpentadecanoic acid; 3,4-, 3,5-, 3,6-, 3,8-, 3,9-, 3,10-, 3,11-, 3,12-, 3,13-, 3,14-, 3,15-, 4,5-, 4,6-, 4,7-, 4,9-, 4,11-, 4,12-, 4,13-, 4,15-, 5,6-, 5,7-, 5,8-, 5,10-, 5,11-, 5,12-, 5,13-, 5,14-, 5,15-, 6,7-, 6,8-, 6,9-, 6,10-, 6,11-, 6,13-, 6,14-, 6,15-, 7,8-, 7,10-, 7,11-, 7,12-, 7,13-, 7,14, 7,15-, 8,9-, 8,10-, 8,11-, 8,13-, 8,15-, 9,10-, 9,11-, 9,12-, 9,13-, 9,14-, 9,15-, 10,11-, 10,12-, 10,13-, 10,14-, 10,15-, 11,12-, 11,13-, 11,14-, 12,13-, 12,14-, 12,15-, 13,14-, 13,15- and 14,15-, dimethylhexadecanoic acid; 3,4-, 3,5-, 3,6-, 3,7-, 3,8-, 3,9-, 3,10-, 3,11-, 3,12-, 3,13-, 3,14-, 3,15-, 3,16-, 4,5-, 4,6-, 4,7-, 4,8-, 4,9-, 4,10-, 4,11-, 4,12-, 4,13-, 4,14-, 4,15-, 4,16-, 5,6-, 5,7-, 5,8-, 5,10-, 5,11-, 5,12-, 5,13-, 5,14-, 5,15-, 5,16-, 6,7-, 6,8-, 6,9-, 6,10-, 6,11-, 6,12-, 6,13-, 6,14-, 6,15-, 6,16-, 7,8-, 7,9-, 7,10-, 7,11-, 7,12-, 7,13-, 7,14-, 7,15-, 7,16-, 8,9-, 8,11-, 8,12-, 8,13-, 8,14-, 8,15-, 8,16-, 9,10-, 9,11-, 9,12-, 9,13-, 9,14-, 9,15-, 9,16-, 10,11-, 10,12-, 10,13-, 10,14-, 10,15-, 10,16-, 11,12-, 11,13-, 11,14-, 11,15-, 11,16-, 12,13-, 12,14-, 12,15-, 13,14-, 13,15-, 13,16-, 14,15-, 14,16- and 15,16-, dimethylheptadecanoic acid; 3,4-, 3,5-, 3,6-, 3,7-, 3,8-, 3,9-, 3,10-, 3,11-, 3,12-, 3,13-, 3,14-, 3,15-, 3,16-, 3,17-, 4,5-, 4,6-, 4,7-, 4,8-, 4,9-, 4,10-, 4,11-, 4,12-, 4,13-, 4,14-, 4,15-, 4,16-, 4,17-, 5,6-, 5,7-, 5,8-, 5,9-, 5,10-, 5,11-, 5,12-, 5,13-, 5,14-, 5,15-, 5,16-, 5,17-, 6,7-, 6,8-, 6,9-, 6,10-, 6,11-, 6,12-, 6,13-, 6,14-, 6,15-, 6,16-, 6,17-, 7,8-, 7,10-, 7,11-, 7,12-, 7,13-, 7,14-, 7,15-, 7,16-, 7,17-, 8,9-, 8,10-, 8,11-, 8,12-, 8,13-, 8,14-, 8,15-, 8,16-, 8,17-, 9,12-, 9,13-, 9,14-, 9,15-, 9,16-, 9,17-, 10,11-, 10,12-, 10,13-, 10,14-, 10,15-, 10,16-, 10,17-, 11,12-, 11,13-, 11,14-, 11,15-, 11,16-, 11,17-, 12,13-, 12,14-, 12,15-, 12,16-, 12,17-, 13,14-, 13,15-, 13,16-, 13,17-, 14,15-, 14,16-, 14,17-, 15,16-, 15,17- and 16,17-dimethyloctadecanoic acid; and mixtures thereof;

(d) 3-, 4-, 5-, 6-, 7- and 8-methyl-2-ethylnonanoic acid; 3-, 4-, 5-, 7-, 8- and 9-methyl-2-ethyldecanoic acid; 3-, 4-, 5-, 7-, 8-, 9- and 10-methyl-2-ethylundecanoic acid; 3-, 4-, 5-, 7-, 8-, 9-, 10- and 11-, methyl-2-ethyldodecanoic acid; 3-, 4-, 5-, 6-, 7-, 8-, 9- and 11-methyl-2-ethyltridecanoic acid; 3-, 4-, 5-, 6-, 7-, 8-, 9-, 10-, 11-, 12- and 13-methyl-2-ethyltetradecanoic acid; 3-, 4-, 5-, 6-, 7-, 8-, 9-, 10-, 11-, 12-, 13- and 14-methyl-2-ethylpentadecanoic acid; 3-, 4-, 5-, 6-, 7-, 8-, 9-, 10-, 11-, 12-, 13-, 14- and 15-methyl-2-ethylhexadecanoic acid; 3-, 4-, 5-, 6-, 7-, 8-, 9-, 10-, 11-, 12-, 13-, 14-, 15- and 16-methyl-2-ethylheptadecanoic acid; and mixtures thereof;

(e) 3-, 5-, 6-, 7- and 8-ethyldecanoic acid; 3-, 4-, 5-, 6-, 7-, 8- and 9-ethylundecanoic acid; 3-, 5-, 7-, 8- and 9-ethyldodecanoic acid; 3-, 4-, 5-, 6-, 7-, 8-, 9-, 10- and 11-ethyltridecanoic acid; 3-, 5-, 7-, 8-, 9-, 10-, 11- and 12-ethyltetradecanoic acid; 2-, 3-, 5-, 6-, 7-, 8-, 9-, 10-, 11- and 12-ethylpentadecanoic acid; 3-, 4-, 5-, 6-, 7-, 8-, 9-, 10-, 11-, 12-, 13- and 14-ethylhexadecanoic acid; 3-, 4-, 5-, 6-, 7-, 8-, 9-, 10-, 11-, 12-, 13- and 14-ethylheptadecanoic acid; 4-, 5-, 6-, 7-, 8-, 10-, 11-, 13-, 14- and 15-ethyloctadecanoic acid; and mixtures thereof;

(f) 3-, 4-, 5-, 6- and 7-propyldecanoic acid; 4-, 5-, 6-, 7- and 8-propylundecanoic acid; 3-, 4-, 5-, 7-, 8- and 9-propyldodecanoic acid; 3-, 4-, 5-, 6-, 7-, 8-, 9- and 10-propyltridecanoic acid; 4-, 5-, 6-, 7-, 8-, 9-, 10- and 11-propyltetradecanoic acid; 4-, 5-, 6-, 7-, 8-, 9-, 10-, 11- and 12-propylpentadecanoic acid; 5-, 6-, 7-, 8-, 9-, 10-, 11-, 12- and 13-propylhexadecanoic acid; 3-, 4-, 5-, 6-, 7-, 8-, 9-, 10-, 11-, 12-, 13- and 14-propylheptadecanoic acid; and mixtures thereof;

(g) 3,4-, 3,5-, 3,6-, 3,7-, 4,5-, 4,6-, 4,7-, 5,6-, 5,7- and 6,7-dimethyl-2-ethyloctanoic acid; 3,4-, 3,5-, 3,6-, 3,7-, 3,8-, 4,5-, 4,6-, 4,7-, 4,8-, 5,6-, 5,7-, 5,8-, 6,7-, 6,8- and 7,8-, dimethyl-2-ethylnonanoic acid; 3,4-, 3,5-, 3,6-, 3,7-, 3,8-, 3,9-, 4,5-, 4,6-, 4,7-, 4,8-, 4,9-, 5,6-, 5,7-, 5,8-, 5,9-, 6,7-, 6,8-, 6,9-, 7,8-, 7,9- and 8,9-dimethyl-2-ethyldecanoic acid; 3,4-, 3,5-, 3,6-, 3,7-, 3,8-, 3,9-, 3,10-, 4,5-, 4,7-, 4,8-, 4,9-, 4,10-, 5,6-, 5,7-, 5,8-, 5,9-, 5,10-, 6,7-, 6,9-, 6,10-, 7,8-, 7,9-, 7,10-, 8,9-, 8,10- and 9,10-, dimethyl-2-ethylundecanoic acid; 3,4-, 3,5-, 3,6-, 3,7-, 3,8-, 3,9-, 3,10-, 3,11-, 4,5-, 4,7-, 4,8-, 4,9-, 4,10-, 4,11-, 5,6-, 5,7-, 5,8-, 5,9-, 5,10-, 5,11-, 6,7-, 6,9-, 6,11-, 7,8-, 7,9-, 7,10-, 7,11-, 8,9-, 8,10-, 8,11-, 9,10-, 9,11- and 10,11-dimethyl-2-ethyldodecanoic acid; 3,4-, 3,5-, 3,6-, 3,7-, 3,8-, 3,9-, 3,10-, 3,11-, 3,12-, 4,5-, 4,6-, 4,7-, 4,8-, 4,9-, 4,10-, 4,11-, 4,12-, 5,6-, 5,7-, 5,8-, 5,9-, 5,10-, 5,11-, 5,12-, 6,7-, 6,8-, 6,9-, 6,10-, 6,11-, 6,12-, 7,8-, 7,9-, 7,10-, 7,11-, 7,12-, 8,9-, 8,10-, 8,11-, 8,12-, 9,10-, 9,11-, 9,12-, 10,11-, 10,12- and 11,12-dimethyl-2-ethyltridecanoic acid; 3,4-, 3,5-, 3,6-, 3,7-, 3,8-, 3,9-, 3,10-, 3,11-, 3,12-, 3,13-, 4,5-, 4,6-, 4,7-, 4,9-, 4,10-, 4,11-, 4,12-, 4,13-, 5,6-, 5,7-, 5,8-, 5,9-, 5,10-, 5,11-, 5,12-, 5,13-, 6,7-, 6,9-, 6,11-, 6,12-, 6,13-, 7,8-, 7,9-, 7,10-, 7,11-, 7,12-, 7,13-, 8,9-, 8,10-, 8,11-, 8,12-, 8,13-, 9,10-, 9,11-, 9,12-, 9,13-, 10,11-, 10,12-, 10,13-, 11,12-, 11,13- and 12,13-dimethyl-2-ethyltetradecanoic acid; 3,4-, 3,5-, 3,6-, 3,7-, 3,8-, 3,9-, 3,10-, 3,11-, 3,12-, 3,13-, 3,14-, 4,5-, 4,6-, 4,7-, 4,8-, 4,9-, 4,10-, 4,11-, 4,12-, 4,13-, 4,14-, 5,6-, 5,7-, 5,8-, 5,9-, 5,10-, 5,11-, 5,12-, 5,13-, 5,14-, 6,7-, 6,8-, 6,9-, 6,10-, 6,11-, 6,12-, 6,13-, 6,14-, 7,8-, 7,9-, 7,10-, 7,11-, 7,12-, 7,13-, 7,14-, 8,9-, 8,10-, 8,11-, 8,12-, 8,13-, 8,14-, 9,10-, 9,11-, 9,12-, 9,13-, 9,14-, 10,11-, 10,12-, 10,13-, 10,14-, 11,12-, 11,13-, 11,14-, 12,13-, 12,14- and 13,14-dimethyl-2-ethylpentadecanoic acid; 3,4-, 3,5-, 3,6-, 3,7-, 3,8-, 3,9-, 3,10-, 3,11-, 3,12-, 3,13-, 3,14-, 3,15-, 4,5-, 4,6-, 4,7-, 4,8-, 4,9-, 4,10-, 4,11-, 4,12-, 4,13-, 4,14-, 4,15-, 5,6-, 5,7-, 5,8-, 5,9-, 5,10-, 5,11-, 5,12-, 5,13-, 5,14-, 5,15-, 6,7-, 6,8-, 6,9-, 6,10-, 6,11-, 6,12-, 6,13-, 6,14-, 6,15-, 7,8-, 7,9-, 7,10-, 7,11-, 7,12-, 7,13-, 7,14-, 7,15-, 8,9-, 8,10-, 8,11-, 8,12-, 8,13-, 8,14-, 8,15-, 9,10-, 9,11-, 9,12-, 9,13-, 9,14-, 9,15-, 10,11-, 10,12-, 10,13-, 10,14-, 10,15-, 11,12-, 11,13-, 11,14-, 11,15-, 12,13-, 12,14-, 12,15-, 13,14-, 13,15- and 14,15-dimethyl-2-ethylhexadecanoic acid; and mixtures thereof;

(h) 3-, 4-, 5- and 6-, methyl-2-propylheptanoic acid; 3-, 4-, 5-, 6- and 7-methyl-2-propyloctanoic acid; 3-, 4-, 5-, 6-, 7- and 8-methyl-2-propylnonanoic acid; 3-, 4-, 5-, 6-, 7-, 8- and 9-methyl-2-propyldecanoic acid; 3-, 4-, 5-, 6-, 7-, 8-, 9 and 10-methyl-2-propylundecanoic acid; 3-, 4-, 5-, 6-, 7-, 8-, 9-, 10- and 11-methyl-2-propyldodecanoic acid; 3-, 4-, 5-, 6-, 7-, 8-, 9-, 10-, 11- and 12-methyl-2-propyltridecanoic acid; 3-, 4-, 5-, 6-, 7-, 8-, 9-, 10-, 11-, 12- and 13-methyl-2-propyltetradecanoic acid; 3-, 4-, 5-, 6-, 7-, 8-, 9-, 10-, 11-, 12-, 13- and 14-methyl-2-propylpentadecanoic acid; and mixtures thereof;

(i) 2,3,4-, 2,3,5-, 2,3,6-, 2,3,7-, 2,3,8-, 2,3,9-, 2,3,10-, 2,3,11-, 2,3,12-, 2,3,13-, 2,3,14-, 2,3,15-, 2,3,16-, 2,4,5-, 2,4,6-, 2,4,7-, 2,4,8-, 2,4,9-, 2,4,10-, 2,4,11-, 2,4,12-, 2,4,13-, 2,4,14-, 2,4,15-, 2,4,16-, 2,5,6-, 2,5,7-, 2,5,8-, 2,5,9-, 2,5,10-, 2,5,11-, 2,5,12-, 2,5,13-, 2,5,14-, 2,5,15-, 2,5,16-, 2,6,7-, 2,6,8-, 2,6,9-, 2,6,10-, 2,6,11-, 2,6,12-, 2,6,13-, 2,6,14-, 2,6,15-, 2,6,16-, 2,7,8-, 2,7,9-, 2,7,10-, 2,7,11-, 2,7,12-, 2,7,13-, 2,7,14-, 2,7,15-, 2,7,16-, 2,8,9-, 2,8,10-, 2,8,11-, 2,8,12-, 2,8,13-, 2,8,14-, 2,8,15-, 2,8,16-, 2,9,10-, 2,9,11-, 2,9,12-, 2,9,13-, 2,9,14-, 2,9,15-, 2,9,16-, 2,10,11-, 2,10,12-, 2,10,13-, 2,10,14-, 2,10,15-, 2,10,16-, 2,11,12-, 2,11,13-, 2,11,14-, 2,11,15-, 2,11,16-, 2,12,13-, 2,12,14-, 2,12,15-, 2,12,16-, 2,13,14-, 2,13,15-, 2,13,16-, 2,14,15-, 2,14,16-, 2,15,16-, 3,4,5-, 3,4,6-, 3,4,7-, 3,4,8-, 3,4,9-, 3,4,10-, 3,4,11-, 3,4,12-, 3,4,13-, 3,4,14-, 3,4,15-, 3,4,16-, 3,5,6-, 3,5,7-, 3,5,8-, 3,5,9-, 3,5,10-, 3,5,11-, 3,5,12-, 3,5,13-, 3,5,14-, 3,5,15-, 3,5,16-, 3,6,7-, 3,6,8-, 3,6,9-, 3,6,10-, 3,6,11-, 3,6,12-, 3,6,13-, 3,6,14-, 3,6,15-, 3,6,16-, 3,7,8-, 3,7,9-, 3,7,10-, 3,7,11-, 3,7,12-, 3,7,13-, 3,7,14-, 3,7,15-, 3,7,16-, 3,8,9-, 3,8,10-, 3,8,11-, 3,8,12-, 3,8,13-, 3,8,15-, 3,8,14-, 3,8,16-, 3,9,10-, 3,9,11-, 3,9,12-, 3,9,13-, 3,9,14-, 3,9,15-, 3,9,16-, 3,10,11-, 3,10,12-, 3,10,13-, 3,10,14-, 3,10,15-, 3,10,16-, 3,11,12-, 3,11,14-, 3,11,13-, 3,11,15-, 3,11,16-, 3,12,13-, 3,12,14-, 3,12,15-, 3,12,16-, 3,13,14-, 3,13,15-, 3,13,16-, 3,14,15-, 3,14,16-, 3,15,16-, 4,5,6-, 4,5,7-, 4,5,8-, 4,5,9-, 4,5,10-, 4,5,11-, 4,5,12-, 4,5,13-, 4,5,14-, 4,5,15-, 4,5,16-, 4,6,7-, 4,6,8-, 4,6,9-, 4,6,10-, 4,6,11-, 4,6,12-, 4,6,13-, 4,6,14-, 4,6,15-, 4,6,16-, 4,7,8-, 4,7,9-, 4,7,10-, 4,7,11-, 4,7,12-, 4,7,13-, 4,7,14-, 4,7,15-, 4,7,16-, 4,8,9-, 4,8,10-, 4,8,11-, 4,8,13-, 4,8,14-, 4,8,15-, 4,8,16-, 4,9,10-, 4,9,11-, 4,9,12-, 4,9,13-, 4,9,14-, 4,9,15-, 4,9,16-, 4,10,11-, 4,10,12-, 4,10,13-, 4,10,14-, 4,10,15-, 4,10,16-, 4,11,12-, 4,11,13-, 4,11,14-, 4,11,15-, 4,11,16-, 4,12,13, 4,12,14-, 4,12,15-, 4,12,16-, 4,13,14-, 4,13,15-, 4,13,16-, 4,14,15-, 4,14,16-, 4,15,16-, 5,6,7-, 5,6,8-, 5,6,9-, 5,6,10-, 5,6,11-, 5,6,12-, 5,6,13-, 5,6,14-, 5,6,15-, 5,6,16-, 5,7,8-, 5,7,9-, 5,7,10-, 5,7,11-, 5,7,12-, 5,7,13-, 5,7,14-, 5,7,15-, 5,7,16-, 5,8,9-, 5,8,10-, 5,8,11-, 5,8,12-, 5,8,13-, 5,8,14-, 5,8,15-, 5,8,16-, 5,9,10-, 5,9,11-, 5,9,12-, 5,9,13-, 5,9,14-, 5,9,15-, 5,9,16-, 5,10,11-, 5,10,12-, 5,10,13-, 5,10,14-, 5,10,15-, 5,10,16-, 5,11,12-, 5,11,13-, 5,11,14-, 5,11,15-, 5,12,13-, 5,12,14-, 5,12,15-, 5,12,16-, 5,13,14-, 5,13,15-, 5,13,16-, 5,14,15-, 5,14,16-, 5,15,16-, 6,7,8-, 6,7,9-, 6,7,10-, 6,7,11-, 6,7,12-, 6,7,13-, 6,7,14-, 6,7,15-, 6,7,16-, 6,8,9-, 6,8,10-, 6,8,11-, 6,8,12-, 6,8,13-, 6,8,14-, 6,8,15-, 6,8,16-, 6,9,10-, 6,9,11-, 6,9,12-, 6,9,13-, 6,9,14-, 6,9,15-, 6,9,16-, 6,10,11-, 6,10,12-, 6,10,13-, 6,10,14-, 6,10,15-, 6,10,16-, 6,11,12-, 6,11,13-, 6,11,14-, 6,11,15-, 6,11,16-, 6,12,13-, 6,12,14-, 6,12,15-, 6,12,16-, 6,13,14-, 6,13,15-, 6,13,16-, 6,14,15-, 6,14,16-, 6,15,16-, 7,8,9-, 7,8,10-, 7,8,11-, 7,8,12-, 7,8,13-, 7,8,14-, 7,8,15-, 7,8,16-, 7,9,10-, 7,9,11-, 7,9,12-, 7,9,13-, 7,9,14-, 7,9,15-, 7,9,16-, 7,10,11-, 7,10,12-, 7,10,13-, 7,10,14-, 7,10,15-, 7,10,16-, 7,11,12-, 7,11,13-, 7,11,14-, 7,11,15-, 7,11,16-, 7,12,13-, 7,12,14-, 7,12,15-, 7,12,16-, 7,13,14-, 7,13,15-, 7,13,16-, 7,14,15-, 7,14,16-, 7,15,16-, 8,9,10-, 8,9,11-, 8,9,12-, 8,9,13-, 8,9,14-, 8,9,15-, 8,9,16-, 8,10,11-, 8,10,12-, 8,10,13-, 8,10,14-, 8,10,15-, 8,10,16-, 8,11,12-, 8,11,13-, 8,11,14-, 8,11,15-, 8,11,16-, 8,12,13-, 8,12,14-, 8,12,15-, 8,12,16-, 8,13,14-, 8,13,15-, 8,13,16-, 8,14,15-, 8,14,16-, 8,15,16-, 9,10,11-, 9,10,12-, 9,10,13-, 9,10,14-, 9,10,15-, 9,10,16-, 9,11,12-, 9,11,13-, 9,11,14-, 9,11,15-, 9,11,16-, 9,12,13-, 9,12,14-, 9,12,15-, 9,12,16-, 9,13,14-, 9,13,15-, 9,13,16-, 9,14,15-, 9,14,16-, 9,15,16-, 10,11,12-, 10,11,13-, 10,11,14-, 10,11,15-, 10,11,16-, 10,12,13-, 10,12,14-, 10,12,15-, 10,12,16-, 10,13,14-, 10,13,15-, 10,13,16-, 10,14,15-, 10,14,16-, 10,15,16-, 11,12,13-, 11,12,14-, 11,12,15-, 11,12,16-, 11,13,14-, 11,13,15-, 11,13,16-, 11,14,15-, 11,14,16-, 11,15,16-, 12,13,14-, 12,13,15-, 12,13,16-, 12,14,15-, 12,14,16-, 12,15,16-, 13,14,15-13,14,16-, 13,15,16- and 14,15,16-trimethylheptadecanoic acid; 2,3,5-, 2,3,6-, 2,3,7-, 2,3,8-, 2,3,9-, 2,3,10-, 2,3,11-, 2,3,12-, 2,3,13-, 2,3,14-, 2,3,15-, 2,4,5-, 2,4,6-, 2,4,7-, 2,4,9-, 2,4,10-, 2,4,11-, 2,4,12-, 2,4,13-, 2,4,14-, 2,4,15-, 2,5,6-, 2,5,7-, 2,5,8-, 2,5,9-, 2,5,10-, 2,5,11-, 2,5,12-, 2,5,13-, 2,5,14-, 2,5,15-, 2,6,7-, 2,6,8-, 2,6,9-, 2,6,10-, 2,6,11-, 2,6,12-, 2,6,13-, 2,6,14-, 2,6,15-, 2,7,8-, 2,7,9-, 2,7,10-, 2,7,11-, 2,7,12-, 2,7,13-, 2,7,14-, 2,7,15-, 2,8,9-, 2,8,10-, 2,8,11-, 2,8,12-, 2,8,13-, 2,8,14-, 2,8,15-, 2,9,10-, 2,9,11-, 2,9,12-, 2,9,13-, 2,9,14-, 2,9,15-, 2,10,11-, 2,10,12-, 2,10,13-, 2,10,14-, 2,10,15-, 2,11,12-, 2,11,13-, 2,11,14-, 2,11,15-, 2,12,13-, 2,12,14-, 2,12,15-, 2,13,14-, 2,13,15-, 2,14,15-, 3,4,5-, 3,4,6-, 3,4,7-, 3,4,8-, 3,4,9-, 3,4,10-, 3,4,11-, 3,4,12-, 3,4,13-, 3,4,14-, 3,4,15-, 3,5,6-, 3,5,7-, 3,5,8-, 3,5,9-, 3,5,10-, 3,5,11-, 3,5,12-, 3,5,13-, 3,5,14-, 3,5,15-, 3,6,7-, 3,6,8-, 3,6,9-, 3,6,10-, 3,6,11-, 3,6,12-, 3,6,13-, 3,6,14-, 3,6,15-, 3,7,8-, 3,7,9-, 3,7,10-, 3,7,11-, 3,7,12-, 3,7,13-, 3,7,14-, 3,7,15-, 3,8,9-, 3,8,10-, 3,8,11-, 3,8,12-, 3,8,13-, 3,8,14-, 3,8,15-, 3,9,10-, 3,9,11-, 3,9,12-, 3,9,13-, 3,10,11-, 3,10,12-, 3,10,13-, 3,10,14-, 3,10,15-, 3,11,12-, 3,11,13-, 3,11,14-, 3,11,15-, 3,12,13-, 3,12,14-, 3,12,15-, 3,13,14-, 3,13,15-, 3,14,15-, 4,5,6-, 4,5,7-, 4,5,8-, 4,5,9-, 4,5,10-, 4,5,11-, 4,5,12-, 4,5,13-, 4,5,14-, 4,5,15-, 4,6,7-, 4,6,8-, 4,6,9-, 4,6,10-, 4,6,11-, 4,6,12-, 4,6,13-, 4,6,14-, 4,6,15-, 4,7,8-, 4,7,9-, 4,7,10-, 4,7,11-, 4,7,12-, 4,7,13-, 4,7,14-, 4,7,15-, 4,8,9-, 4,8,10-, 4,8,11-, 4,8,12-, 4,8,13-, 4,8,14-, 4,8,15-, 4,9,10-, 4,9,11-, 4,9,12-, 4,9,13-, 4,9,14-, 4,9,15-, 4,10,11-, 4,10,12-, 4,10,13-, 4,10,14-, 4,10,15-, 4,11,12-, 4,11,13-, 4,11,14-, 4,11,15-, 4,12,13-, 4,12,14-, 4,12,15-, 4,13,14-, 4,13,15-, 4,14,15-, 5,6,7-, 5,6,8-, 5,6,9-, 5,6,10-, 5,6,11-, 5,6,12-, 5,6,13-, 5,6,14-, 5,6,15-, 5,7,8-, 5,7,9-, 5,7,10-, 5,7,11-, 5,7,12-, 5,7,13-, 5,7,14-, 5,7,15-, 5,8,9-5,8,10-, 5,8,11-, 5,8,12-, 5,8,13-, 5,8,14-, 5,8,15-, 5,9,10-, 5,9,11-5,9,12-, 5,9,13-, 5,9,14-, 5,9,15-, 5,10,11-, 5,10,12-, 5,10,13-, 5,10,14-, 5,10,15-, 5,11,12-, 5,11,13-, 5,11,14-, 5,11,15-, 5,12,13-, 5,12,14-, 5,12,15-, 5,13,14-, 5,13,15-, 5,14,15-, 6,7,8-, 6,7,9-, 6,7,10-, 6,7,11-, 6,7,12-, 6,7,13-, 6,7,14-, 6,7,15-, 6,8,9-6,8,10-, 6,8,11-, 6,8,12-, 6,8,13-, 6,8,14-, 6,8,15-, 6,9,10-, 6,9,11-, 6,9,12-, 6,9,13-, 6,9,14-, 6,9,15-, 6,10,11-, 6,10,12-, 6,10,13-, 6,10,14-, 6,10,15-, 6,11,12-, 6,11,13-, 6,11,14-, 6,11,15-, 6,12,13-, 6,12,14-, 6,12,15-, 6,13,14-, 6,13,15-, 6,14,15-, 7,8,9-, 7,8,10-, 7,8,11-, 7,8,12-, 7,8,13-, 7,8,14-, 7,8,15-, 7,9,10-, 7,9,11-, 7,9,12-, 7,9,13-, 7,9,14-, 7,9,15-, 7,10,11-, 7,10,12-, 7,10,13-, 7,10,14-, 7,10,15-, 7,11,12-, 7,11,13-, 7,11,14-, 7,11,15-, 7,12,13-, 7,12,14-, 7,12,15-, 7,13,14-, 7,13,15-, 7,14,15-, 8,9,10-, 8,9,11-, 8,9,12-, 8,9,13-, 8,9,14-, 8,9,15-, 8,10,11-, 8,10,12-, 8,10,13-, 8,10,14-, 8,10,15-, 8,11,12-, 8,11,13-, 8,11,14-, 8,11,15-, 8,12,13-, 8,12,14-, 8,12,15-, 8,13,14-, 8,13,15-, 8,14,15-, 9,10,11-, 9,10,12-, 9,10,13-, 9,10,14-, 9,10,15-, 9,11,12-, 9,11,13-, 9,11,14-, 9,11,15-, 9,12,13-, 9,12,14-, 9,12,15-, 9,13,14-, 9,13,15-, 9,14,15-, 10,11,12-, 10,11,13-, 10,11,14-, 10,11,15-, 10,12,13-, 10,12,14-, 10,12,15-, 10,13,14-, 10,13,15-, 10,14,15-, 11,12,13-, 11,12,14-, 11,12,15-, 11,13,14-, 11,13,15-, 11,14,15-, 12,13,14-, 12,13,15-, 12,14,15- and 4,15-trimethylhexadecanoic acid; 2,3,4-, 2,3,5-, 2,3,6-, 2,3,7-, 2,3,8-, 2,3,9-, 2,3,10-, 2,3,11-, 2,3,12-, 2,3,13-, 2,3,14-, 2,4,5-, 2,4,7-, 2,4,9-, 2,4,10-, 2,4,11-, 2,4,12-, 2,4,13-, 2,4,14-, 2,5,6-, 2,5,7-, 2,5,8-, 2,5,9-, 2,5,10-, 2,5,11-, 2,5,12-, 2,5,13-, 2,5,14-, 2,6,7-, 2,6,8-, 2,6,9-, 2,6,10-, 2,6,11-, 2,6,12-, 2,6,13-, 2,6,14-, 2,7,8-, 2,7,9-, 2,7,10-, 2,7,11-, 2,7,12-, 2,7,13-, 2,7,14-, 2,8,9-, 2,8,10-, 2,8,11-, 2,8,12-, 2,8,13-, 2,8,14-, 2,9,10-, 2,9,11-, 2,9,12-, 2,9,13-, 2,9,14-, 2,10,11-, 2,10,12-, 2,10,13-, 2,10,14-, 2,11,12-, 2,11,13-, 2,11,14-, 2,12,13-, 2,12,14-, 2,13,14-, 3,4,5-, 3,4,6-, 3,4,7-, 3,4,8-, 3,4,9-, 3,4,10-, 3,4,11-, 3,4,12-, 3,4,13-, 3,4,14-, 3,5,6-, 3,5,7-, 3,5,8-, 3,5,10-, 3,5,11-, 3,5,12-, 3,5,13-, 3,5,14-, 3,6,7-, 3,6,8-, 3,6,9-, 3,6,10-, 3,6,11-, 3,6,12-, 3,6,13-, 3,6,14-, 3,7,8-, 3,7,10-, 3,7,12-, 3,7,13-, 3,7,14-, 3,8,9-, 3,8,10-, 3,8,11-, 3,8,12-, 3,8,13-, 3,8,14-, 3,9,10-, 3,9,12-, 3,9,13-, 3,9,14-, 3,10,11-, 3,10,12-, 3,10,13-, 3,10,14-, 3,11,12-, 3,11,13-, 3,11,14-, 3,12,13-, 3,12,14-, 3,13,14-, 4,5,6-, 4,5,7-, 4,5,8-, 4,5,9-, 4,5,10-, 4,5,11-, 4,5,12-, 4,5,13-, 4,5,14-, 4,6,7-, 4,6,8-, 4,6,9-, 4,6,10-, 4,6,11-, 4,6,12-, 4,6,13-, 4,6,14-, 4,7,8-, 4,7,9-, 4,7,10-, 4,7,11-, 4,7,12-, 4,7,13-, 4,7,14-, 4,8,9-, 4,8,10-, 4,8,11-, 4,8,12-, 4,8,13-, 4,8,14-, 4,9,10-, 4,9,11-, 4,9,12-, 4,9,13-, 4,9,14-, 4,10,11-, 4,10,12-, 4,10,13-, 4,10,14-, 4,11,12-, 4,11,13-, 4,11,14-, 4,12,13-, 4,12,14-, 4,13,14-, 5,6,7-, 5,6,8-, 5,6,9-, 5,6,10-, 5,6,11-, 5,6,12-, 5,6,13-, 5,6,14-, 5,7,8-, 5,7,9-, 5,7,10-, 5,7,11-, 5,7,12-, 5,7,13-, 5,7,14-, 5,8,9-, 5,8,10-, 5,8,11-, 5,8,12-, 5,8,13-, 5,8,14-, 5,9,10-, 5,9,11-, 5,9,12-, 5,9,13-, 5,9,14-, 5,10,11-, 5,10,12-, 5,10,13-, 5,10,14-, 5,11,12-, 5,11,13-, 5,11,14-, 5,12,13-, 5,12,14-, 5,13,14-, 6,7,8-, 6,7,9-, 6,7,10-, 6,7,11-, 6,7,12-, 6,7,13-, 6,7,14-, 6,8,9-, 6,8,10-, 6,8,11-, 6,8,12-, 6,8,13-, 6,8,14-, 6,9,10-, 6,9,11-, 6,9,12-, 6,9,13-, 6,9,14-, 6,10,11-, 6,10,12-, 6,10,13-, 6,11,12-, 6,11,13-, 6,11,14-, 6,12,13-, 6,12,14-, 6,13,14-, 7,8,9-, 7,8,10-, 7,8,11-, 7,8,12-, 7,8,13-, 7,8,14-, 7,9,10-, 7,9,11-, 7,9,12-, 7,9,13-, 7,9,14-, 7,10,11-, 7,10,12-, 7,10,13-, 7,10,14-, 7,11,12-, 7,11,13-, 7,11,14-, 7,12,13-, 7,12,14-, 7,13,14-, 8,9,10-, 8,9,11-, 8,9,12-, 8,9,13-, 8,9,14-, 8,10,11-, 8,10,12-, 8,10,13-, 8,10,14-, 8,11,12-, 8,11,13-, 8,11,14-, 8,12,13-, 8,12,14-, 8,13,14-, 9,10,11-, 9,10,12-, 9,10,13-, 9,10,14-, 9,11,12-, 9,11,13-, 9,11,14-, 9,12,13-, 9,12,14-, 9,13,14-, 10,11,12-, 10,11,13-, 10,11,14-, 10,12,13-, 10,12,14-, 10,13,14-, 11,12,13-, 11,12,14-, 11,13,14- and 12,13,14-trimethylpentadecanoic acid; 2,3,4-, 2,3,5-, 2,3,6-, 2,3,7-, 2,3,8-, 2,3,9-, 2,3,10-, 2,3,11-, 2,3,12-, 2,3,13-, 2,4,5-, 2,4,7-, 2,4,9-, 2,4,10-, 2,4,11-, 2,4,12-, 2,4,13-, 2,5,6-, 2,5,7-, 2,5,8-, 2,5,9-, 2,5,10-, 2,5,11-, 2,5,12-, 2,5,13-, 2,6,7-, 2,6,8-, 2,6,9-, 2,6,11-, 2,6,12-, 2,6,13-, 2,7,8-, 2,7,9-, 2,7,10-, 2,7,11-, 2,7,12-, 2,7,13-, 2,8,9-, 2,8,10-, 2,8,11-, 2,8,12-, 2,8,13-, 2,9,10-, 2,9,11-, 2,9,12-, 2,9,13-, 2,10,11-, 2,10,12-, 2,10,13-, 2,11,12-, 2,11,13-, 2,12,13-, 3,4,5-, 3,4,6-, 3,4,7-, 3,4,8-, 3,4,9-, 3,4,10-, 3,4,11-, 3,4,12-, 3,4,13-, 3,5,6-, 3,5,7-, 3,5,8-, 3,5,9-, 3,5,10-, 3,5,11-, 3,5,12-, 3,5,13-, 3,6,7-, 3,6,8-, 3,6,9-, 3,6,10-, 3,6,11-, 3,6,12-, 3,7,8-, 3,7,10-, 3,7,11-, 3,7,12-, 3,7,13-, 3,8,9-, 3,8,10-, 3,8,11-, 3,8,12-, 3,8,13-, 3,9,10-, 3,9,11-, 3,9,12-, 3,9,13-, 3,10,11-, 3,10,12-, 3,10,13-, 3,11,12-, 3,11,13-, 3,12,13-, 4,5,6-, 4,5,7-, 4,5,8-, 4,5,9-, 4,5,10-, 4,5,11-, 4,5,12-, 4,5,13-, 4,6,7-, 4,6,8-, 4,6,9-, 4,6,10-, 4,6,11-, 4,6,12-, 4,6,13-, 4,7,8-, 4,7,9-, 4,7,10-, 4,7,11-, 4,7,12-, 4,7,13-, 4,8,9-, 4,8,10-, 4,8,11-, 4,8,12-, 4,8,13-, 4,9,10-, 4,9,11-, 4,9,12-, 4,9,13-, 4,10,11-, 4,10,12-, 4,10,13-, 4,11,12-, 4,11,13-, 4,12,13-, 5,6,7-, 5,6,8-, 5,6,9-, 5,6,10-, 5,6,11-, 5,6,12-, 5,6,13-, 5,7,8-, 5,7,9-, 5,7,10-, 5,7,11-, 5,7,12-, 5,7,13-, 5,8,9-, 5,8,10-, 5,8,11-, 5,8,12-, 5,8,13-, 5,9,10-, 5,9,11-, 5,9,12-, 5,9,13-, 5,10,11-, 5,10,12-, 5,10,13-, 5,11,12-, 5,11,13-, 5,12,13-, 6,7,8-, 6,7,9-, 6,7,10-, 6,7,11-, 6,7,12-, 6,7,13-, 6,8,9-, 6,8,10-, 6,8,11-, 6,8,12-, 6,8,13-, 6,9,10-, 6,9,11-, 6,9,12-, 6,9,13-, 6,10,11-, 6,10,12-, 6,10,13-, 6,11,12-, 6,11,13-, 6,12,13-, 7,8,9-, 7,8,10-, 7,8,11-, 7,8,12-, 7,8,13-, 7,9,10-, 7,9,11-, 7,9,12-, 7,9,13-, 7,10,11-, 7,10,12-, 7,10,13-, 7,11,12-, 7,11,13-, 7,12,13-, 8,9,10-, 8,9,11-, 8,9,12-, 8,9,13-, 8,10,11-, 8,10,12-, 8,10,13-, 8,11,12-, 8,11,13-, 8,12,13-, 9,10,11-, 9,10,12-, 9,10,13-, 9,11,12-, 9,11,13-, 9,12,13-, 10,11,12-, 10,11,13-, 10,12,13- and 11,12,13-trimethyltetradecanoic acid; 2,3,4-, 2,3,5-, 2,3,6-, 2,3,7-, 2,3,8-, 2,3,9-, 2,3,10-, 2,3,11-, 2,3,12-, 2,4,5-, 2,4,7-, 2,4,9-, 2,4,11-, 2,4,12-, 2,5,6-, 2,5,7-, 2,5,8-, 2,5,9-, 2,5,10-, 2,5,11-, 2,5,12-, 2,6,7-, 2,6,8-, 2,6,9-, 2,6,11-, 2,6,12-, 2,7,8-, 2,7,9-, 2,7,10-, 2,7,11-, 2,7,12-, 2,8,9-, 2,8,10-, 2,8,11-, 2,8,12-, 2,9,10-, 2,9,11-, 2,9,12-, 2,10,11-, 2,10,12-, 2,11,12-, 3,4,5-, 3,4,6-, 3,4,7-, 3,4,8-, 3,4,9-, 3,4,10-, 3,4,11-, 3,4,12-, 3,5,6-, 3,5,7-, 3,5,8-, 3,5,10-, 3,5,11-, 3,5,12-, 3,6,7-, 3,6,8-, 3,6,9-, 3,6,10-, 3,6,11-, 3,6,12-, 3,7,8-, 3,7,10-, 3,7,11-, 3,7,12-, 3,8,9-, 3,8,10-, 3,8,11-, 3,8,12-, 3,9,10-, 3,9,11-, 3,9,12-, 3,10,11-, 3,10,12-, 3,11,12-, 4,5,6-, 4,5,7-, 4,5,8-, 4,5,9-, 4,5,10-, 4,5,11-, 4,5,12-, 4,6,7-, 4,6,8-, 4,6,9-, 4,6,10-, 4,6,11-, 4,6,12-, 4,7,8-, 4,7,9-, 4,7,10-, 4,7,11-, 4,7,12-, 4,8,9-, 4,8,10-, 4,8,11-, 4,9,10-, 4,9,11-, 4,9,12-, 4,10,11-, 4,10,12-, 4,11,12-, 5,6,7-, 5,6,8-, 5,6,9-, 5,6,10-, 5,6,11-, 5,6,12-, 5,7,8-, 5,7,9-, 5,7,10-, 5,7,11-, 5,7,12-, 5,8,9-, 5,8,10-, 5,8,11-, 5,8,12-, 5,9,10-, 5,9,11-, 5,9,12-, 5,10,11-, 5,10,12-, 5,11,12-, 6,7,8-, 6,7,9-, 6,7,10-, 6,7,11-, 6,7,12-, 6,8,9-, 6,8,10-, 6,8,11-, 6,8,12-, 6,9, 10-, 6,9,11-, 6,9,12-, 6,10,11-, 6,10,12-, 6,11,12-, 7,8, 9-, 7,8,10-, 7,8,11-, 7,8,12-, 7,9,10-, 7,9,11-, 7,9,12-, 7,10,11-, 7,10,12-, 7,11,12-, 8,9,10-, 8,9,11-, 8,9,12-, 8,10,11-, 8,10,12-, 8,11,12-, 9,10,11-, 9,10,12-, 9,11, 12- and 10,11,12-trimethyltridecanoic acid; 2,3,4-, 2,3, 5-, 2,3,6-, 2,3,7-, 2,3,8-, 2,3,9-, 2,3,10-, 2,3,11-, 2,4,5-, 2,4,7-, 2,4,9-, 2,4,10-, 2,4,11-, 2,5,6-, 2,5,7-, 2,5,8-, 2,5,9-, 2,5,10-, 2,5,11-, 2,6,7-, 2,6,8-, 2,6,9-, 2,6,11-, 2,7,8-, 2,7,9-, 2,7,10-, 2,7,11-, 2,8,9-, 2,8,10-, 2,8,11-, 2,9,10-, 2,9,11-, 2,10,11-, 3,4,5-, 3,4,6-, 3,4,7-, 3,4,8-, 3,4,9-, 3,4,10-, 3,4,11-, 3,5,6-, 3,5,7-, 3,5,8-, 3,5,9-, 3,5,10-, 3,5,11-, 3,6,7-, 3,6,8-, 3,6,9-, 3,6,10-, 3,6,11-, 3,7,8-, 3,7,9-, 3,7,10-, 3,8,9-, 3,8,10-, 3,8,11-, 3,9,10-, 3,9,11-, 3,10,11-, 4,5,6-, 4,5,7-, 4,5,8-, 4,5,9-, 4,5,10-, 4,5,11-, 4,6,7-, 4,6,8-, 4,6,9-, 4,6,10-, 4,6,11-, 4,7,8-, 4,7,9-, 4,7,10-, 4,7,11-, 4,8,9-, 4,8,10-, 4,8,11-, 4,9,10-, 4,9,11-, 4,10,11-, 5,6,7-, 5,6,8-, 5,6,9-, 5,6,10-, 5,6,11-, 5,7,8-, 5,7,9-, 5,7,10-, 5,7,11-, 5,8,9-, 5,8,10-, 5,8,11-, 5,9,10-, 5,9,11-, 5,10,11-, 6,7,8-, 6,7,9-, 6,7,10-, 6,7, 11-, 6,8,9-, 6,8,10-, 6,8,11-, 6,9,10-, 6,9,11-, 6,10,11-, 7,8,9-, 7,8,10-, 7,8,11-, 7,9,10-, 7,9,11-, 7,10,11-, 8,9, 10-, 8,9,11-, 8,10,11- and 9,10,11-trimethyldodecanoic acid; 2,3,4-, 2,3,5-, 2,3,6-, 2,3,7-, 2,3,8-, 2,3,9-, 2,3,10-, 2,4,7-, 2,4,9-, 2,4,10-, 2,5,6-, 2,5,7-, 2,5,8-, 2,5,9-, 2,5,10-, 2,6,7-, 2,6,9-, 2,7,8-, 2,7,9-, 2,7,10-, 2,8,9-, 2,8,10-, 2,9,10-, 3,4,5-, 3,4,6-, 3,4,7-, 3,4,8-, 3,4,9-, 3,4,10-, 3,5,6-, 3,5,8-, 3,5,9-, 3,5,10-, 3,6,7-, 3,6,8-, 3,6,9-, 3,6,10-, 3,7,8-, 3,7,9-, 3,7,10-, 3,8,9-, 3,8,10-, 3,9,10-, 4,5,6-, 4,5,7-, 4,5,8-, 4,5,9-, 4,5,10-, 4,6,7-, 4,6,8-, 4,6,9-, 4,6,10-, 4,7,8-, 4,7,9-, 4,7,10-, 4,8,9-, 4,8,10-, 4,9,10-, 5,6,7-, 5,6,8-, 5,6,9-, 5,6,10-, 5,7,8-, 5,7,9-, 5,7,10-, 5,8,9-, 5,8,10-, 5,9,10-, 6,7,8-, 6,7,9-, 6,7,10-, 6,8,9-, 6,8,10-, 6,9,10-, 7,8,9-, 7,8,10-, 7,9,10- and 8,9,10-trimethylundecanoic acid; 2,3,4-, 2,3,5-, 2,3,6-, 2,3,7-, 2,3,8-, 2,3,9-, 2,4,5-, 2,4,7-, 2,4,9-, 2,5, 6-, 2,5,7-, 2,5,8-, 2,6,7-, 2,6,9-, 2,7,8-, 2,7,9-, 2,8,9-, 3,4,5-, 3,4,6-, 3,4,7-, 3,4,8-, 3,4,9-, 3,5,6-, 3,5,7-, 3,5, 8-, 3,5,9-, 3,6,7-, 3,6,8-, 3,6,9-, 3,7,8-, 3,7,9-, 3,8,9-, 4,5,6-, 4,5,7-, 4,5,8-, 4,5,9-, 4,6,7-, 4,6,9-, 4,7,8-, 4,7, 9-, 4,8,9-, 5,6,7-, 5,6,8-, 5,6,9-, 5,7,8-, 5,7,9-, 5,8,9-, 6,7,8-, 6,7,9-, 6,8,9- and 7,8,9-trimethyldecanoic acid; 2,3,4-, 2,3,5-, 2,3,6-, 2,3,7-, 2,3,8-, 2,4,5-, 2,4,6-, 2,4, 7-, 2,4,8-, 2,5,6-, 2,5,7-, 2,5,8-, 2,6,7-, 2,6,8-, 0.2,7,8-, 3,4,5-, 3,4,6-, 3,4,7-, 3,4,8-, 3,5,6-, 3,5,7-, 3,5,8-, 3,6, 7-, 3,6,8-, 3,7,8-, 4,5,6-, 4,5,7-, 4,5,8-, 4,6,7-, 4,6,8-, 4,7,8-, 5,6,7-, 5,6,8-, 5,7,8- and 6,7,8- trimethylnonanoic acid; and mixtures thereof;

(j) 3-butyl-4-ethyl, 3-pentyl-4-propyl, 3-butyl-4-propyl and 3-pentyl-4-ethylheptanoic acid; 3-butyl-4-methyl, 4-propyl-5-ethyl, 5-ethyl-6-propyl, 3-pentyl-4-ethyl, 4-butyl-5-propyl, 3-hexyl-4-propyl, 3-pentyl-4-methyl, 3-butyl-4-ethyl, 4-butyl-5-ethyl, 4,5-dipropyl, 3-pentyl-4-propyl, 3-hexyl-4-ethyl, 3-hexyl-4-butyl and 3-heptyl-4-propyloctanoic acid; 4-propyl-5-methyl, 3-pentyl-4-methyl, 4-butyl-5-ethyl, 5,6, dipropyl, 3-hexyl-4-ethyl, 4-pentyl-5-propyl, 3-heptyl-4-propyl, 3-butyl-4-methyl, 4-butyl-5-methyl, 4-propyl-5-ethyl, 5-ethyl-6-propyl, 5-propyl-6-ethyl, 3-hexyl-4-methyl, 3-pentyl-4-ethyl, 4-pentyl-5-ethyl, 4-butyl-5-propyl, 3-hexyl-4-propyl, 4-pentyl-5-butyl and 4-hexyl-5-propylnonanoic acid; 5-ethyl-6-methyl, 6-methyl-7-ethyl, 4-butyl-5-methyl, 4-pentyl-5-ethyl, 5-butyl-6-propyl, 4-propyl-5-methyl, 5,6-diethyl, 6,7-diethyl, 3-pentyl-4-methyl, 4-pentyl-5-methyl, 6-ethyl-7-propyl, 5-propyl-6-ethyl, 3-hexyl-4-methyl, 3-heptyl-4-ethyl, 4-hexyl-5-methyl, 4-butyl-5-ethyl, 6-methyl-7-propyl, 5-propyl-6-methyl, 5-butyl-6-ethyl, 3-heptyl-4-methyl, 3-hexyl-4-ethyl, 4-hexyl-5-ethyl, 4-pentyl-5-propyl, 5,6-dibutyl, 5-pentyl-6-propyl and 3-heptyl-4-methyldecanoic acid; 5-propyl-6-methyl, 6,7-diethyl, 7-methyl-8-propyl, 4-pentyl-5-methyl, 5-butyl-6-ethyl, 6,7-dipropyl, 3-heptyl-4-methyl, 4-hexyl-5-ethyl, 5-pentyl-6-propyl, 6-methyl-7-ethyl, 6-ethyl-7-methyl, 5-ethyl-6-methyl, 7-methyl-8-ethyl, 5-butyl-6-methyl, 4-butyl-5-methyl, 6-ethyl-7-propyl, 6-propyl-7-ethyl, 3-hexyl-4-methyl, 4-hexyl-5-methyl, 4-pentyl-5-ethyl, 5-pentyl-6-ethyl, 6-propyl-7-butyl and 6-butyl-7-propylundecanoic acid; 5-pentyl-6-methyl, 6,7-diethyl, 7,8-diethyl, 6-ethyl-7-methyl, 7-methyl-8-ethyl, 5-butyl-6-methyl, 7-ethyl-8-propyl, 6-propyl-7-ethyl, 4-hexyl-5-methyl, 5-pentyl-6-ethyl, 7-methyl-8-propyl, 6-propyl-7-methyl, 4-pentyl-5-methyl, 7-ethyl-8-butyl, 6-butyl-7-ethyl, 6-butyl-7-ethyl, 5-butyl-6-ethyl, 6,7-dipropyl and 7,8-dipropyldodecanoic acid; 7-ethyl-8-propyl, 7-propyl-8-ethyl, 7,8-dipropyl, 7,8-diethyl, 8-methyl-9-propyl, 6-propyl-7-methyl, 5-pentyl-6-methyl, 7-methyl-8-ethyl, 6-ethyl-7-methyl, 8-methyl-8-ethyl, 8-methyl-9-butyl, 6-butyl-7-methyl, 6-butyl-7-methyl, 5-butyl-6-methyl, 6-propyl-7-ethyl and 8-ethyl-9-propyltridecanoic acid; 6-propyl-7-methyl, 9-methyl-10-propyl, 8-ethyl-9-propyl, 7-ethyl-8-methyl, 7-propyl-8-ethyl, 8-methyl-9-ethyl, 8-methyl-9-propyl, 7-propyl-8-methyl, 7,8-diethyl and 8,9-diethyltetradecanoic acid; 8,9-diethyl, 9-methyl-10-propyl, 7-propyl-8-methyl, 8-methyl-9-ethyl, 8-ethyl-9-methyl, 7-ethyl-8-methyl and 9-methyl-10-ethylpentadecanoic acid; 8-ethyl-9-methyl and 9-methyl-10-ethylhexadecanoic acid; and mixtures thereof;

(k) mixtures of (a) to (j);

This composition of matter, when added to consumer product formulations, have many valuable effects and uses including, for example, as surfactants, cosurfactants, foam boosters, suds suppressors, calcium sequestrants/limesoap dispersants, crystal growth modifiers for the calcium soaps of straight-chain fatty acids, as consumer product physical property modifiers (for example as viscosity modifiers for liquid detergents), as soil modifiers for improving the removability of soil from a substrate, as dual-functional cleaning/care materials, as fungicides or antimicrobials, as consumer product dissolution aids, and as skin or hair feel improvement agents. Other uses, depending on the specific compounds used, include fabric softening and paper product formulation.

In a second embodiment of the invention, the branched carboxylic acid in the composition of matter can form one or more ester or amide linkages with a compound containing a nitrogen, preferably quaternary nitrogen, atom to produce fabric softening actives. Specifically, the actives preferably have the formulas:

1)

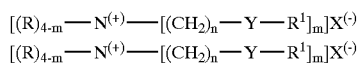

wherein each R substituent is hydrogen or a short chain $C_1$–$C_6$, preferably $C_1$–$C_3$ alkyl or hydroxyalkyl group, e.g., methyl (most preferred), ethyl, propyl, hydroxyethyl, and the like, benzyl, or mixtures thereof; each m is 2 or 3, preferably 2; each n is from 1 to about 4, preferably 2; each Y is —O—(O)C— or —(R)N—(O)C— preferably —O—

(O)C—; the sum of carbons in each $R^1$, plus one when Y is —O—(O)C— or —(R)N—(O)C— ("$YR^1$ sum"), is $C_6$–$C_{22}$, preferably $C_{12\text{-}22}$, more preferably $C_{14}$–$C_{20}$, (hereinafter, $R^1$ and $YR^1$ are used interchangeably to represent the hydrophobic chain, the $R^1$ chain lengths in general being even numbered for fatty alcohols and odd for fatty acids), but no more than one $YR^1$ sum being less than about 12 and then the other $R^1$, or $YR^1$, sum is at least about 16, with each $R^1$ comprising a long chain $C_5$–$C_{21}$ (or $C_6$–$C_{22}$), preferably $C_{10}$–$C_{20}$ (or $C_9$–$C_{19}$) unsaturated alkyl, most preferably $C_{12}$–$C_{18}$ (or $C_{11}$–$C_{17}$) unsaturated alkyl, or at lest one of the branched carboxylic acid in the composition of matter the ratio of the branched carboxylic acid to unsaturated alkyl being from about 1:0 to about 5:95, preferably from about 75:25 to about 25:75, more preferably from about 50:50 to about 30:70, and for the unsaturated alkyl group, the Iodine Value of the parent fatty acid of this $R^1$ group is preferably from about 20 to about 140, more preferably from about 50 to about 130; and most preferably from about 70 to about 115 and wherein the counterion, $X^-$, can be any softener-compatible anion, preferably, chloride, bromide, methylsulfate, ethylsulfate, sulfate, and/or nitrate, more preferably chloride and/or methylsulfate;

2)

$$\left[ R_3N^{(+)}CH_2CH \begin{matrix} YR^1 \\ \\ CH_2YR^1 \end{matrix} \right] X^{(-)}$$

wherein each Y, R, $R^1$, and $X^{(-)}$ have the same meanings as before (Such compounds include those having the formula:

$$[CH_3]_3N^{(+)}[CH_2CH(CH_2O(O)CR^1)O(O)CR^1]Cl^{(-)}$$

where —O—(O)$CR^1$ is derived partly from unsaturated, e.g., oleic, fatty acid and, preferably, each R is a methyl or ethyl group and preferably each $R^1$ is in the range of $C_{15}$ to $C_{19}$;

$$[R_{4-m}\text{—}N^{(+)}\text{—}R^1{}_m](X)^- \qquad (3)$$

wherein each m is 2 or 3, $R^1$ and $X^-$ have the same meanings as before;

4)

$$\left[ \begin{matrix} & N=CH_2 \\ R^1\text{—}C & \\ O & N^+\text{—}CH_2 \\ \| & / \backslash \\ R^1\text{—}C\text{—}G\text{—}R^2 & R \end{matrix} \right] X^-$$

wherein each R, $R^1$, and $X^-$ have the definitions given above; each $R^2$ is a $C_{1-6}$ alkylene group, preferably an ethylene group; and G is an oxygen atom or an —NR— group;

5)

$$\begin{matrix} & N\text{—}CH_2 \\ R^1\text{—}C & \\ O & N\text{—}CH_2 \\ \| & / \\ R^1\text{—}C\text{—}G\text{—}R^2 \end{matrix}$$

wherein $R^1$, $R^2$ and G are defined as above;

6) reaction products of substantially unsaturated and/or branched chain higher fatty acids with dialkylenetriamines in, e.g., a molecular ratio of about 2:1, said reaction products containing compounds of the formula:

$$R_1\text{—}C(O)\text{—}NH\text{—}R^2\text{—}NH\text{—}R^3\text{—}NH\text{—}C(O)\text{—}R^1$$

wherein $R^1$, $R^2$ are defined as above, and each $R^3$ is a $C_{1-6}$ alkylene group, preferably an ethylene group;

$$[R^1\text{—}C(O)\text{—}NR\text{—}R^2\text{—}N(R)_2\text{—}R^3\text{—}NR\text{—}C(O)\text{—}R^1]^+X^- \qquad (7$$

wherein R, $R^1$, $R^2$, $R^3$ and $X^-$ are defined as above;

8) the reaction product of substantially unsaturated and/or branched chain higher fatty acid with hydroxyalkylalkylenediamines in a molecular ratio of about 2:1, said reaction products containing compounds of the formula:

$$R^1\text{—}C(O)\text{—}NH\text{—}R^2\text{—}N(R^3OH)\text{—}C(O)\text{—}R^1$$

wherein $R^1$, $R^2$ and $R^3$ are defined as above;

9)

$$\left[ \begin{matrix} R & R \\ \backslash / & \backslash / \\ N\text{—}R^2\text{—}N \\ / \backslash & / \backslash \\ N & N \\ \| & \| \\ R^1 & R^1 \end{matrix} \right]^{2+} 2X^-$$

wherein R, $R^1$, $R^2$, and $X^-$ are defined as above;

10) acyclic quaternary ammonium salts having the formula:

$$[R^1\text{—}N(R^5)_2\text{—}R^6]^+X^-$$

wherein $R^5$ and $R^6$ are $C_1$–$C_4$ alkyl or hydroxyalkyl groups, and $R^1$ and $X^-$ are defined as herein above;

11) substituted imidazolinium salts having the formula:

$$\left[ \begin{matrix} & N\text{—}CH_2 \\ R^1\text{—}C & \\ \backslash & \\ & N\text{—}CH_2 \\ / & \\ R^7 & H \end{matrix} \right]^+ X^-$$

wherein $R^7$ is hydrogen or a $C_1$–$C_4$ saturated alkyl or hydroxyalkyl group, and $R^1$ and $X^-$ are defined as hereinabove;

12) substituted imidazolinium salts having the formula:

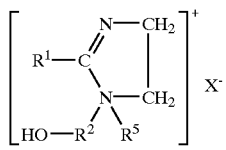

wherein $R^5$ is a $C_1$–$C_4$ alkyl or hydroxyalkyl group, and $R^1$, $R^2$, and $X^-$ are as defined above;

13) alkylpyridinium salts having the formula:

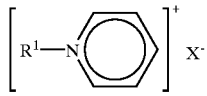

wherein $R^1$ and $X^-$ are defined as herein above;

14) alkanamide alkylene pyridinium salts having the formula:

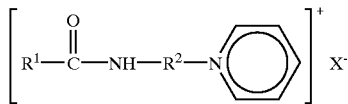

wherein $R^1$, $R^2$ and $X^-$ are defined as herein above; and.

15) mixtures thereof.

The above compounds preferably have a phase transition temperature of less than about 50° C., more preferably less than about 35° C., even more preferably less than about 20° C., and yet even more preferably less than about 0° C. Fabric softening compounds having such phase transition temperatures are easier to process, provide fabrics having improved water absorption properties, and provide superior fabric feel.

The present invention also relates to fabric softening compositions containing, as an essential component, from about 2% to about 80%, preferably from about 13% to about 75%, more preferably from about 15% to about 70%, and even more preferably from about 19% to about 65%, by weight of the composition, of said fabric softener actives, said fabric softener actives being selected from the compounds identified hereinbefore, and mixtures thereof. These fabric softening compositions contains:

A) from about 2% to about 80%, preferably from about 13% to about 75%, more preferably from about 15% to about 70%, and even more preferably from about 19% to about 65%, by weight of the composition, of biodegradable fabric softener active identified hereinbefore B) optionally, but preferably, the compositions can also contain an effective amount to improve clarity, less than about 40%, more preferably from about 10% to about 35%, more preferably from about 12% to about 25%, and even more preferably from about 14% to about 20%, by weight of the composition of principal solvent having a ClogP of from about −2.0 to about 2.6, more preferably from about −1.7 to about 1.6, and even more preferably from about −1.0 to about 1.0, as defined hereinafter" said principal solvent preferably selected from the group consisting of: 2,2,4-trimethyl-1,3-pentane diol; the ethoxylate, diethoxylate, or triethoxylate derivatives of 2,2,4-trimethyl-1,3-pentane diol; 2-ethylhexyl-1,3-diol; the ethoxylate, diethoxylate, or triethoxylate derivatives of 2-ethylhexyl-1,3-diol; 1,2 hexanediol; hexylene glycol; and mixtures thereof to provide a clear product;

C) optionally, but preferably, an effective amount, sufficient to improve clarity, of low molecular weight water soluble solvents like ethanol, isopropanol, propylene glycol, 1,3-propanediol, propylene carbonate, etc., said water soluble solvents being at a level that will not form clear compositions by themselves;

D) optionally, but preferably, an effective amount to improve clarity, of water soluble calcium and/or magnesium salt, preferably chloride; and E) the balance being water.

Preferably, the fabric softening compositions herein are aqueous, translucent or clear, preferably clear, compositions containing from about 3% to about 95%, preferably from about 10% to about 80%, more preferably from about 30% to about 70%, and even more preferably from about 40% to about 60%, water and from about 3% to about 40%, preferably from about 10% to about 35%, more preferably from about 12% to about 25%, and even more preferably from about 14% to about 20%, of the above principal alcohol solvent B. These preferred products (fabric softening compositions) are not translucent, or clear, without principal solvent B. The amount of principal solvent B. required to make the compositions translucent, or clear, is preferably more than 50%, more preferably more than about 60%, and even more preferably more than about 75%, of the total organic solvent present.

The fabric softening compositions can also be prepared as conventional dispersions of the fabric softener active containing from about 2% to about 50%, preferably from about 10% to about 40%, more preferably from about 15% to about 30%, of the fabric softener active. The fabric softening compositions can also be prepared as solids, either granular, or attached to substrates, as disclosed hereinafter.

The pH of the aqueous fabric softening compositions should be from about 1 to about 7, preferably from about 1.5 to about 5, more preferably from about 2 to about 3.5.

All percentages and proportions herein are by weight unless otherwise indicated. All documents are incorporated, in their relevant part, by reference.

DETAILED DESCRIPTION OF THE INVENTION

Highly preferred for the purpose of consumer cleaning products such as laundry detergents and personal care compositions of the invention, are the fatty acids and the salts identified hereinabove. The esters are not comparable in their utility for such products but may be useful as intermediates and in fabric conditioners and non-laundry applications also described herein.

As used herein the term branched carboxylic acid includes not only the branched carboxylic acid but also any stereoisomers, lower alkyl esters (preferably C1–C3, more preferably methyl esters) and salts (preferably sodium, potassium, ammonium, substituted ammonium, aluminum, zinc, calcium and magnesium salts). The composition of matter may also include mixtures, see herein after, for example, mixtures of acid, esters and salts with different or identical carbon chains. The composition of matter herein can be used alone, in mixtures with each other in any proportion, or in mixtures with any known (conventional) materials such as those disclosed in the background. We distinguish herein between (I) levels of any inventive compound in, on one hand, a mixture containing only the composition of matter or its mixtures with other conventional fatty acids or their derivatives and (II) levels of any composition of matter, or mixture containing same, in a fully-formulated consumer product. In terms of (I), levels suitable herein are typically about 1% or higher, preferably 5% or higher, more preferably 10% or higher, and commonly up to about 51% to 99.9%.

The invention also encompasses mixtures of the composition of matter(s) with known materials, i.e., levels are of the type (II). Such compositions include a composition comprising (new material) (i) from about 5% to about 99.9% of compounds according to any one or more of the ten aspects defined above; said composition further comprising (conventional material) (ii) from about 5% to about 95% of conventional compounds selected from linear fatty acid compounds or the C1–C3 alkyl esters (preferably methyl esters) or salts (preferably sodium, potassium, ammonium, substituted ammonium, aluminum, zinc, calcium and magnesium salts) of any of said (conventional) compounds. Alternatively, the conventional linear materials can be replaced by, or mixed with to provide comparable proportions, conventional alkyl-substituted fatty acid compounds or the stereoisomers, C1–C3 alkyl esters (preferably methyl esters) and salts (preferably sodium, potassium, ammonium, substituted ammonium, aluminum, zinc, calcium and magnesium salts) of any of said (conventional alkyl-substituted) compounds; and mixtures thereof.

To further illustrate, conventional alkyl-substituted fatty acid compounds (see background) permit the present invention to include a mixture of composition of the matter and further comprising from about 0.1% to about 95% of said conventional compounds, (ii), selected from the group consisting of: 2-methyl, 3-methyl, 4-methyl, 5-methyl, 6-methyl, 7-methyl, 8-methyl and 9-methyldecanoic acid; 2-methyl, 3-methyl, 4-methyl, 5-methyl, 6-methyl, 7-methyl, 8-methyl, 9-methyl and 10-methylundecanoic acid; 2-methyl, 3-methyl, 4-methyl, 5-methyl, 6-methyl, 7-methyl, 8-methyl, 9-methyl, 10-methyl and 11-methyldodecanoic acid; 2-methyl, 3-methyl, 4-methyl, 5-methyl, 8-methyl, 9-methyl, 11-methyl and 12-methyltridecanoic acid; 2-methyl, 3-methyl, 4-methyl, 5-methyl, 6-methyl, 7-methyl, 8-methyl, 9-methyl, 10-methyl, 1-methyl, 12-methyl and 13-methyltetradecanoic acid; 2-methyl, 3-methyl, 4-methyl, 6-methyl, 7-methyl, 10-methyl, 11-methyl, 12-methyl, 13-methyl and 14-methylpentadecanoic acid; 2-methyl, 3-methyl, 4-methyl, 5-methyl, 6-methyl, 7-methyl, 8-methyl, 9-methyl, 10-methyl, 11-methyl, 12-methyl, 13-methyl, 14-methyl and 15-methylhexadecanoic acid; 2-methyl, 3-methyl, 4-methyl, 5-methyl, 6-methyl, 7-methyl, 8-methyl, 9-methyl, 10-methyl, 11-methyl, 12-methyl, 13-methyl, 14-methyl, 15-methyl and 16-methylheptadecanoic acid; 2-methyl, 3-methyl, 4-methyl, 5-methyl, 6-methyl, 7-methyl, 8-methyl, 9-methyl, 10-methyl, 11-methyl, 12-methyl, 13-methyl, 14-methyl, 15-methyl, 16-methyl and 17-methyloctadecanoic acid; 2-methyl, 3-methyl, 4-methyl, 10-methyl, 17-methyl and 18-methylnonadecanoic acid; and the stereoisomers, C1–C3 alkyl esters (preferably methyl esters) and salts (preferably sodium, potassium, ammonium, substituted ammonium, aluminum, zinc, calcium and magnesium salts) of any of these compounds.

Certain very valuable mixtures of the invention are further illustrated by: a composition wherein the composition of matter includes:

one or more branched carboxylic acid of (b) and one or more branched carboxylic acid of (c) and one or more branched carboxylic acid of (i), optionally complemented by one or more branched carboxylic acid of (a);

one or more compounds branched carboxylic acid of (b), (d), (g) and (h) aspects optionally complemented by one or more branched carboxylic acid of (a);

one or more branched carboxylic acid of (b), (c), (d), (g) and (h) aspects optionally complemented by one or more branched carboxylic acid of (a); and one or more branched carboxylic acid of (b). (c), (d), (g), (h) and (i) aspects optionally complemented by one or more branched carboxylic acid of (a)

Other mixture-type compositions can include only different compounds of a single group of branched carboxylic acids, such as a mixture of branched carboxylic acids of (j); or any mixture in any proportions of any branched carboxylic acid of any of the branched carboxylic acids of (a)–(k) with any known branched fatty acids, whether saturated or unsaturated, including isostearic acid, isopalmitic acid or their unsaturated analogs.

Also encompassed by way of mixtures is a composition comprising (i) at least about 1% of the composition of matter of any one or more of the branched carboxylic acids (a)–(k) in said salt form; and (iii) at least about 1% of conventional fatty acids in salt form.

In terms of preferred composition of matter, there are also included herein any of the composition of matter being substantially free (the term generally meaning about 0.2% or less, or only adventitious amounts) of quaternary-carbon containing fatty acids or their salts or derivatives. Such materials reduce biodegradability of the compositions.

Another preferred composition comprises a mixture of the composition of matter of any one or more of the branched carboxylic acids (a)–(k) in which there are present at least some of the branched carboxylic acids which have an odd total number of carbon atoms, and at least some of the branched carboxylic acids having an even total number of carbon atoms.

In terms of the range in total carbon atoms in the composition of matter, the invention preferably encompasses a composition a mixture of the branched carboxylic acids (a)–(k), each of the branched carboxylic acids having a total of from 12 carbon atoms to 20 carbon atoms, more preferably from 14 carbon atoms to 19 carbon atoms, even more preferably from 15 carbon atoms to 18 carbon atoms.

Another preferred composition of the invention is based on any of the branched carboxylic acids (a)–(k), alone or in mixtures with conventional fatty acid derivatives and comprising a mixture of the compounds, the mixture containing not more than about 0.1% by weight of compounds having 12 or fewer, preferably not more than about 14 or fewer, carbon atoms.

Yet another preferred composition is a mixture of the composition of matter (or mixtures thereof with conventional fatty acids or derivatives) wherein any alkyl substituent in any of said compounds is methyl.

Another preferred composition of the invention is based on any of the branched carboxylic acids (a)–(k), in combination with conventional additives to form cleaning compositions, skin care compositions and personal cleansing compositions. The cleaning composition would comprise:

(i) from about 0.05% to about 99.9%, preferably 0.5% to about 95%, more preferably 1% to about 90%, even more preferably 5% to about 75% by weight of a composition of mater, namely any of the branched carboxylic acids (a)–(k), alone or in mixtures; and (ii) from about 0.0001 to about 99.99%, preferably 0.5% to about 95%, more preferably 1% to about 90%, even more preferably 5% to about 80% by weight of conventional cleaning additive.

The skin care composition would comprise:

(i) from about 0.05% to about 99.9%, preferably 0.5% to about 95%, more preferably 1% to about 90%, even more preferably 5% to about 75% by weight of a composition of mater namely any of the branched carboxylic acids (a)–(k), alone or in mixtures; and (ii) from about 0.0001 to about 99.99%, preferably 0.5% to about 95%, more preferably 1% to about 90%, even more preferably 5% to about 75% by weight of a conventional skin care additive.

The personal cleansing composition would comprise:

(i) from about 0.05% to about 99.9%, preferably 0.5% to about 95%, more preferably 1% to about 90%, even more preferably 5% to about 75% by weight of a composition of mater namely any of the branched carboxylic acids (a)–(k), alone or in mixtures; and (ii) from about 0.0001 to about 99.99%, preferably 0.5% to about 95%, more preferably 1% to about 90%, even more preferably 5% to about 75% by weight of a conventional personal cleansing additive.

Another preferred composition of the invention is paper article comprising at least about 0.0001% by weight of said composition of matter namely any of the branched carboxylic acids (a)–(k), alone or in mixtures. The paper article can be any conventional paper article well known in the art. This paper article can be in the form of a toilet tissue, a disposable tissue or disposable wipe.

It is also preferred that the composition of mater namely any of the branched carboxylic acids (a)–(k), alone or in mixtures comprise no more than about 0.1% aldehyde impurity. Furthermore, it is preferred that the composition of mater namely any of the branched carboxylic acids (a)–(k), alone or in mixtures comprise no more than about 0.1% unsaturated impurity.

It is also preferred that composition of mater namely any of the branched carboxylic acids (a)–(k), alone or in mixtures has at least 10%, more preferably of the branched carboxylic acid has from 16 to 17 carbon atoms in total. It is also preferred that the composition of mater namely any of the branched carboxylic acids (a)–(k), alone or in mixtures comprises a mixture of at least six, more preferably 20, even more preferably 40, of the branched carboxylic acid.

The fabric softening compositions described hereinbefore can optionally, but preferably comprise less than about 40%, preferably from about 10% to about 35%, more preferably from about 12% to about 25%, and even more preferably from about 14% to about 20%, of the principal solvent, by weight of the composition. Said principal solvent is selected to minimize solvent odor impact in the composition and to provide a low viscosity to the final composition.

The suitability of any principal solvent for the formulation of the liquid, concentrated, preferably clear, fabric softener compositions herein with the requisite stability is surprisingly selective. Suitable solvents can be selected based upon their octanol/water partition coefficient (P). Octanol/water partition coefficient of a principal solvent is the ratio between its equilibrium concentration in octanol and in water. The partition coefficients of the principal solvent ingredients of this invention are conveniently given in the form of their logarithm to the base 10, logP.

The logP of many ingredients has been reported; for example, the Pomona92 database, available from Daylight Chemical Information Systems, Inc. (Daylight CIS), Irvine, Calif., contains many, along with citations to the original literature. However, the logP values are most conveniently calculated by the "CLOGP" program, also available from Daylight CIS. This program also lists experimental logP values when they are available in the Pomona92 database. The "calculated logP" (ClogP) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990, incorporated herein by reference). The fragment approach is based on the chemical structure of each ingredient, and takes into account the numbers and types of atoms, the atom connectivity, and chemical bonding. These ClogP values, which are the most reliable and widely used estimates for this physicochemical property, are preferably used instead of the experimental logP values in the selection of the principal solvent ingredients which are useful in the present invention. Other methods that can be used to compute ClogP include, e.g., Crippen's fragmentation method as disclosed in J. Chem. Inf. Comput. Sci., 27, 21 (1987); Viswanadhan's fragmentation method as disclose in J. Chem. Inf. Comput. Sci., 29, 163 (1989); and Broto's method as disclosed in Eur. J. Med. Chem.—Chim. Theor., 19, 71 (1984). The principal solvents herein are selected from those having a ClogP of from about 0.15 to about 0.64, preferably from about 0.25 to about 0.62, and more preferably from about 0.40 to about 0.60, said principal solvent preferably being at least somewhat asymmetric, and preferably having a melting, or solidification, point that allows it to be liquid at, or near room temperature. Solvents that have a low molecular weight and are biodegradable are also desirable for some purposes. The more asymmetric solvents appear to be very desirable, whereas the highly symmetrical solvents such as 1,7-heptanediol, or 1,4-bis(hydroxymethyl) cyclohexane, which have a center of symmetry, appear to be unable to provide the essential clear compositions when used alone, even though their ClogP values fall in the preferred range.

The most preferred principal solvents can be identified by the appearance of the softener vesicles, as observed via cryogenic electron microscopy of the compositions that have been diluted to the concentration used in the rinse. These dilute compositions appear to have dispersions of fabric softener that exhibit a more unilamellar appearance than conventional fabric softener compositions. The closer to uni-lamellar the appearance, the better the compositions seem to perform. These compositions provide surprisingly good fabric softening as compared to similar compositions prepared in the conventional way with the same fabric softener active. The compositions also inherently provide improved perfume deposition as compared to conventional fabric softening compositions, especially when the perfume is added to the compositions at, or near, room temperature.

A comprehensive list of possible principal solvents can be found in U.S. Pat. No. 5,747,443, which is incorporated herein by reference.

The above fabric softeners can also be combined with other fabric softeners, such as, those in U.S. Pat. No. 3,861,870, Edwards and Diehl; U.S. Pat. No. 4,308,151, Cambre; U.S. Pat. No. 3,886,075, Bernardino; U.S. Pat. No. 4,233,164, Davis; U.S. Pat. No. 4,401,578, Verbruggen; U.S. Pat. No. 3,974,076, Wiersema and Rieke; and U.S. Pat. No. 4,237,016, Rudkin, Clint, and Young, all of said patents being incorporated herein by reference. The additional softener actives herein are preferably those that are highly branched and/or unsaturated versions of the traditional softener actives, i.e., di-long chain alkyl nitrogen derivatives, normally cationic materials, such as dioleyldimethylammonium chloride and imidazolinium compounds as described hereinafter. Examples of more biodegradable fabric softeners can be found in U.S. Pat. No. 3,408,361, Mannheimer, issued Oct. 29, 1968; U.S. Pat. No. 4,709,045, Kubo et al., issued Nov. 24, 1987; U.S. Pat. No. 4,233,451, Pracht et al., issued Nov. 11, 1980; U.S. Pat. No. 4,127,489, Pracht et al., issued Nov. 28, 1979; U.S. Pat. No. 3,689,424, Berg et al., issued Sep. 5, 1972; U.S. Pat. No. 4,128,485, Baumann et al., issued Dec. 5, 1978; U.S. Pat. No. 4,161,604, Elster et al., issued Jul. 17, 1979; U.S. Pat. No. 4,189,593, Wechsler et al., issued Feb. 19, 1980; and U.S. Pat. No. 4,339,391, Hoffman et al., issued Jul. 13, 1982, said patents being incorporated herein by reference.

An example of Compound 4. is 1-methyl-1-oleylamidoethyl-2-oleylimidazolinium methylsulfate wherein $R^1$ is as defined above, $R^2$ is an ethylene group, G is a NH group, $R^5$ is a methyl group and $X^-$ is a methyl sulfate anion.

An example of Compound 5. is 1-oleylamidoethyl-2-oleylimidazoline wherein $R^1$ is as defined above, $R^2$ is an ethylene group, and G is a NH group.

An example of Compound 6. is reaction products of oleic acids with diethylenetriamine in a molecular ratio of about 2:1, said reaction product mixture containing N,N"-dioleoyldiethylenetriamine with the formula:

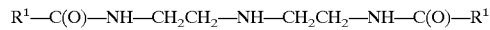

$$R^1-C(O)-NH-CH_2CH_2-NH-CH_2CH_2-NH-C(O)-R^1$$

wherein $R^1$—C(O) is oleoyl group of any of the novel branched acids described herein or any commercially available oleic acid derived from a vegetable or animal source, such as Emersol® 223LL or Emersol® 7021, available from Henkel Corporation, and $R^2$ and $R^3$ are divalent ethylene groups.

An example of Compound 7. is a difatty amidoamine based softener having the formula:

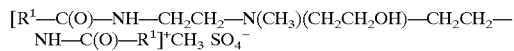

$$[R^1-C(O)-NH-CH_2CH_2-N(CH_3)(CH_2CH_2OH)-CH_2CH_2-NH-C(O)-R^1]^+CH_3\,SO_4^-$$

wherein $R^1$—C(O) is oleoyl group of any of the novel branched acids described herein or any commercially available oleic acid derived from a vegetable or animal source.

An example of Compound 8. is reaction products of oleic acids with N-2-hydroxyethylethylenediamine in a molecular ratio of about 2:1, said reaction product mixture containing a compound of the formula:

$$R^1-C(O)-NH-CH_2CH_2-N(CH_2CH_2OH)-C(O)-R^1$$

wherein $R^1$—C(O) is oleoyl group of any of the novel branched acids described herein or any commercially available oleic acid derived from a vegetable or animal source such as Emersol® 223LL or Emersol® 7021, available from Henkel Corporation.

An example of Compound 9. is the diquaternary compound having the formula:

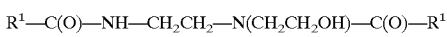
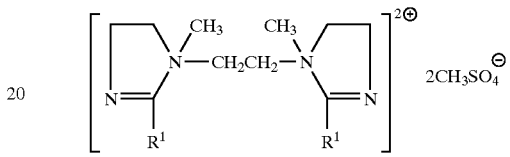

wherein $R^1$ is oleoyl group of any of the novel branched acids described herein.

An example of Compound 13. is 1-ethyl-1-(2-hydroxyethyl)-2-isoheptadecylimidazolinium ethylsulfate wherein $R^1$ is as defined above, $R^2$ is an ethylene group, $R^5$ is an ethyl group, and $X^-$ is an ethylsulfate anion.

The invention has numerous additional useful embodiments as described and illustrated in the examples, detergent examples and claims hereinafter.

GENERAL PROCEDURE I

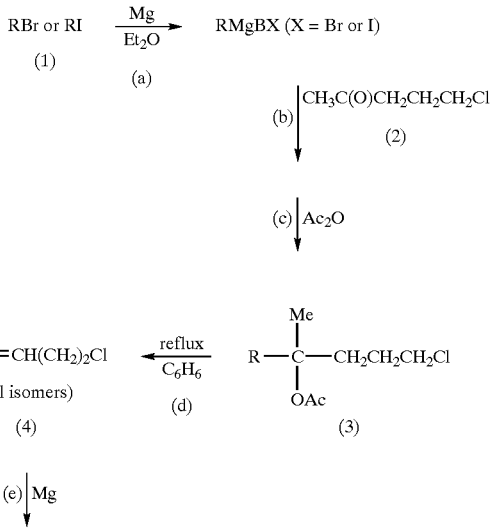

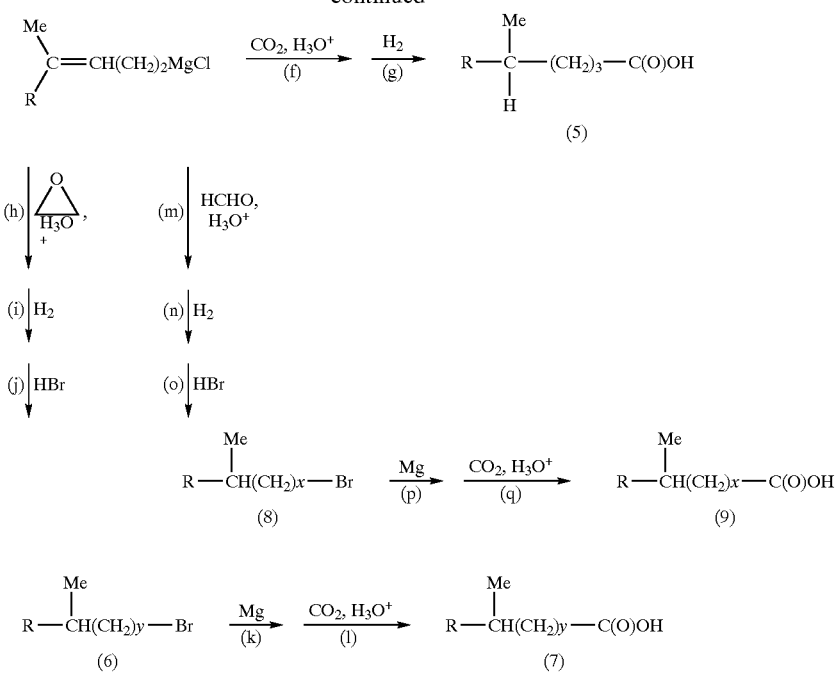
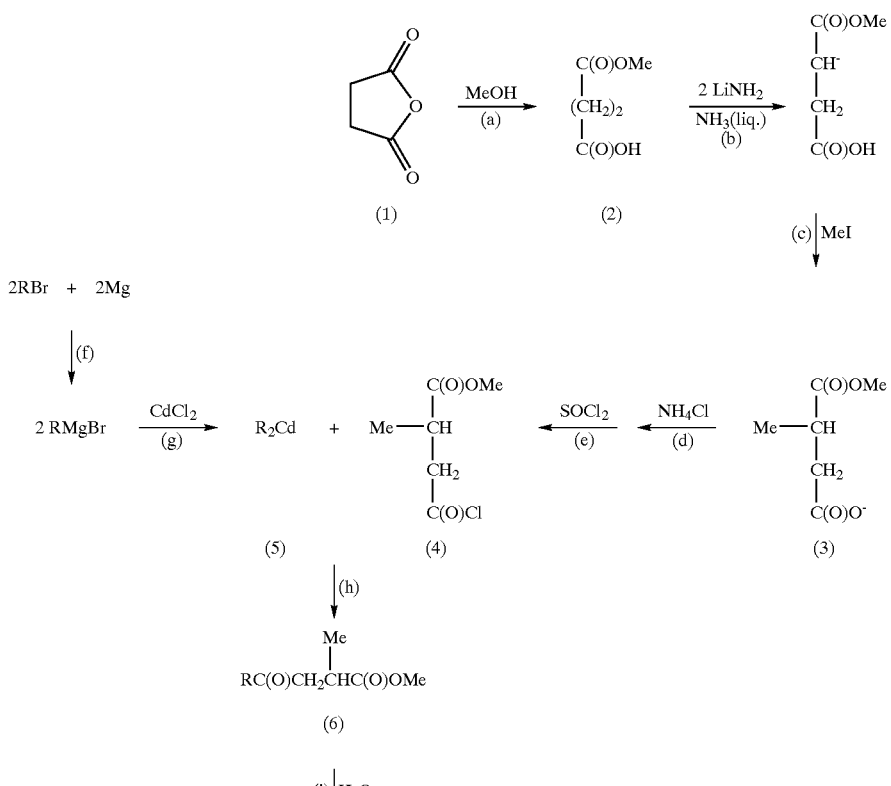
GENERAL PROCEDURE II
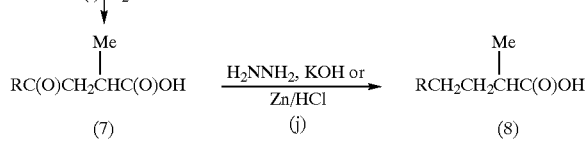

GENERAL PROCEDURE III
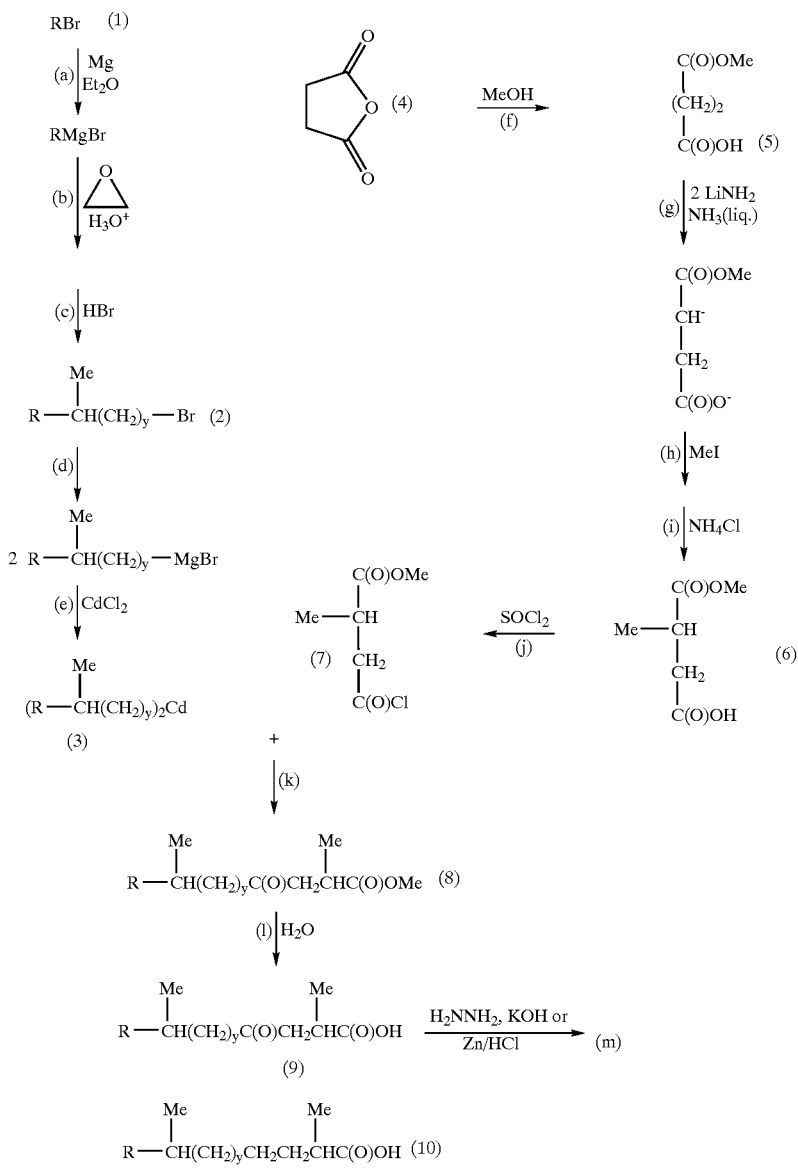
GENERAL PROCEDURE IV
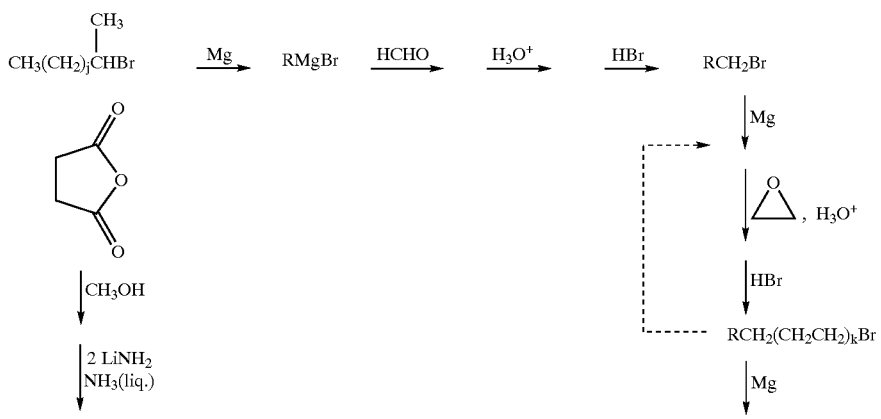

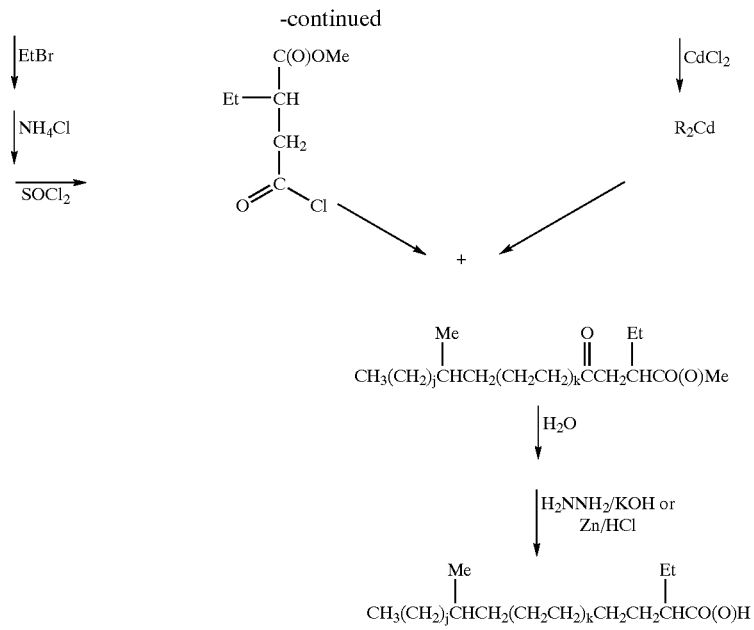
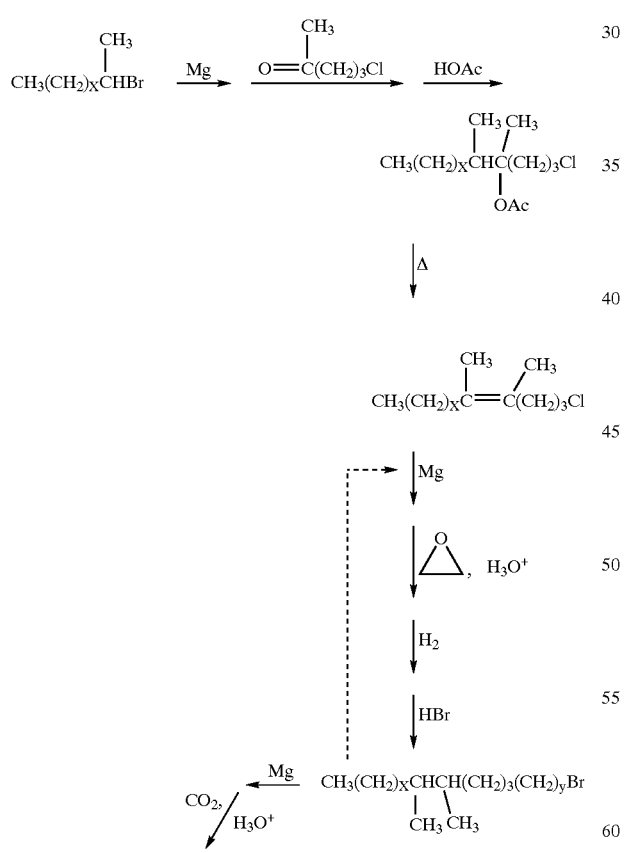
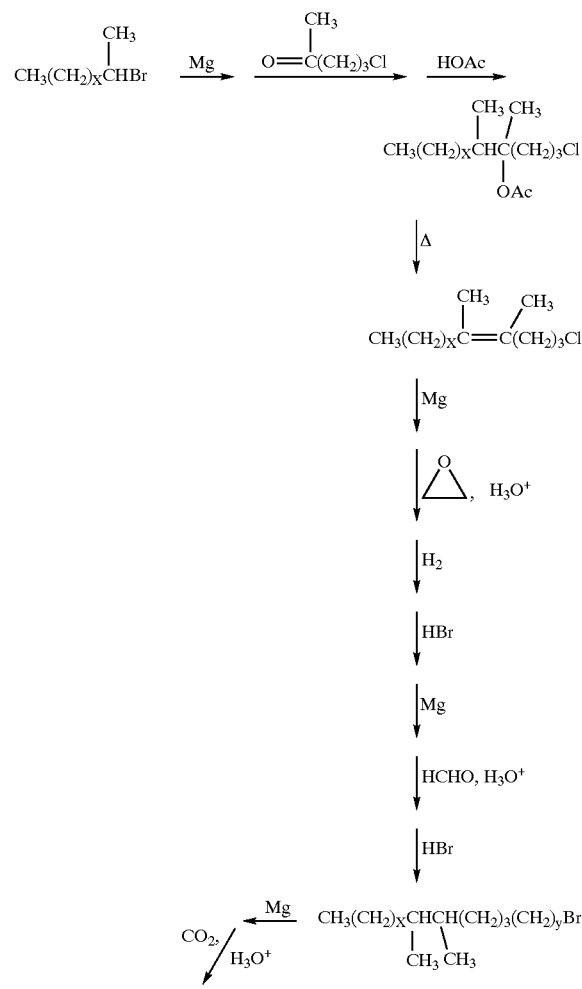

29
-continued
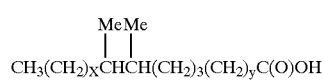
GENERAL PROCEDURE VII
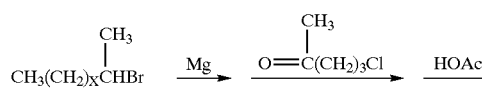
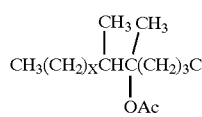
30
-continued
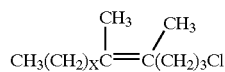
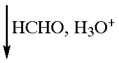
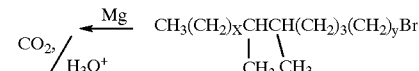
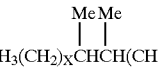
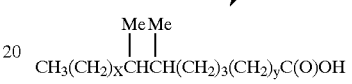
GENERAL PROCEDURE VIII
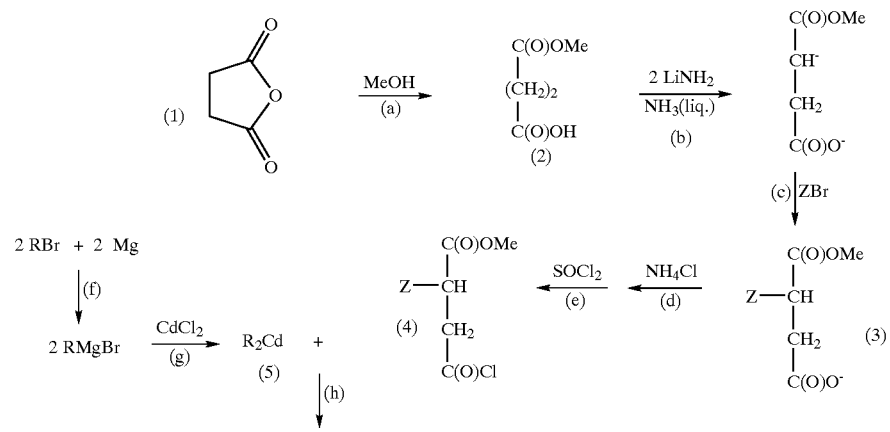
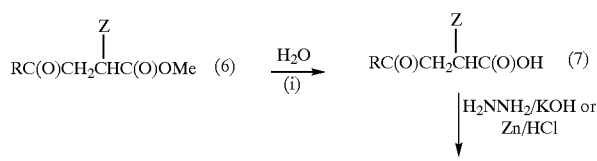

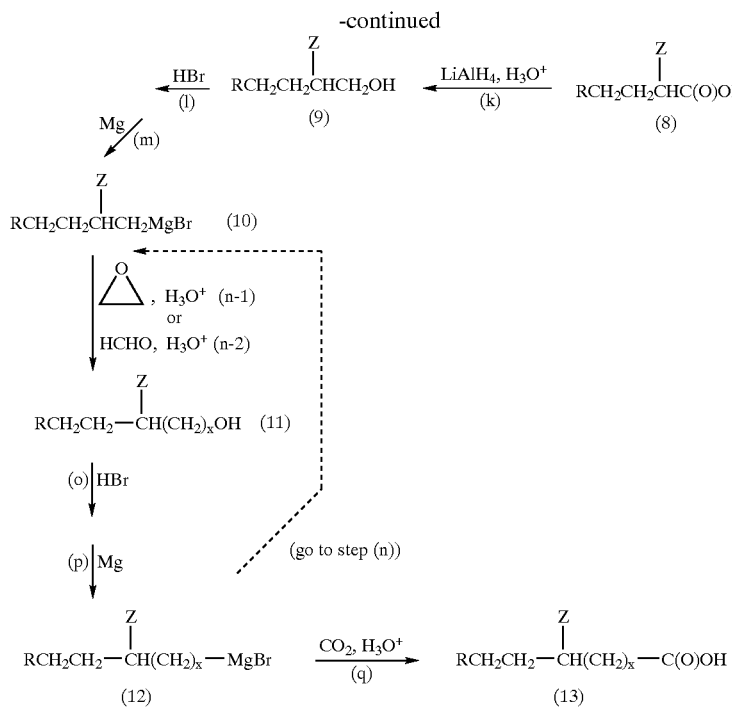

EXAMPLE 1

5-methylpentadecanoic Acid

See GENERAL PROCEDURE I. Decyl bromide (compound (1), R=CH$_3$(CH$_2$)$_9$—) is converted to its Grignard reagent with magnesium in dry ether (I, Step (a)). To this is added 5-chloro-2-pentanone (Aldrich C6,2660-3) (I, Step (b)). The reaction mixture is worked up with acetic anhydride (I, Step (c)) to form chloroacetate (3). Acetic acid is eliminated by refluxing (3) in a suitable solvent, e.g., benzene (I, Step (d)) yielding a mixture of chloro-olefin isomers (4). (4) is converted to its Grignard reagent following standard practice. (I, Step (e)). The Grignard reagent is treated with carbon dioxide and aqueous acidic workup (I, Step (f)) followed by catalytic hydrogenation (Pd catalyst) to form 5-methylpentadecanoic acid, (5).

EXAMPLE 2

7-methyltridecanoic Acid

See GENERAL PROCEDURE I. Hexyl bromide (compound (1), R=CH$_3$(CH$_2$)$_5$—) is converted to its Grignard reagent with magnesium in dry ether (I, Step (a)). To this is added 5-chloro-2-pentanone (Aldrich C6,2660-3) (I, Step (b)). The reaction mixture is worked up with acetic anhydride (1, Step (c)) to form chloroacetate (3). Acetic acid is eliminated by refluxing (3) in a suitable solvent, e.g., benzene (I, Step (d)) yielding a mixture of chloro-olefin isomers (4) (R=CH$_3$(CH$_2$)$_5$—). (4) is converted to its Grignard reagent following standard practice. (I, Step (e)). The Grignard reagent is treated with ethylene oxide followed by aqueous acidic workup (I, Step (h)), hydrogenation (I, Step (i)), Pd catalyst, and hydrobromination (I, Step (j)). The alkyl bromide (6) (R=CH$_3$(CH$_2$)$_5$—, y=5) is converted to the Grignard reagent with magnesium (I, Step (k)), which is treated with carbon dioxide and aqueous acidic workup (I, Step (1)) to give the product, 7-methyltridecanoic acid, (7).

EXAMPLE 3

8-methylpentadecanoic Acid

See GENERAL PROCEDURE I. Heptyl bromide (compound (1), R=CH$_3$(CH$_2$)$_6$—) is converted to its Grignard reagent with magnesium in dry ether (I, Step (a)). To this is added 5-chloro-2-pentanone (Aldrich C6,2660-3) (I, Step (b)). The reaction mixture is worked up with acetic anhydride (I, Step (c)) to form chloroacetate (3). Acetic acid is eliminated by refluxing (3) in a suitable solvent, e.g., benzene (I, Step (d)) yielding a mixture of chloro-olefin isomers (4) (R=CH$_3$(CH$_2$)$_6$—). (4) is converted to its Grignard reagent following standard practice. (I, Step (e)). The Grignard reagent is treated with ethylene oxide followed by aqueous acidic workup (I, Step (h)), hydrogenation (I, Step (i)), Pd catalyst, and hydrobromination (I, Step (j)). The alkyl bromide (6) (R=CH$_3$(CH$_2$)$_6$—, y=5) is converted to the Grignard reagent with magnesium (I, Step (k)), which is treated with formaldehyde, and aqueous workup (I, Step (m)). Alkyl halide (8) (R=CH$_3$(CH$_2$)$_6$—, x=6) is formed by hydrobromination (I, Step (o)). This is converted to its Grignard reagent with magnesium in dry ether (I, Step (p)) followed by treatment with carbon dioxide and aqueous acidic workup (I, Step (q)) to give the product, 8-methylpentadecanoic acid, (9).

EXAMPLE 4

9-methylpentadecanoic Acid

See GENERAL PROCEDURE I. Hexyl bromide (compound (1), R=CH$_3$(CH$_2$)$_5$—) is converted to its Grignard reagent with magnesium in dry ether (I, Step (a)). To this is added 5-chloro-2-pentanone (Aldrich C6,2660-3) (I, Step (b)). The reaction mixture is worked up with acetic anhydride (I, Step (c)) to form chloroacetate (3). Acetic acid is eliminated by refluxing (3) in a suitable solvent, e.g., benzene (I, Step (d)) yielding a mixture of chloro-olefin isomers (4) (R=CH$_3$(CH$_2$)$_5$—). (4) is converted to its Grignard reagent following standard practice. (I, Step (e)). The Grignard reagent is treated with ethylene oxide followed by aqueous acidic workup (I, Step (h)), hydrogenation (I, Step (i)), Pd catalyst, and hydrobromination (I, Step (j)). The alkyl bromide (6) (R=$CH_3(CH_2)_5$—, y=5) is converted to the Grignard reagent with magnesium (I, Step (k)) which is treated with ethylene oxide and aqueous acidic workup (I, Step (h)) and hydrobromination (I, Step (j)). The alkyl bromide (6) (R=$CH_3(CH_2)_5$—, y=7) is converted to the Grignard reagent with magnesium (I, Step (k)) which is treated with carbon dioxide and aqueous acidic workup (I, Step (l)) to give the product, 9-methylpentadecanoic acid, (7).

EXAMPLE 5

10-methyltridecanoic Acid

See GENERAL PROCEDURE I. 1-propyl bromide (compound (1), R=$CH_3(CH_2)_2$—) is converted to its Grignard reagent with magnesium in dry ether (I, Step (a)). To this is added 5-chloro-2-pentanone (Aldrich C6,2660-3) (I, Step (b)). The reaction mixture is worked up with acetic anhydride (I, Step (c)) to form chloroacetate (3). Acetic acid is eliminated by refluxing (3) in a suitable solvent, e.g., benzene (I, Step (d)) yielding a mixture of chloro-olefin isomers (4) (R=$CH_3(CH_2)_2$—). (4) is converted to its Grignard reagent following standard practice. (I, Step (e)). The Grignard reagent is treated with ethylene oxide followed by aqueous acidic workup (I, Step (h)), hydrogenation (I, Step (i)), Pd catalyst, and hydrobromination (I, Step (j)). The alkyl bromide (6) (R=$CH_3(CH_2)_2$—, y=5) is converted to the Grignard reagent with magnesium (I, Step (k)). Departing from General Procedure I, this Grignard reagent is again treated with ethylene oxide followed by aqueous acidic workup and hydrobromination. The intermediate alkyl bromide, $CH_3(CH_2)_2CH(Me)(CH_2)_7Br$, is converted to the Grignard reagent with magnesium, which, returning to the general procedure I at step (I m), is treated with formaldehyde, and aqueous workup (I, Step (m). Alkyl halide (8) (R=$CH_3(CH_2)_2$—, x=8) is formed by hydrobromination (I, Step (o)). This is converted to its Grignard reagent with magnesium in dry ether (I, Step (p)) followed by treatment with carbon dioxide and aqueous acidic workup (I, Step (q)) to give the product, 10-methyltridecanoic acid, (9).

EXAMPLE 6

6-propyltetradecanoic Acid

Following General Procedure VIII use 1-bromopropane in step (c) (Z=$CH_3(CH_2)_2$—) and use 1-bromohexane in step (f) (R=$CH_3(CH_2)_5$—) to eventually obtain 2-propyl-1-decanol as compound (9). This is converted to its bromide in step (1) and to its Grignard reagent in step (m). Following the sequence (n–1), (o), (p), (n–2), (o), (p) (that is, one ethylene oxide iteration and one formaldehyde iteration) gives final Grignard reagent (12), x=4, R=n-hexyl, Z=n-Pr which with $CO_2$ treatment gives 6-propyltetradecanoic acid (13) (x=4, R=n-hexyl, Z=n-Pr).

EXAMPLE 7

8-ethylpentadecanoic Acid

Following General Procedure VII use ethyl bromide in step (c) (Z=$CH_3CH_2$—) and use 1-bromopentane in step (f) (R=$CH_3(CH_2)_4$—) to eventually obtain 2-ethyl-1-nonanol as compound (9). This is converted to its bromide in step (1) and to its Grignard reagent in step (m). Following the sequence (n–1), (o), (p), (n–1), (o), (p), (n–2), (o), (p) (that is, two ethylene oxide iterations and one formaldehyde iteration) gives final Grignard reagent (12), x=6, R=n-pentyl, Z=Et which with $CO_2$ treatment gives 8-ethylpentadecanoic acid (13) (x=6, R=n-pentyl, Z=Et).

EXAMPLE 8

6-methyltridecanoic Acid

See GENERAL PROCEDURE I. Heptyl bromide (compound (1), R=$CH_3(CH_2)_6$—) is converted to its Grignard reagent with magnesium in dry ether (I, Step (a)). To this is added 5-chloro-2-pentanone (Aldrich C6,2660-3) (I, Step (b)). The reaction mixture is worked up with acetic anhydride (I, Step (c)) to form chloroacetate (3). Acetic acid is eliminated by refluxing (3) in a suitable solvent, e.g., benzene (I, Step (d)) yielding a mixture of chloro-olefin isomers (4) (R=$CH_3(CH_2)_6$—). (4) is converted to its Grignard reagent following standard practice. (I, Step (e)). This is treated with formaldehyde step and aqueous workup (I m), hydrogenation (I n). Alkyl halide (8) (R=$CH_3(CH_2)_6$—, x=4) is formed by hydrobromination (I, Step (o)). This is converted to its Grignard reagent with magnesium in dry ether (I, Step (p)) followed by treatment with carbon dioxide and aqueous acidic workup (I, Step (q)) to give the product, 6-methyltridecanoic acid, (9).

EXAMPLE 9

2,5-dimethyltetradecanoic Acid

Succinic anhydride is opened using methanol (II, step (a)) to give monomethyl succinate (2). This is treated with 2+equivalents of lithium amide in liquid ammonia (II, step (b)) to form its dianion which is alkylated by the addition of one mole of methyl iodide in ether (II, step (c)) and treatment with ammonium chloride (II, step (d)), giving 2-methylsuccinic acid, 1-methyl ester (3). This is treated with thionyl chloride (II, step (e)) to give the corresponding acid chloride (4).

A Grignard reagent is made from 2-bromoundecane and magnesium (II, step (f)) which is treated (II, step (g)) with cadmium chloride to form the corresponding dialkylcadmium, di(2-undecyl)cadmium, (5).

The dialkylcadmium reagent (5) is allowed to react with the acid chloride compound (4) (II, step (h)) to form (6) (R=2-undecyl). This is hydrolyzed to the corresponding keto-acid (7) which is reduced either with the Wolff-Kishner or Clemmensen reductions II, step (j)) to give 2,5-dimethyltetradecanoic acid.

EXAMPLE 10

2,7-dimethyltetradecanoic Acid

The compound is prepared from 2-nonyl bromide (1) and succinic anhydride using Procedure III. y=2.

EXAMPLE 11

2,9-dimethyltetradecanoic Acid

Succinic anhydride is opened using methanol (II, step (a)) to give monomethyl succinate (2). This is treated with 2+equivalents of lithium amide in liquid ammonia (II, step (b)) to form its dianion which is alkylated by the addition of one mole of methyl iodide in ether (II, step (c)) and treatment with ammonium chloride (II, step (d)), giving 2-methylsuccinic acid, 1-methyl ester (3). This is treated with thionyl chloride (II, step (e)) to give the corresponding acid chloride (4).

Now see GENERAL PROCEDURE I. 1-pentyl bromide (compound (1), R=CH$_3$(CH$_2$)$_4$—) is converted to its Grignard reagent with magnesium in dry ether (I, Step (a)). To this is added 5-chloro-2-pentanone (Aldrich C6,2660-3) (I, Step (b)). The reaction mixture is worked up with acetic anhydride (I, Step (c)) to form chloroacetate (3). Acetic acid is eliminated by refluxing (3) in a suitable solvent, e.g., benzene (I, Step (d)) yielding a mixture of chloro-olefin isomers (4) (R=CH$_3$(CH$_2$)$_4$—). (4) is converted to its Grignard reagent following standard practice. (I, Step (e)). The Grignard reagent is treated with formaldehyde and aqueous workup (I, Step (m)) and hydrogenated (I, Step (n)), Pd catalyst, and hydrobrominated (I, Step (o)) to give the alkyl bromide (8) (R=CH$_3$(CH$_2$)$_4$—, x=4). Now this compound (8) of Procedure I is carried over and used following part of the procedure shown in GENERAL PROCEDURE II, as an alkyl halide and is converted to the Grignard reagent with magnesium (II, Step (f)). The Grignard reagent is converted to a dialkylcadmium (5), di(5-methyl-1-decyl)cadmium (II, (g)). The dialkylcadmium is reacted (II, step (h)) with the acid chloride of 2-methylsuccinic acid 1-methyl ester (compound (4) prepared supra) yielding compound (6), R=5-methyl-1-decyl-. This is hydrolyzed to the corresponding keto-acid (7) which is reduced either with the Wolff-Kishner or Clemmensen reductions (II, step (j)) to give 2,9-dimethyltetradecanoic acid.

EXAMPLE 12

2,11-dimethyltetradecanoic Acid

Succinic anhydride is opened using methanol (II, step (a)) to give monomethyl succinate (2). This is treated with 2+ equivalents of lithium amide in liquid ammonia (II, step (b)) to form its dianion which is alkylated by the addition of one mole of methyl iodide in ether (II, step (c)) and treatment with ammonium chloride (II, step (d)), giving 2-methylsuccinic acid, 1-methyl ester (3). This is treated with thionyl chloride (II, step (e)) to give the corresponding acid chloride (4).

Now see GENERAL PROCEDURE I. 1-propyl bromide (compound (1), R=CH$_3$(CH$_2$)$_2$—) is converted to its Grignard reagent with magnesium in dry ether (I, Step (a)). To this is added 5-chloro-2-pentanone (Aldrich C6,2660-3) (I, Step (b)). The reaction mixture is worked up with acetic anhydride (I, Step (c)) to form chloroacetate (3). Acetic acid is eliminated by refluxing (3) in a suitable solvent, e.g., benzene (I, Step (d)) yielding a mixture of chloro-olefin isomers (4) (R=CH$_3$(CH$_2$)$_2$—). (4) is converted to its Grignard reagent following standard practice. (I, Step (e)). The Grignard reagent is treated with formaldehyde and aqueous workup (I, Step (m)) and hydrogenated (I, Step (n)), Pd catalyst, and hydrobrominated (I, Step (o)) to give the alkyl bromide (8) (R=CH$_3$(CH$_2$)$_2$—, x=4). Now following another part of the procedure shown in GENERAL PROCEDURE I, compound (8) is used instead of compound (4) of Procedure I as an alkyl halide and is converted to a Grignard reagent with magnesium (I, Step (e)). The Grignard reagent is treated with ethylene oxide followed by aqueous acidic workup (I, Step (h)), and hydrobromination (I, Step (j)), to give compound (6) (R=7-methyl-1-decyl, y=6). Now this compound (6) is used in another part of the procedure shown in GENERAL PROCEDURE II, namely, step (II, (f)) where it is converted to a Grignard reagent. The Grignard reagent is converted to a dialkylcadmium (5), di(7-methyl-1-decyl)cadmium (II, (g)). The dialkylcadmium is reacted (II, step (h)) with the acid chloride of 2-methylsuccinic acid 1-methyl ester (compound (4) prepared supra) yielding compound (6), R=7-methyl-1-decyl-. This is hydrolyzed to the corresponding keto-acid (7) which is reduced either with the Wolff-Kishner or Clemmensen reductions (II, step (j)) to give 2,11-dimethyltetradecanoic acid.

EXAMPLE 13

2,13-dimethyltetradecanoic Acid

Succinic anhydride is opened using methanol (II, step (a)) to give monomethyl succinate (2). This is treated with 2+equivalents of lithium amide in liquid ammonia (II, step (b)) to form its dianion which is alkylated by the addition of one mole of methyl iodide in ether (II, step (c)) and treatment with ammonium chloride (II, step (d)), giving 2-methylsuccinic acid, 1-methyl ester (3). This is treated with thionyl chloride (II, step (e)) to give the corresponding acid chloride (4).

Now see GENERAL PROCEDURE I. Methyl iodide (compound (1)) is converted to its Grignard reagent with magnesium in dry ether (I, Step (a)). To this is added 5-chloro-2-pentanone (Aldrich C6,2660-3) (I, Step (b)). The reaction mixture is worked up with acetic anhydride (I, Step (c)) to form chloroacetate (3). Acetic acid is eliminated by refluxing (3) in a suitable solvent, e.g., benzene (I, Step (d)) yielding a mixture of chloro-olefin isomers (4) (R=CH$_3$—). (4) is converted to its Grignard reagent following standard practice. (I, Step (e)). The Grignard reagent is treated with formaldehyde and aqueous workup (1, Step (m)) and hydrogenated (1, Step (n)), Pd catalyst, and hydrobrominated (I, Step (o)) to give the alkyl bromide (8) (R=CH$_3$—, x=4). Now following another part of the procedure shown in GENERAL PROCEDURE I, compound (8) is used instead of compound (4) of Procedure I as an alkyl halide and is converted to a Grignard reagent with magnesium (I, Step (e)). The Grignard reagent is treated with ethylene oxide followed by aqueous acidic workup (I, Step (h)), and hydrobromination (I, Step (j)), to give compound (6) (R=Methyl, y=6). In a second Grignard/ethylene oxide loop, compound (6) is converted to its Grignard reagent, treated with ethylene oxide followed by aqueous acidic workup (I, Step (h)), and hydrobromination (I, Step (j)), to give a new compound (6) (R=Methyl, y=8).

Now this compound (6) is used in another part of the procedure shown in GENERAL PROCEDURE II, namely, step (II, (f)) where it is converted to a Grignard reagent. The Grignard reagent is converted to a dialkylcadmium (5), di(9-methyl-1-decyl)cadmium (II, (g)). The dialkylcadmium is reacted (II, step (h)) with the acid chloride of 2-methylsuccinic acid 1-methyl ester (compound (4) prepared supra) yielding compound (6), R=9-methyl-1-decyl-. This is hydrolyzed to the corresponding keto-acid (7) which is reduced either with the Wolff-Kishner or Clemmensen reductions (II, step (j)) to give 2,13-dimethyltetradecanoic acid.

EXAMPLE 14

2,15-dimethylhexadecanoic Acid

Succinic anhydride is opened using methanol (II, step (a)) to give monomethyl succinate (2). This is treated with 2+equivalents of lithium amide in liquid ammonia (II, step (b)) to form its dianion which is alkylated by the addition of one mole of methyl iodide in ether (II, step (c)) and treatment with ammonium chloride (II, step (d)), giving 2-methylsuccinic acid, 1-methyl ester (3). This is treated with thionyl chloride (II, step (e)) to give the corresponding acid chloride (4).

Now see GENERAL PROCEDURE I. Methyl iodide (compound (1)) is converted to its Grignard reagent with magnesium in dry ether (I, Step (a)). To this is added 5-chloro-2-pentanone (Aldrich C6,2660-3) (I, Step (b)). The reaction mixture is worked up with acetic anhydride (I, Step (c)) to form chloroacetate (3). Acetic acid is eliminated by refluxing (3) in a suitable solvent, e.g., benzene (I, Step (d)) yielding a mixture of chloro-olefin isomers (4) (R=$CH_3$—). (4) is converted to its Grignard reagent following standard practice. (I, Step (e)). The Grignard reagent is treated with formaldehyde and aqueous workup (I, Step (m)) and hydrogenated (I, Step (n)), Pd catalyst, and hydrobrominated (I, Step (o)) to give the alkyl bromide (8) (R=$CH_3$—, x=4). Now following another part of the procedure shown in GENERAL PROCEDURE I, compound (8) is used instead of compound (4) of Procedure I as an alkyl halide and is converted to a Grignard reagent with magnesium (I, Step (e)). The Grignard reagent is treated with ethylene oxide followed by aqueous acidic workup (I, Step (h)), and hydrobromination (I, Step (o)), to give compound (6) (R=Methyl, y=6). In two additional Grignard/ethylene oxide loops, compound (6) is converted to Grignard reagent, treated with ethylene oxide followed by aqueous acidic workup (I, Step (h)), and hydrobromination (I, Step (j)), ultimately giving compound (6) (R=Methyl, y=10). Now this compound (6) is used in another part of the procedure shown in GENERAL PROCEDURE II, namely, step (II, (f)) where it is converted to a Grignard reagent. The Grignard reagent is converted to a dialkylcadmium (5), di(11-methyl-1-dodecyl)cadmium (II, (g)). The dialkylcadmium is reacted (II, step (h)) with the acid chloride of 2-methylsuccinic acid 1-methyl ester (compound (4) prepared supra) yielding compound (6), R=11-methyl-1-dodecyl-. This is hydrolyzed to the corresponding keto-acid (7) which is reduced either with the Wolff-Kishner or Clemmensen reductions (II, step (j)) to give 2,15-dimethylhexadecanoic acid.

EXAMPLE 15

2,17-dimethyloctadecanoic Acid

Succinic anhydride is opened using methanol (II, step (a)) to give monomethyl succinate (2). This is treated with 2+ equivalents of lithium amide in liquid ammonia (II, step (b)) to form its dianion which is alkylated by the addition of one mole of methyl iodide in ether (II, step (c)) and treatment with ammonium chloride (II, step (d)), giving 2-methylsuccinic acid, 1-methyl ester (3). This is treated with thionyl chloride (II, step (e)) to give the corresponding acid chloride (4).

Now see GENERAL PROCEDURE I. Methyl bromide (compound (1)) is converted to its Grignard reagent with magnesium in dry ether (I, Step (a)). To this is added 5-chloro-2-pentanone (Aldrich C6,2660-3) (I, Step (b)). The reaction mixture is worked up with acetic anhydride (I, Step (c)) to form chloroacetate (3). Acetic acid is eliminated by refluxing (3) in a suitable solvent, e.g., benzene (I, Step (d)) yielding a mixture of chloro-olefin isomers (4) (R=$CH_3$—). (4) is converted to its Grignard reagent following standard practice. (I, Step (e)). The Grignard reagent is treated with formaldehyde and aqueous workup (I, Step (m)) and hydrogenated (I, Step (n)), Pd catalyst, and hydrobrominated (I, Step (o)) to give the alkyl bromide (8) (R=$CH_3$—, x=4). Now following another part of the procedure shown in GENERAL PROCEDURE I, compound (8) is used instead of compound (4) of Procedure I as an alkyl halide and is converted to a Grignard reagent with magnesium (I, Step (e)). The Grignard reagent is treated with ethylene oxide followed by aqueous acidic workup (I, Step (h)), and hydrobromination (I, Step (j)), to give compound (6) (R=Methyl, y=6). In three Grignard/ethylene oxide loops, compound (6) is converted to Grignard reagent, treated with ethylene oxide followed by aqueous acidic workup (I, Step (h)), and hydrobromination (I, Step (j)), ultimately giving compound (6) (R=Methyl, y=12). Now this compound (6) is used in another part of the procedure shown in GENERAL PROCEDURE U, namely, step (II, (f)) where it is converted to a Grignard reagent. The Grignard reagent is converted to a dialkylcadmium (5), R=di(13-methyl-1-tetradecyl)cadmium (II, (g)). The dialkylcadmium is reacted (II, step (h)) with the acid chloride of 2-methylsuccinic acid 1-methyl ester (compound (4) prepared supra) yielding compound (6), R=13-methyl-1-tetradecyl-. This is hydrolyzed to the corresponding keto-acid (7) which is reduced either with the Wolff-Kishner or Clemmensen reductions (II, step (j)) to give 2,17-dimethyloctadecanoic acid.

EXAMPLE 16

2,5-Dimethylpentadecanoic Acid

The compound is made using the following variations with respect to Example 9:
The alkyl halide is 2-bromododecane in replacement for 2-bromoundecane in Example 9. The Cd intermediate is di(2-dodecyl)cadmium. The product is 2,5-dimethylpentadecanoic acid.

EXAMPLE 17

2,5-Dimethylhexadecanoic Acid

The compound is made using the following variations with respect to Example 9:
The alkyl halide is 2-bromotridecane in replacement for 2-bromoundecane in Example 9. The Cd intermediate is di(2-tridecyl)cadmium. The product is 2,5-dimethylhexadecanoic acid.

EXAMPLE 18

2,5-Dimethyloctadecanoic Acid

The compound is made using the following variations with respect to Example 9:
The alkyl halide is 2-bromopentadecane in replacement for 2-bromoundecane in Example 9. The Cd intermediate is di(2-pentadecyl)cadmium. The product is 2,5-dimethyloctadecanoic acid.

EXAMPLE 19

2,7-Dimethylpentadecanoic Acid

The compound is made using the following variations with respect to Example 10:
The alkyl halide is 2-bromodecane. y=2.

EXAMPLE 20

2,7-Dimethylhexadecanoic Acid

The compound is made using the following variations with respect to Example 10:
The alkyl halide is 2-bromoundecane. y=2.

EXAMPLE 21

2,7-Dimethylheptadecanoic Acid

The compound is made using the following variations with respect to Example 10:
The alkyl halide is 2-bromododecane. y=2.

EXAMPLE 22

2,7-Dimethyloctadecanoic Acid

The compound is made using the following variations with respect to Example 10:
The alkyl halide is 2-bromotridecane. y=2.

EXAMPLE 23

2,9-Dimethylpentadecanoic Acid

Succinic anhydride is opened using methanol (II, step (a)) to give monomethyl succinate (2). This is treated with 2+equivalents of lithium amide in liquid ammonia (II, step (b)) to form its dianion which is alkylated by the addition of one mole of methyl iodide in ether (II, step (c)) and treatment with ammonium chloride (II, step (d)), giving 2-methylsuccinic acid, 1-methyl ester (3). This is treated with thionyl chloride (II, step (e)) to give the corresponding acid chloride (4). Now see GENERAL PROCEDURE I. 1-hexyl bromide (compound (1), R=$CH_3(CH_2)_5$—) is converted to its Grignard reagent with magnesium in dry ether (I, Step (a)). To this is added 5-chloro-2-pentanone (Aldrich C6,2660-3) (I, Step (b)). The reaction mixture is worked up with acetic anhydride (I, Step (c)) to form chloroacetate (3). Acetic acid is eliminated by refluxing (3) in a suitable solvent, e.g., benzene (I, Step (d)) yielding a mixture of chloro-olefin isomers (4) (R=$CH_3(CH_2)_5$—). (4) is converted to its Grignard reagent following standard practice. (I, Step (e)). The Grignard reagent is treated with formaldehyde and aqueous workup (I, Step (m)) and hydrogenated (I, Step (n)), Pd catalyst, and hydrobrominated (I, Step (o)) to give the alkyl bromide (8) (R=$CH_3(CH_2)_5$—, x=4). Now this compound (8) of Procedure I is carried over and used following part of the procedure shown in GENERAL PROCEDURE II, as an alkyl halide and is converted to the Grignard reagent with magnesium (II, Step (f)). The Grignard reagent is converted to a dialkylcadmium (5), di(5-methyl-1-undecyl)cadmium (II, (g)). The dialkylcadmium is reacted (II, step (h)) with the acid chloride of 2-methylsuccinic acid 1-methyl ester (compound (4) prepared supra) yielding compound (6), R=5-methyl-1-undecyl-. This is hydrolyzed to the corresponding keto-acid (7) which is reduced either with the Wolff-Kishner or Clemmensen reductions (II, step (j)) to give 2,9-Dimethylpentadecanoic acid.

EXAMPLE 24

2,9-Dimethylhexadecanoic Acid

Succinic anhydride is opened using methanol (II, step (a)) to give monomethyl succinate (2). This is treated with 2+equivalents of lithium amide in liquid ammonia (II, step (b)) to form its dianion which is alkylated by the addition of one mole of methyl iodide in ether (II, step (c)) and treatment with ammonium chloride (II, step (d)), giving 2-methylsuccinic acid, 1-methyl ester (3). This is treated with thionyl chloride (II, step (e)) to give the corresponding acid chloride (4). Now see GENERAL PROCEDURE I. 1-heptyl bromide (compound (1), R=$CH_3(CH_2)_6$—) is converted to its Grignard reagent with magnesium in dry ether (I, Step (a)). To this is added 5-chloro-2-pentanone (Aldrich C6,2660-3) (I, Step (b)). The reaction mixture is worked up with acetic anhydride (I, Step (c)) to form chloroacetate (3). Acetic acid is eliminated by refluxing (3) in a suitable solvent, e.g., benzene (I, Step (d)) yielding a mixture of chloro-olefin isomers (4) (R=$CH_3(CH_2)_6$—). (4) is converted to its Grignard reagent following standard practice. (I, Step (e)). The Grignard reagent is treated with formaldehyde and aqueous workup (I, Step (m)) and hydrogenated (I, Step (n)), Pd catalyst, and hydrobrominated (I, Step (o)) to give the alkyl bromide (8) (R=$CH_3(CH_2)_6$—, x=4). Now this compound (8) of Procedure I is carried over and used following part of the procedure shown in GENERAL PROCEDURE II, as an alkyl halide and is converted to the Grignard reagent with magnesium (II, Step (f)). The Grignard reagent is converted to a dialkylcadmium (5), di(5-methyl-1-dodecyl)cadmium (II, (g)). The dialkylcadmium is reacted (II, step (h)) with the acid chloride of 2-methylsuccinic acid 1-methyl ester (compound (4) prepared supra) yielding compound (6), R=5-methyl-1-dodecyl-. This is hydrolyzed to the corresponding keto-acid (7) which is reduced either with the Wolff-Kishner or Clemmensen reductions (II, step (j)) to give 2,9-Dimethylhexadecanoic acid.

EXAMPLE 25

2,9-Dimethylheptadecanoic Acid

Succinic anhydride is opened using methanol (II, step (a)) to give monomethyl succinate (2). This is treated with 2+ equivalents of lithium amide in liquid ammonia (II, step (b)) to form its dianion which is alkylated by the addition of one mole of methyl iodide in ether (II, step (c)) and treatment with ammonium chloride (II, step (d)), giving 2-methylsuccinic acid, 1-methyl ester (3). This is treated with thionyl chloride (II, step (e)) to give the corresponding acid chloride (4). Now see GENERAL PROCEDURE I. 1-octyl bromide (compound (1), R=$CH_3(CH_2)_7$—) is converted to its Grignard reagent with magnesium in dry ether (I, Step (a)). To this is added 5-chloro-2-pentanone (Aldrich C6,2660-3) (I, Step (b)). The reaction mixture is worked up with acetic anhydride (I, Step (c)) to form chloroacetate (3). Acetic acid is eliminated by refluxing (3) in a suitable solvent, e.g., benzene (I, Step (d)) yielding a mixture of chloro-olefin isomers (4) (R=$CH_3(CH_2)_7$—). (4) is converted to its Grignard reagent following standard practice. (I, Step (e)). The Grignard reagent is treated with formaldehyde and aqueous workup (I, Step (m)) and hydrogenated (I, Step (n)), Pd catalyst, and hydrobrominated (I, Step (o)) to give the alkyl bromide (8) (R=$CH_3(CH_2)_7$—, x=4). Now this compound (8) of Procedure I is carried over and used following part of the procedure shown in GENERAL PROCEDURE II, as an alkyl halide and is converted to the Grignard reagent with magnesium (II, Step (f)). The Grignard reagent is converted to a dialkylcadmium (5), di(5-methyl-1-tridecyl)cadmium (II, (g)). The dialkylcadmium is reacted (II, step (h)) with the acid chloride of 2-methylsuccinic acid 1-methyl ester (compound (4) prepared supra) yielding compound (6), R=5-methyl-1-tridecyl-. This is hydrolyzed to the corresponding keto-acid (7) which is reduced either with the Wolff-Kishner or Clemmensen reductions (II, step (j)) to give 2,9-dimethyltetradecanoic acid.

EXAMPLE 26

2,11-Dimethylpentadecanoic Acid

Succinic anhydride is opened using methanol (II, step (a)) to give monomethyl succinate (2). This is treated with 2+ equivalents of lithium amide in liquid ammonia (II, step (b)) to form its dianion which is alkylated by the addition of one mole of methyl iodide in ether (II, step (c)) and treatment with ammonium chloride (II, step (d)), giving 2-methylsuccinic acid, 1-methyl ester (3). This is treated with thionyl chloride (II, step (e)) to give the corresponding acid chloride (4). Now see GENERAL PROCEDURE I. 1-butyl bromide (compound (1), R=CH$_3$(CH$_2$)$_3$—) is converted to its Grignard reagent with magnesium in dry ether (I, Step (a)). To this is added 5-chloro-2-pentanone (Aldrich C6,2660-3) (I, Step (b)). The reaction mixture is worked up with acetic anhydride (I, Step (c)) to form chloroacetate (3). Acetic acid is eliminated by refluxing (3) in a suitable solvent, e.g., benzene (I, Step (d)) yielding a mixture of chloro-olefin isomers (4) (R=CH$_3$(CH$_2$)$_3$—). (4) is converted to its Grignard reagent following standard practice. (I, Step (e)). The Grignard reagent is treated with formaldehyde and aqueous workup (I, Step (m)) and hydrogenated (I, Step (n)), Pd catalyst, and hydrobrominated (I, Step (o)) to give the alkyl bromide (8) (R=CH$_3$(CH$_2$)$_3$—, x=4). Now following another part of the procedure shown in GENERAL PROCEDURE I, compound (8) is used instead of compound (4) of Procedure I as an alkyl halide and is converted to the Grignard reagent with magnesium (I, Step (e)). The Grignard reagent is treated with ethylene oxide followed by aqueous acidic workup (I, Step (h)), and hydrobromination (I, Step (j)), to give compound (6) (R=7-methyl-1-undecyl, y=6). Now this compound (6) is used in another part of the procedure shown in GENERAL PROCEDURE II, namely, step (II, (f)) where it is converted to a Grignard reagent. The Grignard reagent is converted to a dialkylcadmium (5), di(7-methyl-1-undecyl)cadmium (II, (g)). The dialkylcadmium is reacted (II, step (h)) with the acid chloride of 2-methylsuccinic acid 1-methyl ester (compound (4) prepared supra) yielding compound (6), R=7-methyl-1-undecyl-. This is hydrolyzed to the corresponding keto-acid (7) which is reduced either with the Wolff-Kishner or Clemmensen reductions (II, step (j)) to give 2,11-dimethylpentadecanoic acid.

EXAMPLE 27

2,1-Dimethylhexadecanoic Acid

Succinic anhydride is opened using methanol (II, step (a)) to give monomethyl succinate (2). This is treated with 2+ equivalents of lithium amide in liquid ammonia (II, step (b)) to form its dianion which is alkylated by the addition of one mole of methyl iodide in ether (II, step (c)) and treatment with ammonium chloride (II, step (d)), giving 2-methylsuccinic acid, 1-methyl ester (3). This is treated with thionyl chloride (II, step (e)) to give the corresponding acid chloride (4). Now see GENERAL PROCEDURE I. 1-pentyl bromide (compound (1), R=CH$_3$(CH$_2$)$_4$—) is converted to its Grignard reagent with magnesium in dry ether (I, Step (a)). To this is added 5-chloro-2-pentanone (Aldrich C6,2660-3) (I, Step (b)). The reaction mixture is worked up with acetic anhydride (I, Step (c)) to form chloroacetate (3). Acetic acid is eliminated by refluxing (3) in a suitable solvent, e.g., benzene (I, Step (d)) yielding a mixture of chloro-olefin isomers (4) (R=CH$_3$(CH$_2$)$_4$—). (4) is converted to its Grignard reagent following standard practice. (I, Step (e)). The Grignard reagent is treated with formaldehyde and aqueous workup (I, Step (m)) and hydrogenated (I, Step (n)), Pd catalyst, and hydrobrominated (I, Step (o)) to give the alkyl bromide (8) (R=CH$_3$(CH$_2$)$_4$—, x=4). Now following another part of the procedure shown in GENERAL PROCEDURE I, compound (8) is used instead of compound (4) of Procedure I as an alkyl halide and is converted to the Grignard reagent with magnesium (I, Step (e)). The Grignard reagent is treated with ethylene oxide followed by aqueous acidic workup (I, Step (h)), and hydrobromination (I, Step (j)), to give compound (6) (R=7-methyl-1-dodecyl, y=6). Now this compound (6) is used in another part of the procedure shown in GENERAL PROCEDURE II, namely, step (II, (f)) where it is converted to a Grignard reagent. The Grignard reagent is converted to a dialkylcadmium (5), di(7-methyl-1-dodecyl)cadmium (II, (g)). The dialkylcadmium is reacted (II, step (h)) with the acid chloride of 2-methylsuccinic acid 1-methyl ester (compound (4) prepared supra) yielding compound (6), R=7-methyl-1-dodecyl-. This is hydrolyzed to the corresponding keto-acid (7) which is reduced either with the Wolff-Kishner or Clemmensen reductions (II, step (j)) to give 2,11-dimethylhexadecanoic acid.

EXAMPLE 28

2,11-Dimethylheptadecanoic Acid

Succinic anhydride is opened using methanol (II, step (a)) to give monomethyl succinate (2). This is treated with 2+ equivalents of lithium amide in liquid ammonia (II, step (b)) to form its dianion which is alkylated by the addition of one mole of methyl iodide in ether (II, step (c)) and treatment with ammonium chloride (II, step (d)), giving 2-methylsuccinic acid, 1-methyl ester (3). This is treated with thionyl chloride (II, step (e)) to give the corresponding acid chloride (4). Now see GENERAL PROCEDURE I. 1-hexyl bromide (compound (1), R=CH$_3$(CH$_2$)$_5$—) is converted to its Grignard reagent with magnesium in dry ether (I, Step (a)). To this is added 5-chloro-2-pentanone (Aldrich C6,2660-3) (I, Step (b)). The reaction mixture is worked up with acetic anhydride (I, Step (c)) to form chloroacetate (3). Acetic acid is eliminated by refluxing (3) in a suitable solvent, e.g., benzene (I, Step (d)) yielding a mixture of chloro-olefin isomers (4) (R=CH$_3$(CH$_2$)$_5$—). (4) is converted to its Grignard reagent following standard practice. (I, Step (e)). The Grignard reagent is treated with formaldehyde and aqueous workup (I, Step (m)) and hydrogenated (I, Step (n)), Pd catalyst, and hydrobrominated (I, Step (o)) to give the alkyl bromide (8) (R=CH$_3$(CH$_2$)$_5$—, x=4). Now following another part of the procedure shown in GENERAL PROCEDURE I, compound (8) is used instead of compound (4) of Procedure I as an alkyl halide and is converted to the Grignard reagent with magnesium (I, Step (e)). The Grignard reagent is treated with ethylene oxide followed by aqueous acidic workup (I, Step (h)), and hydrobromination (I, Step (j)), to give compound (6) (R=7-methyl-1-tridecyl, y=6). Now this compound (6) is used in another part of the procedure shown in GENERAL PROCEDURE II, namely, step (II, (f)) where it is converted to a Grignard reagent. The Grignard reagent is converted to a dialkylcadmium (5), di(7-methyl-1-tridecyl)cadmium (II, (g)). The dialkylcadmium is reacted (II, step (h)) with the acid chloride of 2-methylsuccinic acid 1-methyl ester (compound (4) prepared supra) yielding compound (6), R=7-methyl-1-tridecyl-. This is hydrolyzed to the corresponding keto-acid (7) which is reduced either with the Wolff-Kishner or Clemmensen reductions (II, step (j)) to give 2,11-dimethylheptadecanoic acid.

EXAMPLE 29

2,11-Dimethyloctadecanoic Acid

Succinic anhydride is opened using methanol (II, step (a)) to give monomethyl succinate (2). This is treated with 2+equivalents of lithium amide in liquid ammonia (II, step (b)) to form its dianion which is alkylated by the addition of one mole of methyl iodide in ether (II, step (c)) and treatment with ammonium chloride (II, step (d)), giving 2-methylsuccinic acid, 1-methyl ester (3). This is treated with thionyl chloride (II, step (e)) to give the corresponding acid chloride (4). Now see GENERAL PROCEDURE I. 1-heptyl bromide (compound (1), R=$CH_3(CH_2)_6$—) is converted to its Grignard reagent with magnesium in dry ether (I, Step (a)). To this is added 5-chloro-2-pentanone (Aldrich C6,2660-3) (I, Step (b)). The reaction mixture is worked up with acetic anhydride (I, Step (c)) to form chloroacetate (3). Acetic acid is eliminated by refluxing (3) in a suitable solvent, e.g., benzene (I, Step (d)) yielding a mixture of chloro-olefin isomers (4) (R=$CH_3(CH_2)_6$—). (4) is converted to its Grignard reagent following standard practice. (I, Step (e)). The Grignard reagent is treated with formaldehyde and aqueous workup (I, Step (m)) and hydrogenated (1, Step (n)), Pd catalyst, and hydrobrominated (I, Step (o)) to give the alkyl bromide (8) (R=$CH_3(CH_2)_6$—, x=4). Now following another part of the procedure shown in GENERAL PROCEDURE I, compound (8) is used instead of compound (4) of Procedure I as an alkyl halide and is converted to the Grignard reagent with magnesium (I, Step (e)). The Grignard reagent is treated with ethylene oxide followed by aqueous acidic workup (I, Step (h)), and hydrobromination (I, Step (j)), to give compound (6) (R=7-methyl-1-tetradecyl, y=6). Now this compound (6) is used in another part of the procedure shown in GENERAL PROCEDURE II, namely, step (II, (f)) where it is converted to a Grignard reagent. The Grignard reagent is converted to a dialkylcadmium (5), di(7-methyl-1-tetradecyl)cadmium (II, (g)). The dialkylcadmium is reacted (II, step (h)) with the acid chloride of 2-methylsuccinic acid 1-methyl ester (compound (4) prepared supra) yielding compound (6), R=7-methyl-1-tetradecyl-. This is hydrolyzed to the corresponding keto-acid (7) which is reduced either with the Wolff-Kishner or Clemmensen reductions (II, step (j)) to give 2,11-dimethyloctadecanoic acid.

EXAMPLE 30

2,13-Dimethylpentadecanoic Acid

The procedure is as described in Example 13 except that Ethyl Bromide replaces Methyl iodide in Step Ia.

EXAMPLE 31

2,13-Dimethylhexadecanoic Acid

The procedure is as described in Example 13 except that 1-propyl Bromide replaces Methyl iodide in Step Ia.

EXAMPLE 32

2,13-Dimethylheptadecanoic Acid

The procedure is as described in Example 13 except that 1-butyl Bromide replaces Methyl iodide in Step Ia.

EXAMPLE 33

2,13-Dimethyloctadecanoic Acid

The procedure is as described in Example 13 except that 1-pentyl Bromide replaces Methyl iodide in Step Ia.

EXAMPLE 34

2,15-Dimethylheptadecanoic Acid

The procedure is as described in Example 14 except that Ethyl Bromide replaces Methyl iodide in Step Ia.

EXAMPLE 35

2,15-Dimethyloctadecanoic Acid

The procedure is as described in Example 14 except that 1-propyl Bromide replaces Methyl iodide in Step Ia.

EXAMPLE 36

2-ethyl-5-methyltetradecanoic Acid

The procedure is as described in Example 9 except that Ethyl Bromide replaces Methyl Iodide.

EXAMPLE 37

2-ethyl-7-methyltetradecanoic acid The procedure is as described in Example 10 except that Ethyl Bromide replaces Methyl Iodide in step (h).

EXAMPLE 38

2-ethyl-9-methyltetradecanoic Acid

The procedure is as described in Example 11 except that Ethyl Bromide replaces Methyl Iodide.

EXAMPLE 39

2-ethyl-11-methyltetradecanoic Acid

The procedure is as described in Example 12 except that Ethyl Bromide replaces Methyl Iodide.

EXAMPLE 40

2-ethyl-13-methyltetradecanoic Acid

The procedure is as described in Example 13 except that Ethyl Bromide replaces Methyl Iodide.

EXAMPLE 41

2-ethyl-5-methyltridecanoic Acid

The procedure is as described in Example 9 except that Ethyl Bromide replaces Methyl Iodide and 2-bromodecane replaces 2-bromoundecane.

EXAMPLE 42

2-ethyl-7-methyltridecanoic Acid

The procedure is as described in Example 10 except that Ethyl Bromide replaces Methyl Iodide in step (h) and 2-octyl bromide replaces 2-nonyl bromide.

EXAMPLE 43

2-ethyl-9-methyltridecanoic Acid

The procedure is as described in Example 11 except that Ethyl Bromide replaces Methyl Iodide and 1-bromobutane replaces 1-pentyl bromide.

EXAMPLE 44

2-ethyl-11-methyltridecanoic Acid

The procedure is as described in Example 12 except that Ethyl Bromide replaces Methyl Iodide in procedure II step (c) and ethyl bromide also replaces 1-propyl bromide in procedure I step (a).

EXAMPLE 45

2-ethyl-6-methyltetradecanoic Acid

The procedure used is that of GENERAL PROCEDURE III except that 2-bromodecane is used as compound (1) in step (a), formaldehyde is used in place of ethylene oxide in step (b), y=1, and ethyl bromide is used in place of methyl iodide in step (h).

EXAMPLE 46

2-ethyl-6-methyltridecanoic Acid

The procedure used is that of GENERAL PROCEDURE III except that 2-bromononane is used as compound (1) in step (a), formaldehyde is used in place of ethylene oxide in step (b), y=1, and ethyl bromide is used in place of methyl iodide in step (h).

EXAMPLE 47

2-ethyl-8-methyltetradecanoic Acid

The procedure used is that of GENERAL PROCEDURE IV. j=5, k=1.

EXAMPLE 48

2-ethyl-8-methyltridecanoic Acid

The procedure used is that of GENERAL PROCEDURE IV. j=4, k=1.

EXAMPLE 49

2-ethyl-10-methyltetradecanoic Acid

The procedure used is that of GENERAL PROCEDURE IV. j=3, k=2.

EXAMPLE 50

7,8-dimethyltridecanoic Acid

The procedure used is that of GENERAL PROCEDURE V. x=4, y=2.

EXAMPLE 51

7,8-dimethylpentadecanoic Acid

The procedure used is that of GENERAL PROCEDURE V. x=6, y=2.

EXAMPLE 52

9,10-dimethylpentadecanoic Acid

The procedure used is that of GENERAL PROCEDURE V. x=4, y=4.

EXAMPLE 53

9,10-dimethylheptadecanoic Acid

The procedure used is that of GENERAL PROCEDURE V. x=6, y=4.

EXAMPLE 54

8,9-dimethylpentadecanoic Acid

The procedure used is that of GENERAL PROCEDURE VI. x=5, y=3.

EXAMPLE 55

2-propyl-5-methyltridecanoic Acid

The procedure is as described in Example 9 except that Propyl Bromide replaces Methyl Iodide and 2-bromodecane replaces 2-bromoundecane.

EXAMPLE 56

2-propyl-7-methyltridecanoic Acid

The procedure is as described in Example 10 except that Propyl Bromide replaces Methyl Iodide and 2-Bromooctane replaces 2-bromononane. y=2.

EXAMPLE 57

2-propyl-9-methyltridecanoic Acid

The procedure is as described in Example 11 except that Propyl Bromide replaces Methyl Iodide in step (c) of GENERAL PROCEDURE II and 1-butyl bromide replaces 1-pentyl bromide in step (a) of GENERAL PROCEDURE I.

EXAMPLE 58

2-propyl-11-methyltridecanoic Acid

The procedure is as described in Example 12 except that Propyl Bromide replaces Methyl Iodide in Step IIc and ethyl bromide replaces 1-propyl bromide in step Ia.

EXAMPLE 59

2-propyl-5-methyldodecanoic Acid

The procedure is as described in Example 9 except that Propyl Bromide replaces Methyl Iodide and 2-bromononane replaces 2-bromoundecane.

EXAMPLE 60

2-propyl-7-methyldodecanoic Acid

The procedure is as described in Example 10 except that Propyl Bromide replaces Methyl Iodide and 2-bromoheptane replaces 2-bromononane. y=2.

EXAMPLE 61

2-propyl-9-methyldodecanoic Acid

The procedure is as described in Example 11 except that Propyl Bromide replaces Methyl Iodide in step IIc and 1-propyl bromide replaces 1-pentyl bromide in step Ia.

EXAMPLE 62

2-propyl-1-methyldodecanoic Acid

The procedure is as described in Example 12 except that Propyl Bromide replaces Methyl Iodide in step IIc and methyl iodide replaces 1-propyl bromide in step Ia.

EXAMPLE 63

2-propyl-6-methyltridecanoic Acid

The procedure used is that of GENERAL PROCEDURE III except that 2-bromononane is used as compound (1) in step (a), formaldehyde is used in place of ethylene oxide in step (b), y=1, and propyl bromide is used in place of methyl iodide in step (h).

EXAMPLE 64

2-propyl-6-methyldodecanoic Acid

The procedure used is that of GENERAL PROCEDURE III except that 2-bromooctane is used as compound (1) in step (a), formaldehyde is used in place of ethylene oxide in step (b), y=1, and propyl bromide is used in place of methyl iodide in step (h).

EXAMPLE 65

2-propyl-8-methyltridecanoic Acid

The procedure used is that of GENERAL PROCEDURE IV. j=4, k=1 and 1-propyl bromide replaces ethyl bromide.

EXAMPLE 66

2-propyl-8-methyldodecanoic Acid

The procedure used is that of GENERAL PROCEDURE IV. j=3, k=1 and 1-propyl bromide replaces ethyl bromide.

EXAMPLE 67

2-propyl-10-methyltridecanoic Acid

The procedure used is that of GENERAL PROCEDURE IV. j=2, k=2 and 1-propyl bromide replaces ethyl bromide.

EXAMPLE 68

2-propyl-10-methyldodecanoic Acid

The procedure used is that of GENERAL PROCEDURE IV. j=1, k=2 and 1-propyl bromide replaces ethyl bromide.

EXAMPLE 69

6,7-dimethylundecanoic Acid

The procedure used is that of GENERAL PROCEDURE VII starting with 2-bromohexane; x=3, y=1.

EXAMPLE 70

9-ethyltridecanoic Acid

Following General Procedure VIII use ethyl bromide in step (c) ($Z=CH_3CH_2$—) and use ethyl bromide in step (f) ($R=CH_3CH_2$—) to eventually obtain 2-ethyl-1-hexanol as compound (9). This is converted to its bromide in step (1) and to its Grignard reagent in step (m). Following the sequence (n–1), (o), (p), (n–1), (o), (p), (n–1), (o), (p) (that is, three iterations of ethylene oxide) gives final Grignard reagent (12), x=7, R=Et, Z=Et which with $CO_2$ treatment gives 9-ethyltridecanoic acid (13) (x=7, R=Et, Z=Et).

EXAMPLE 71

9-propyldodecanoic Acid

Following General Procedure VIII use 1-bromopropane in step (c) ($Z=CH_3(CH_2)_2$—) and use methyl bromide in step (f) ($R=CH_3$—) to eventually obtain 2-propyl-1-pentanol as compound (9). This is converted to its bromide in step (I) and to its Grignard reagent in step (m). Following the sequence (n–1), (o), (p), (n–1), (o), (p), (n–1), (o), (p) (that is, three iterations of ethylene oxide) gives final Grignard reagent (12), x=7, R=Me, Z=n-Pr which with $CO_2$ treatment gives 9-propyldodecanoic acid (13) (x=7, R=Me, Z=n-Pr).

EXAMPLE 72

9-ethylpentadecanoic Acid

Following General Procedure VIII use ethyl bromide in step (c) ($Z=CH_3CH_2$—) and use 1-bromobutane in step (f) ($R=CH_3(CH_2)_3$—) to eventually obtain 2-ethyl-1-octanol as compound (9). This is converted to its bromide in step (1) and to its Grignard reagent in step (m). Following the sequence (n–1), (o), (p), (n–1), (o), (p), (n–1), (o), (p) (that is, three iterations of ethylene oxide) gives final Grignard reagent (12), x=7, R=n-Bu, Z=Et which with $CO_2$ treatment gives 9-ethylpentadecanoic acid (13) (x=7, R=n-Bu, Z=Et).

EXAMPLE 73

9-propyltetradecanoic Acid

Following General Procedure VIII use 1-bromopropane in step (c) ($Z=CH_3(CH_2)_2$—) and use 1-bromopropane in step (f) ($R=CH_3(CH_2)_2$—) to eventually obtain 2-propyl-1-octanol as compound (9). This is converted to its bromide in step (I) and to its Grignard reagent in step (m). Following the sequence (n–1), (o), (p), (n–1), (o), (p), (n–1), (o), (p) (that is, three iterations of ethylene oxide) gives final Grignard reagent (12), x=7, R=n-Pr, Z=n-Pr which with $CO_2$ treatment gives 9-propyltetradecanoic acid (13) (x=7, R=n-Pr, Z=n-Pr).

EXAMPLE 74

7-propyltetradecanoic Acid

Following General Procedure VIII use 1-bromopropane in step (c) ($Z=CH_3(CH_2)_2$—) and use 1-bromopentane in step (f) ($R=CH_3(CH_2)_4$—) to eventually obtain 2-propyl-1-nonanol as compound (9). This is converted to its bromide in step (1) and to its Grignard reagent in step (m). Following the sequence (n–1), (o), (p), (n–1), (o), (p), (that is, two iterations of ethylene oxide) gives final Grignard reagent (12), x=5, R=n-pentyl, Z=n-Pr which with $CO_2$ treatment gives 7-propyltetradecanoic acid (13) (x=5, R=n-pentyl, Z=n-Pr).

EXAMPLE 75

7-ethylpentadecanoic Acid

Following General Procedure VIII use ethyl bromide in step (c) ($Z=CH_3CH_2$—) and use 1-bromohexane in step (f) ($R=CH_3(CH_2)_5$—) to eventually obtain 2-ethyl-1-decanol as compound (9). This is converted to its bromide in step (1) and to its Grignard reagent in step (m). Following the sequence (n–1), (o), (p), (n–1), (o), (p), (that is, two iterations of ethylene oxide) gives final Grignard reagent (12), x=5, R=n-hexyl, Z=Et which with $CO_2$ treatment gives 7-ethylpentadecanoic acid (13) (x=5, R=n-hexyl, Z=Et).

EXAMPLE 76

5-propyldodecanoic Acid

Following General Procedure VIII use 1-bromopropane in step (c) ($Z=CH_3(CH_2)_2$—) and use 1-bromopentane in step (f) ($R=CH_3(CH_2)_4$—) to eventually obtain 2-propyl-1-nonanol as compound (9). This is converted to its bromide in step (l) and to its Grignard reagent in step (m). Following the sequence (n–1), (o), (p) gives final Grignard reagent (12), x=3, R=n-pentyl, Z=n-Pr which with $CO_2$ treatment gives 5-propyldodecanoic acid (13) (x=3, R=n-pentyl, Z=n-Pr).

EXAMPLE 77

6-ethyltridecanoic Acid

Following General Procedure VIII use ethyl bromide in step (c) (Z=$CH_3CH_2$—) and use 1-bromopentane in step (f) (R=$CH_3(CH_2)_4$—) to eventually obtain 2-ethyl-1-nonanol as compound (9). This is converted to its bromide in step (l) and to its Grignard reagent in step (m). Following the sequence (n–1), (o), (p), (n–2), (o), (p) (that is, one ethylene oxide iteration and one formaldehyde iteration) gives final Grignard reagent (12), x=4, R=n-pentyl, Z=Et which with $CO_2$ treatment gives 6-ethyltridecanoic acid (13) (x=4, R=n-pentyl, Z=Et).

EXAMPLE 78

Sodium Soaps 10 mmol of fatty acid is added to about 10.2 mmol of sodium hydroxide predissolved in 100 ml of methanol. A little water may optionally be present. The methanol is evaporated to give the soap. The sodium soap is made in this way for each one of the preceding fatty acids listed above.

EXAMPLE 79

Potassium Soaps 10 mmol of fatty acid is added to about 10.2 mmol of potassium hydroxide predissolved in 100 ml of methanol. A little water may optionally be present. The methanol is evaporated to give the soap. The potassium soap is made in this way for each one of the preceding fatty acids listed above.

EXAMPLE 80

Ammonium Soaps 10 mmol of fatty acid is added to about 10.2 mmol of ammonia (used as concentrated aqueous reagent) predissolved in 100 ml of methanol. The solvent is evaporated to give the soap. The ammonium soap is made in this way for each one of the preceding fatty acids listed above.

EXAMPLE 81

Calcium Soaps

Sodium Soap made as per Example 78 (10 mmol) is dissolved in water and treated slowly with stirring with 5 mmol of Calcium Chloride as a 10% aqueous solution.

The resulting slurry is filtered, washed and dried. The calcium soap is made in this way for each one of the preceding fatty acids listed above.

EXAMPLE 82

Magnesium Soaps

Sodium Soap made as per Example 78 (10 mmol) is dissolved in water and treated slowly with stirring with 5 mmol of Magnesium Chloride as a 10% aqueous solution.

The resulting slurry is filtered, washed and dried. The magnesium soap is made in this way for each one of the preceding fatty acids listed above.

INDUSTRIAL APPLICABILITY

The compositions, e.g., the various novel fatty acids and salts of the type herein can be used in all manner of compositions. Detergent compositions of the invention may also contain additional detergent components. The precise nature of these additional components, and levels of incorporation thereof will depend on the physical form of the cleaning composition, and the precise nature of the cleaning operation for which it is to be used. Cleaning compositions herein include, but are not limited to: granular, bar-form and liquid laundry detergents; liquid hand dishwashing compositions; liquid, gel and bar-form personal cleansing products; shampoos; dentifrices; hard surface cleaners, and the like. Such compositions can contain a variety of conventional detersive ingredients.

The compositions, e.g., the various novel fatty acids and salts of the type herein can be used in all manner of skin care compositions. The precise nature of these additional components, and levels of incorporation thereof will depend on the physical form of the skin care composition, and the precise nature of the skin care operation for which it is to be used.

The following listing of such ingredients is for the convenience of the formulator, and not by way of limitation of the types of ingredients which can be used with the branched-chain surfactants herein. The cleaning compositions of the invention preferably contain one or more conventional detergent additives for example surfactants, builders, alkalinity system, organic polymeric compounds, suds suppressors, soil suspension and anti-redeposition agents and corrosion inhibitors. The skin care compositions of the invention preferably contain one or more conventional skin care additives, for example, fragrances, emollients, anti-acne actives, thickeners, structuring agents and skin conditioners.

Conventional Detergent Additives

Detersive Surfactants:

The detergent compositions according to the present invention preferably further comprise additional surfactants, herein also referred to as co-surfactants. It is to be understood that the branched-chain surfactants prepared in the manner of the present invention may be used singly in cleaning compositions or in combination with other detersive surfactants. Typically, fully-formulated cleaning compositions will contain a mixture of surfactant types in order to obtain broad-scale cleaning performance over a variety of soils and stains and under a variety of usage conditions. One advantage of the branched-chain surfactants herein is their ability to be readily formulated in combination with other known surfactant types.

A wide range of these co-surfactants can be used in the detergent compositions of the present invention. A typical listing of anionic, nonionic, cationic, ampholytic and zwitterionic classes, and species of these co-surfactants, is given in U.S. Pat. No. 3,664,961 issued to Norris on May 23, 1972. Amphoteric surfactants are also described in detail in "Amphoteric Surfactants, Second Edition", E. G. Lomax, Editor (published 1996, by Marcel Dekker, Inc.) McCutcheon's, Emulsifiers and Detergents, Annually published by M. C. Publishing Co., and Surface Active Agents and Detergents" (Vol. I and II by Schwartz, Perry and Berch), which are incorporated herein by reference.

The laundry detergent compositions of the present invention typically comprise from about 0.1% to about 50%, preferably from about 0.5% to about 35%, more preferably 0.5% to about 30%, by weight of co-surfactants. Selected co-surfactants are further identified as follows.

Anionic Co-surfactants—Nonlimiting examples of anionic co-surfactants useful herein, typically at levels from about 0.1% to about 50%, by weight, include the conventional $C_{11}$–$C_{18}$ alkyl benzene sulfonates ("LAS") and primary, branched-chain and random $C_{10}$–$C_{20}$ alkyl sulfates ("AS"), the $C_{10}$–$C_{18}$ secondary (2,3) alkyl sulfates of the formula $CH_3(CH_2)_x(CHOSO_3^-M^+)CH_3$ and $CH_3(CH_2)_y(CHOSO_3^-M^+)CH_2CH_3$ where x and (y+1) are integers of at least about 7, preferably at least about 9, and M is a water-solubilizing cation, especially sodium, unsaturated sulfates such as oleyl sulfate, the $C_{10}$–$C_{18}$ alpha-sulfonated fatty acid esters, the $C_{10}$–$C_{18}$ sulfated alkyl polyglycosides, the $C_{10}$–$C_{18}$ alkyl alkoxy sulfates ("AE$_x$S"; especially EO 1–7 ethoxy sulfates), and $C_{10}$–$C_{18}$ alkyl alkoxy carboxylates (especially the EO 1–5 ethoxycarboxylates). The $C_{12}$–$C_{18}$ betaines and sulfobetaines ("sultaines"), $C_{10}$–$C_{18}$ amine oxides, and the like, can also be included in the overall compositions. $C_{10}$–$C_{20}$ conventional soaps may also be used. Other conventional useful anionic co-surfactants are listed in standard texts.

The alkyl alkoxy sulfate surfactants useful herein are preferably water soluble salts or acids of the formula $RO(A)_mSO_3M$ wherein R is an unsubstituted $C_{10}$–$C_{24}$ alkyl or hydroxyalkyl group having a $C_{10}$–$C_{24}$ alkyl component, preferably a $C_{12}$–$C_{18}$ alkyl or hydroxyalkyl, more preferably $C_{12}$–$C_{15}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation, ammonium or substituted-ammonium cation. Alkyl ethoxylated sulfates as well as alkyl propoxylated sulfates are contemplated herein.

The alkyl sulfate surfactants useful herein are preferably water soluble salts or acids of the formula $ROSO_3M$ wherein R preferably is a $C_{10}$–$C_{24}$ hydrocarbyl, preferably an alkyl or hydroxyalkyl having a $C_{10}$–$C_{18}$ alkyl component, more preferably a $C_{12}$–$C_{15}$ alkyl or hydroxyalkyl, and M is H or a cation, e.g., an alkali metal cation (e.g. sodium, potassium, lithium), or ammonium or substituted ammonium.

Other suitable anionic surfactants that can be used are alkyl ester sulfonate surfactants including linear esters of $C_8$–$C_{20}$ carboxylic acids (i.e., fatty acids) which are sulfonated with gaseous $SO_3$ according to "The Journal of the American Oil Chemists Society", 52 (1975), pp. 323–329. Suitable starting materials would include natural fatty substances as derived from tallow, palm oil, etc.

Other anionic co-surfactants useful for detersive purposes can also be included in the laundry detergent compositions of the present invention. These can include salts of soap, $C_8$–$C_{22}$ primary of secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl glycerol sulfonates, fatty acyl glycerol sulfonates, fatty oleoyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated $C_{12}$–$C_{18}$ monoesters) and diesters of sulfosuccinates (especially saturated and unsaturated $C_6$–$C_{12}$ diesters), sulfates of alkylpolysaccharides such as the sulfates of alkylpolyglucoside (the nonionic nonsulfated compounds being described below), and alkyl polyethoxy carboxylates such as those of the formula $RO(CH_2CH_2O)_k$—$CH_2COO$-M+ wherein R is a $C_8$–$C_{22}$ alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil. A variety of such surfactants are also generally disclosed in U.S. Pat. No. 3,929,678, issued Dec. 30, 1975 to Laughlin, et al. at Column 23, line 58 through Column 29, line 23 (herein incorporated by reference).

Another possible surfactant are the so-called Dianionics. These are surfactants which have at least two anionic groups present on the surfactant molecule. Some suitable dianionic surfactants are further described in copending U.S. Serial Nos. 60/020,503, 60/020,772, 60/020,928, 60/020,832 and 60/020,773 all filed on Jun. 28, 1996, and 60/023,539, 60/023,493, 60/023,540 and 60/023,527 filed on Aug. 8, 1996, the disclosures of which are incorporated herein by reference. Other conventional useful surfactants are listed in standard texts.

Additionally, the surfactant may be a branched alkyl sulfate, branched alkyl alkoxylate, branched alkyl alkoxylate sulfate or mid chain branched alkyl aryl sulfonate. These Surfactants are further described in copending U.S. Patent applications No. 60/053,319 filed on Jul. 21, 1997, No. 60/053,318, filed on Jul. 21, 1997, No. 60/053,321, filed on Jul. 21, 1997, No. 60/053,209, filed on Jul. 21, 1997, No. 60/053,328, filed on Jul. 21, 1997, No. 60/053,186, filed on Jul. 21, 1997, No. 60/061,971, Oct. 14, 1997, No. 60/061, 975, Oct. 14, 1997, No. 60/062,086, Oct. 14, 1997, No. 60/061,916, Oct. 14, 1997, No. 60/061,970, Oct. 14, 1997, No. 60/062,407, Oct. 14, 1997. Other suitable mid-chain branched surfactants can be found in U.S. patent applications Ser. Nos. 60/032,035, 60/031,845, 60/031,916, 60/031, 917, 60/031,761, 60/031,762 and 60/031,844. Mixtures of these branched surfactants with conventional linear surfactants are also suitable for use in the present compositions. Nonionic Co-surfactants—Nonlimiting examples of nonionic co-surfactants useful herein typically at levels from about 0.1% to about 50%, by weight include the alkoxylated alcohols (AE's) and alkyl phenols, polyhydroxy fatty acid amides (PFAA's), alkyl polyglycosides (APG's), $C_{10}$–$C_{18}$ glycerol ethers, and the like.

More specifically, the condensation products of primary and secondary aliphatic alcohols with from about 1 to about 25 moles of ethylene oxide (AE) are suitable for use as the nonionic surfactant in the present invention. The alkyl chain of the aliphatic alcohol can either be straight or branched, primary or secondary, and generally contains from about 8 to about 22 carbon atoms. Preferred are the condensation products of alcohols having an alkyl group containing from about 8 to about 20 carbon atoms, with from about 1 to about 10 moles of ethylene oxide per mole of alcohol. Especially preferred nonionic surfactants of this type are the $C_9$–$C_{15}$ primary alcohol ethoxylates containing 3–12 moles of ethylene oxide per mole of alcohol, particularly the $C_{12}$–$C_{15}$ primary alcohols containing 5–10 moles of ethylene oxide per mole of alcohol.

Examples of commercially available nonionic surfactants of this type include: Tergitol™ 15-S-9 (the condensation product of $C_{11}$–$C_{15}$ linear alcohol with 9 moles ethylene oxide) and Tergitol™ 24-L-6 NMW (the condensation product of $C_{12}$–$C_{14}$ primary alcohol with 6 moles ethylene oxide with a narrow molecular weight distribution), both marketed by Union Carbide Corporation; Neodol™ 45-9 (the condensation product of $C_{14}$–$C_{15}$ linear alcohol with 9 moles of ethylene oxide), Neodol™ 23-3 (the condensation product of $C_{12}$–$C_{13}$ linear alcohol with 3 moles of ethylene oxide), Neodol™ 45-7 (the condensation product of $C_{14}$–$C_{15}$ linear alcohol with 7 moles of ethylene oxide) and Neodol™ 45-5 (the condensation product of $C_{14}$–$C_{15}$ linear alcohol with 5 moles of ethylene oxide) marketed by Shell Chemical Company; Kyro™ EOB (the condensation product of $C_{13}$–$C_{15}$ alcohol with 9 moles ethylene oxide), marketed by The Procter & Gamble Company; and Genapol LA O3O or O5O (the condensation product of $C_{12}$–$C_{14}$ alcohol with 3 or 5 moles of ethylene oxide) marketed by Hoechst. The preferred range of HLB in these AE nonionic surfactants is from 8–17 and most preferred from 8–14. Condensates with propylene oxide and butylene oxides may also be used.

Another class of preferred nonionic co-surfactants for use herein are the polyhydroxy fatty acid amide surfactants of the formula.

wherein $R^1$ is H, or $C_{1-4}$ hydrocarbyl, 2-hydroxy ethyl, 2-hydroxy propyl or a mixture thereof, $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. Preferably, $R^1$ is methyl, $R^2$ is a straight $C_{11-15}$ alkyl or $C_{15-17}$ alkyl or alkenyl chain such as coconut alkyl or mixtures thereof, and Z is derived from a reducing sugar such as glucose, fructose, maltose, lactose, in a reductive amination reaction. Typical examples include the $C_{12}$–$C_{18}$ and $C_{12}$–$C_{14}$ N-methylglucamides. See U.S. Pat. Nos. 5,194,639 and 5,298,636. N-alkoxy polyhydroxy fatty acid amides can also be used; see U.S. Pat. No. 5,489,393.

Also useful as a nonionic co-surfactant in the present invention are the alkylpolysaccharides such as those disclosed in U.S. Pat. No. 4,565,647, Llenado, issued Jan. 21, 1986, and EP-Patents B 0 070 077, 0 075 996 and 0 094 118.

Polyethylene, polypropylene, and polybutylene oxide condensates of alkyl phenols are also suitable for use as the nonionic surfactant of the surfactant systems of the present invention, with the polyethylene oxide condensates being preferred. These compounds include the condensation products of alkyl phenols having an alkyl group containing from about 6 to about 14 carbon atoms, preferably from about 8 to about 14 carbon atoms, in either a straight-chain or branched-chain configuration with the alkylene oxide. In a preferred embodiment, the ethylene oxide is present in an amount equal to from about 2 to about 25 moles of ethylene oxide per mole of alkyl phenol. Commercially available nonionic surfactants of this type include Igepal™ CO-630, marketed by the GAF Corporation; and Triton™ X-45, X-114, X-100 and X-102, all marketed by the Rohm & Haas Company. These surfactants are commonly referred to as alkylphenol alkoxylates (e.g., alkyl phenol ethoxylates). Examples of other suitable nonionic surfactants are the commercially-available Pluronic™ surfactants, marketed by BASF, the commercially available Tetronic™ compounds, marketed by BASF.

Also preferred nonionics are amine oxide surfactants. The compositions of the present invention may comprise amine oxide in accordance with the general formula I:

$$R^1(EO)_x(PO)_y(BO)_zN(O)(CH_2R')_2 \cdot qH_2O \qquad (I).$$

In general, it can be seen that the structure (I) provides one long-chain moiety $R^1(EO)_x(PO)_y(BO)_z$ and two short chain moieties, $CH_2R'$. R' is preferably selected from hydrogen, methyl and —$CH_2OH$. In general $R^1$ is a primary or branched hydrocarbyl moiety which can be saturated or unsaturated, preferably, $R^1$ is a primary alkyl moiety. When $x+y+z=0$, $R^1$ is a hydrocarbyl moiety having chainlength of from about 8 to about 18. When $x+y+z$ is different from 0, $R^1$ may be somewhat longer, having a chainlength in the range $C_{12}$–$C_{24}$. The general formula also encompasses amine oxides wherein $x+y+z=0$, $R_1=C_8$–$C_{18}$, R'=H and $q=0-2$, preferably 2. These amine oxides are illustrated by $C_{12-14}$ alkyldimethyl amine oxide, hexadecyl dimethylamine oxide, octadecylamine oxide and their hydrates, especially the dihydrates as disclosed in U.S. Pat. Nos. 5,075,501 and 5,071,594, incorporated herein by reference.

Highly preferred amine oxides herein are solutions at ambient temperature. Amine oxides suitable for use herein are made commercially by a number of suppliers, including Akzo Chemie, Ethyl Corp., and Procter & Gamble. See McCutcheon's compilation and Kirk-Othmer review article for alternate amine oxide manufacturers.

Whereas in certain of the preferred embodiments R' is H, there is some latitude with respect to having R' slightly larger than H. Specifically, the invention further encompasses embodiments wherein R' is $CH_2OH$, such as hexadecylbis(2-hydroxyethyl)amine oxide, tallowbis(2-hydroxyethyl)amine oxide, stearylbis(2-hydroxyethyl) amine oxide and oleylbis(2-hydroxyethyl)amine oxide, dodecyldimethylamine oxide dihydrate.

Cationic Co-surfactants—Nonlimiting examples of cationic co-surfactants useful herein typically at levels from about 0.1% to about 50%, by weight include the choline ester-type quats and alkoxylated quaternary ammonium (AQA) surfactant compounds, and the like.

Cationic co-surfactants useful as a component of the surfactant system is a cationic choline ester-type quat surfactant which are preferably water dispersible compounds having surfactant properties and comprise at least one ester (i.e. —COO—) linkage and at least one cationically charged group. Suitable cationic ester surfactants, including choline ester surfactants, have for example been disclosed in U.S. Pat. Nos. 4,228,042, 4,239,660 and 4,260,529.

Preferred cationic ester surfactants are those having the formula:

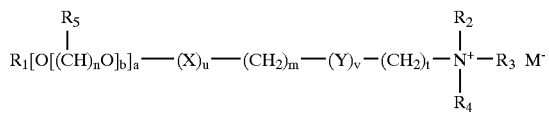

wherein $R_1$ is a $C_5$–$C_{31}$ linear or branched alkyl, alkenyl or alkaryl chain or $M^- \cdot N^+(R_6R_7R_8)(CH_2)_S$; X and Y, independently, are selected from the group consisting of COO, OCO, O, CO, OCOO, CONH, NHCO, OCONH and NHCOO wherein at least one of X or Y is a COO, OCO, OCOO, OCONH or NHCOO group; $R_2$, $R_3$, $R_4$, $R_6$, $R_7$ and $R_8$ are independently selected from the group consisting of alkyl, alkenyl, hydroxyalkyl, hydroxyalkenyl and alkaryl groups having from 1 to 4 carbon atoms; and $R_5$ is independently H or a $C_1$–$C_3$ alkyl group; wherein the values of m, n, s and t independently lie in the range of from 0 to 8, the value of b lies in the range from 0 to 20, and the values of a, u and v independently are either 0 or 1 with the proviso that at least one of u or v must be 1; and wherein M is a counter anion.

Preferably $R_2$, $R_3$ and $R_4$ are independently selected from $CH_3$ and —$CH_2CH_2OH$.

Preferably M is selected from the group consisting of halide, methyl sulfate, sulfate, and nitrate, more preferably methyl sulfate, chloride, bromide or iodide.

Preferred water dispersible cationic ester surfactants are the choline esters having the formula:

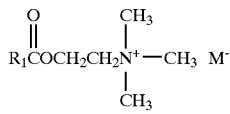

wherein $R_1$ is a $C_{11}$–$C_{19}$ linear or branched alkyl chain.

Other suitable cationic ester surfactants have the structural formulas below, wherein d may be from 0 to 20.

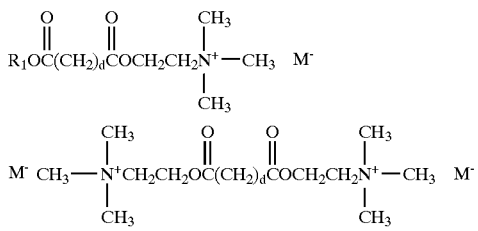

In a preferred aspect these cationic ester surfactant are hydrolysable under the conditions of a laundry wash method.

Cationic co-surfactants useful herein also include alkoxylated quaternary ammonium (AQA) surfactant compounds (referred to hereinafter as "AQA compounds") having the formula:

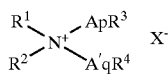
I wherein $R^1$ is a linear or branched alkyl or alkenyl moiety containing from about 8 to about 18 carbon atoms, preferably 10 to about 16 carbon atoms, most preferably from about 10 to about 14 carbon atoms; $R^2$ is an alkyl group containing from one to three carbon atoms, preferably methyl; $R^3$ and $R^4$ can vary independently and are selected from hydrogen (preferred), methyl and ethyl; $X^-$ is an anion such as chloride, bromide, methylsulfate, sulfate, or the like, sufficient to provide electrical neutrality. A and A' can vary independently and are each selected from $C_1$–$C_4$ alkoxy, especially ethoxy (i.e., —$CH_2CH_2O$—), propoxy, butoxy and mixed ethoxy/propoxy; p is from 0 to about 30, preferably 1 to about 4, and q is from 0 to about 30, preferably 1 to about 4, and most preferably to about 4; preferably both p and q are 1. See also: EP 2,084, published May 30, 1979, by The Procter & Gamble Company, which describes cationic co-surfactants of this type which are also useful herein.

AQA compounds wherein the hydrocarbyl substituent $R^1$ is $C_8$–$C_{11}$, especially $C_{10}$, enhance the rate of dissolution of laundry granules, especially under cold water conditions, as compared with the higher chain length materials. Accordingly, the $C_8$–$C_{11}$ AQA surfactants may be preferred by some formulators. The levels of the AQA surfactants used to prepare finished laundry detergent compositions can range from about 0.1% to about 5%, typically from about 0.45% to about 2.5%, by weight.

| Designation | $R^1$ | $R^2$ | ApR$^3$ | A'qR$^4$ |
|---|---|---|---|---|
| AQA-1 (also referred to as Coco Methyl EO2) | $C_{12}$–$C_{14}$ | $CH_3$ | EO | EO |
| AQA-2 | $C_{12}$–$C_{16}$ | $CH_3$ | (EO)$_2$ | EO |

-continued

| Designation | $R^1$ | $R^2$ | ApR$^3$ | A'qR$^4$ |
|---|---|---|---|---|
| AQA-3 (Coco Methyl EO4) | $C_{12}$–$C_{14}$ | $CH_3$ | (EO)$_2$ | (EO)$_2$ |
| AQA-4 | $C_{12}$ | $CH_3$ | EO | EO |
| AQA-5 | $C_{12}$–$C_{14}$ | $CH_3$ | (EO)$_2$ | (EO)$_3$ |
| AQA-6 | $C_{12}$–$C_{14}$ | $CH_3$ | (EO)$_2$ | (EO)$_3$ |
| AQA-7 | $C_8$–$C_{18}$ | $CH_3$ | (EO)$_3$ | (EO)$_2$ |
| AQA-8 | $C_{12}$–$C_{14}$ | $CH_3$ | (EO)$_4$ | (EO)$_4$ |
| AQA-9 | $C_{12}$–$C_{14}$ | $C_2H_5$ | (EO)$_3$ | (EO)$_3$ |
| AQA-10 | $C_{12}$–$C_{18}$ | $C_3H_7$ | (EO)$_3$ | (EO)$_4$ |
| AQA-11 | $C_{12}$–$C_{18}$ | $CH_3$ | (propoxy) | (EO)$_3$ |
| AQA-12 | $C_{10}$–$C_{18}$ | $C_2H_5$ | (iso-propoxy)$_2$ | (EO)$_3$ |
| AQA-13 | $C_{10}$–$C_{18}$ | $CH_3$ | (EO/PO)$_2$ | (EO)$_3$ |
| AQA-14 | $C_8$–$C_{18}$ | $CH_3$ | (EO)$_{15}$* | (EO)$_{15}$* |
| AQA-15 | $C_{10}$ | $CH_3$ | EO | EO |
| AQA-16 | $C_8$–$C_{12}$ | $CH_3$ | EO | EO |
| AQA-17 | $C_9$–$C_{11}$ | $CH_3$ | EO 3.5 Avg. | |
| AQA-18 | $C_{12}$ | $CH_3$ | EO 3.5 Avg. | |
| AQA-19 | $C_8$–$C_{14}$ | $CH_3$ | (EO)$_{10}$ | (EO)$_{10}$ |
| AQA-20 | $C_{10}$ | $C_2H_5$ | (EO)$_2$ | (EO)$_3$ |
| AQA-21 | $C_{12}$–$C_{14}$ | $C_2H_5$ | (EO)$_5$ | (EO)$_3$ |
| AQA-22 | $C_{12}$–$C_{18}$ | $C_3H_7$ | Bu | (EO)$_2$ |

*Ethoxy, optionally end-capped with methyl or ethyl.

The preferred bis-ethoxylated cationic surfactants herein are available under the trade name ETHOQUAD from Akzo Nobel Chemicals Company.

Highly preferred bis-AQA compounds for use herein are of the formula

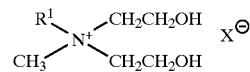

wherein $R^1$ is $C_{10}$–$C_{18}$ hydrocarbyl and mixtures thereof, preferably $C_{10}$, $C_{12}$, $C_{14}$ alkyl and mixtures thereof, and X is any convenient anion to provide charge balance, preferably chloride. With reference to the general AQA structure noted above, since in a preferred compound $R^1$ is derived from coconut ($C_{12}$–$C_{14}$ alkyl) fraction fatty acids, $R^2$ is methyl and ApR$^3$ and A'qR$^4$ are each monoethoxy, this preferred type of compound is referred to herein as "CocoMeEO2" or "AQA-1" in the above list.

Other preferred AQA compounds herein include compounds of the formula:

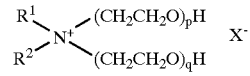

wherein $R^1$ is $C_{10}$–$C_{18}$ hydrocarbyl, preferably $C_{10}$–$C_{14}$ alkyl, independently p is 1 to about 3 and q is 1 to about 3, $R^2$ is $C_1$–$C_3$ alkyl, preferably methyl, and X is an anion, especially chloride.

Other compounds of the foregoing type include those wherein the ethoxy ($CH_2CH_2O$) units (EO) are replaced by butoxy (Bu), isopropoxy [$CH(CH_3)CH_2O$] and [$CH_2CH(CH_3O$] units (i-Pr) or n-propoxy units (Pr), or mixtures of EO and/or Pr and/or i-Pr units.

The following illustrates various other adjunct ingredients which may be used in the compositions of this invention, but is not intended to be limiting thereof. While the combination of the mid-chain branched primary alkyl surfactants with such adjunct compositional ingredients can be provided as finished products in the form of liquids, gels, bars, or the like using conventional techniques, the manufacture of the granular laundry detergents herein requires some special processing techniques in order to achieve optimal performance. Accordingly, the manufacture of laundry granules will be described hereinafter separately in the Granules Manufacture section (below), for the convenience of the formulator.

Additional cationic co-surfactants are described, for example, in the "Surfactant Science Series, Volume 4, Cationic Surfactants" or in the "Industrial Surfactants Handbook". Classes of useful cationic surfactants described in these references include amide quats (i.e., Lexquat AMG & Schercoquat CAS), glycidyl ether quats (i.e., Cyostat 609), hydroxyalkyl quats (i.e., Dehyquart E), alkoxypropyl quats (i.e., Tomah Q-17-2), polypropoxy quats (Emcol CC-9), cyclic alkylammonium compounds (i.e., pyridinium or imidazolinium quats), and/or benzalkonium quats.

Detersive Enzymes—Enzymes are preferably included in the present detergent compositions for a variety of purposes, including removal of protein-based, carbohydrate-based, or triglyceride-based stains from substrates, for the prevention of refugee dye transfer in fabric laundering, and for fabric restoration. Recent enzyme disclosures in detergents useful herein include bleach/amylase/protease combinations (EP 755,999 A; EP 756,001 A; EP 756,000 A); chondriotinase (EP 747,469 A); protease variants (WO 96/28566 A; WO 96/28557 A; WO 96/28556 A; WO 96/25489 A); xylanase (EP 709,452 A); keratinase (EP 747,470 A); lipase (GB 2,297,979 A; WO 96/16153 A; WO 96/12004 A; EP 698,659 A; WO 96/16154 A); cellulase (GB 2,294,269 A; WO 96/27649 A; GB 2,303,147 A); thermitase (WO 96/28558 A). More generally, suitable enzymes include proteases, amylases, lipases, cellulases, peroxidases, xylanases, keratinases, chondriotinases; thermitases, cutinases and mixtures thereof of any suitable origin, such as vegetable, animal, bacterial, fungal and yeast origin. Preferred selections are influenced by factors such as pH-activity and/or stability optima, thermostability, and stability to active detergents, builders and the like. In this respect bacterial or fungal enzymes are preferred, such as bacterial amylases and proteases, and fungal cellulases. Suitable enzymes are also described in U.S. Pat. Nos. 5,677,272, 5,679,630, 5,703,027, 5,703,034, 5,705,464, 5,707,950, 5,707,951, 5,710,115, 5,710,116, 5,710,118, 5,710,119 and 5,721,202.

"Detersive enzyme", as used herein, means any enzyme having a cleaning, stain removing or otherwise beneficial effect in a laundry, hard surface cleaning or personal care detergent composition. Preferred detersive enzymes are hydrolases such as proteases, amylases and lipases. Preferred enzymes for laundry purposes include, but are not limited to, proteases, cellulases, lipases and peroxidases. Highly preferred are amylases and/or proteases, including both current commercially available types and improved types which, though more and more bleach compatible though successive improvements, have a remaining degree of bleach deactivation susceptibility.

Enzymes are normally incorporated into detergent or detergent additive compositions at levels sufficient to provide a "cleaning-effective amount". The term "cleaning effective amount" refers to any amount capable of producing a cleaning, stain removal, soil removal, whitening, deodorizing, or freshness improving effect on substrates such as fabrics, dishware and the like. In practical terms for current commercial preparations, typical amounts are up to about 5 mg by weight, more typically 0.01 mg to 3 mg, of active enzyme per gram of the detergent composition. Stated otherwise, the compositions herein will typically comprise from 0.001% to 5%, preferably 0.01%–1% by weight of a commercial enzyme preparation. Protease enzymes are usually present in such commercial preparations at levels sufficient to provide from 0.005 to 0.1 Anson units (AU) of activity per gram of composition. For certain detergents it may be desirable to increase the active enzyme content of the commercial preparation in order to minimize the total amount of non-catalytically active materials and thereby improve spotting/filming or other end-results. Higher active levels may also be desirable in highly concentrated detergent formulations.

Suitable examples of proteases are the subtilisins which are obtained from particular strains of *B. subtilis* and *B. licheniformis*. One suitable protease is obtained from a strain of Bacillus, having maximum activity throughout the pH range of 8–12, developed and sold as ESPERASE® by Novo Industries A/S of Denmark, hereinafter "Novo". The preparation of this enzyme and analogous enzymes is described in GB 1,243,784 to Novo. Other suitable proteases include ALCALASE® and SAVINASE® from Novo and MAXATASE® from International Bio-Synthetics, Inc., The Netherlands; as well as Protease A as disclosed in EP 130,756 A, Jan. 9, 1985 and Protease B as disclosed in EP 303,761 A, Apr. 28, 1987 and EP 130,756 A, Jan. 9, 1985. See also a high pH protease from Bacillus sp. NCIMB 40338 described in WO 9318140 A to Novo. Enzymatic detergents comprising protease, one or more other enzymes, and a reversible protease inhibitor are described in WO 9203529 A to Novo. Other preferred proteases include those of WO 9510591 A to Procter & Gamble. When desired, a protease having decreased adsorption and increased hydrolysis is available as described in WO 9507791 to Procter & Gamble. A recombinant trypsin-like protease for detergents suitable herein is described in WO 9425583 to Novo.

In more detail, an especially preferred protease, referred to as "Protease D" is a carbonyl hydrolase variant having an amino acid sequence not found in nature, which is derived from a precursor carbonyl hydrolase by substituting a different amino acid for a plurality of amino acid residues at a position in said carbonyl hydrolase equivalent to position +76, preferably also in combination with one or more amino acid residue positions equivalent to those selected from the group consisting of +99, +101, +103, +104, +107, +123, +27, +105, +109, +126, +128, +135, +156, +166, +195, +197, +204, +206, +210, +216, +217, +218, +222, +260, +265, and/or +274 according to the numbering of *Bacillus amyloliquefaciens subtilisin*, as described in WO 95/10615 published Apr. 20, 1995 by Genencor International.

Useful proteases are also described in PCT publications: WO 95/30010 published Nov. 9, 1995 by The Procter & Gamble Company; WO 95/30011 published Nov. 9, 1995 by The Procter & Gamble Company; WO 95/29979 published Nov. 9, 1995 by The Procter & Gamble Company.

Amylases suitable herein include, for example, α-amylases described in GB 1,296,839 to Novo; RAPIDASE®, International Bio-Synthetics, Inc. and TERMAMYL®, Novo. FUNGAMYL® from Novo is especially useful. Engineering of enzymes for improved stability, e.g., oxidative stability, is known. See, for example J. Biological Chem., Vol. 260, No. 11, June 1985, pp. 6518–6521. Certain preferred embodiments of the present compositions can make use of amylases having improved stability in detergents, especially improved oxidative stability as measured against a reference-point of TERMAMYL® in commercial use in 1993. These preferred amylases herein share the characteristic of being "stability-enhanced" amylases, characterized, at a minimum, by a measurable improvement in one or more of: oxidative stability, e.g., to hydrogen peroxide/tetraacetylethylenediamine in buffered solution at pH 9–10; thermal stability, e.g., at common wash temperatures such as about 60° C.; or alkaline stability, e.g., at a pH from about 8 to about 11, measured versus the above-identified reference-point amylase. Stability can be measured using any of the art-disclosed technical tests. See, for example, references disclosed in WO 9402597. Stability-enhanced amylases can be obtained from Novo or from Genencor International. One class of highly preferred amylases herein have the commonality of being derived using site-directed mutagenesis from one or more of the Bacillus amylases, especially the Bacillus α-amylases, regardless of whether one, two or multiple amylase strains are the immediate precursors. Oxidative stability-enhanced amylases vs. the above-identified reference amylase are preferred for use, especially in bleaching, more preferably oxygen bleaching, as distinct from chlorine bleaching, detergent compositions herein. Such preferred amylases include (a) an amylase according to the hereinbefore incorporated WO 9402597, Novo, Feb. 3, 1994, as further illustrated by a mutant in which substitution is made, using alanine or threonine, preferably threonine, of the methionine residue located in position 197 of the *B. licheniformis* alpha-amylase, known as TERMAMYL®, or the homologous position variation of a similar parent amylase, such as *B. amyloliquefaciens, B. subtilis*, or *B. stearothermophilus*; (b) stability-enhanced amylases as described by Genencor International in a paper entitled "Oxidatively Resistant alpha-Amylases" presented at the 207th American Chemical Society National Meeting, Mar. 13–17, 1994, by C. Mitchinson. Therein it was noted that bleaches in automatic dishwashing detergents inactivate alpha-amylases but that improved oxidative stability amylases have been made by Genencor from *B. licheniformis* NCIB8061. Methionine (Met) was identified as the most likely residue to be modified. Met was substituted, one at a time, in positions 8, 15, 197, 256, 304, 366 and 438 leading to specific mutants, particularly important being M197L and M197T with the M197T variant being the most stable expressed variant. Stability was measured in CASCADE® and SUNLIGHT®; (c) particularly preferred amylases herein include amylase variants having additional modification in the immediate parent as described in WO 9510603 A and are available from the assignee, Novo, as DURAMYL®. Other particularly preferred oxidative stability enhanced amylase include those described in WO 9418314 to Genencor International and WO 9402597 to Novo. Any other oxidative stability-enhanced amylase can be used, for example as derived by site-directed mutagenesis from known chimeric, hybrid or simple mutant parent forms of available amylases. Other preferred enzyme modifications are accessible. See WO 9509909 A to Novo.

Other amylase enzymes include those described in WO 95/26397 and in co-pending application by Novo Nordisk PCT/DK96/00056. Specific amylase enzymes for use in the detergent compositions of the present invention include α-amylases characterized by having a specific activity at least 25% higher than the specific activity of Termamyl® at a temperature range of 25° C. to 55° C. and at a pH value in the range of 8 to 10, measured by the Phadebas® α-amylase activity assay. (Such Phadebas® α-amylase activity assay is described at pages 9–10, WO 95/26397.) Also included herein are α-amylases which are at least 80% homologous with the amino acid sequences shown in the SEQ ID listings in the references. These enzymes are preferably incorporated into laundry detergent compositions at a level from 0.00018% to 0.060% pure enzyme by weight of the total composition, more preferably from 0.00024% to 0.048% pure enzyme by weight of the total composition.

Cellulases usable herein include both bacterial and fungal types, preferably having a pH optimum between 5 and 9.5. U.S. Pat. No. 4,435,307, Barbesgoard et al, Mar. 6, 1984, discloses suitable fungal cellulases from *Humicola insolens* or *Humicola strain* DSM1800 or a cellulase 212-producing fungus belonging to the genus Aeromonas, and cellulase extracted from the hepatopancreas of a marine mollusk, Dolabella Auricula Solander. Suitable cellulases are also disclosed in GB-A-2.075.028; GB-A-2.095.275 and DE-OS-2.247.832. CAREZYME® and CELLUZYME® (Novo) are especially useful. See also WO 9117243 to Novo.

Suitable lipase enzymes for detergent usage include those produced by microorganisms of the Pseudomonas group, such as *Pseudomonas stutzeri* ATCC 19.154, as disclosed in GB 1,372,034. See also lipases in Japanese Patent Application 53,20487, laid open Feb. 24, 1978. This lipase is available from Amano Pharmaceutical Co. Ltd., Nagoya, Japan, under the trade name Lipase P "Amano," or "Amano-P." Other suitable commercial lipases include Amano-CES, lipases ex *Chromobacter viscosum*, e.g. *Chromobacter viscosum* var. *lipolyticum* NRRLB 3673 from Toyo Jozo Co., Tagata, Japan; *Chromobacter viscosum* lipases from U.S. Biochemical Corp., U.S.A. and Disoynth Co., The Netherlands, and lipases ex Pseudomonas gladioli. LIPOLASE® enzyme derived from *Humicola lanuginosa* and commercially available from Novo, see also EP 341,947, is a preferred lipase for use herein. Lipase and amylase variants stabilized against peroxidase enzymes are described in WO 9414951 A to Novo. See also WO 9205249 and RD 94359044.

Cutinase enzymes suitable for use herein are described in WO 8809367 A to Genencor.

Peroxidase enzymes may be used in combination with oxygen sources, e.g., percarbonate, perborate, hydrogen peroxide, etc., for "solution bleaching" or prevention of transfer of dyes or pigments removed from substrates during the wash to other substrates present in the wash solution. Known peroxidases include horseradish peroxidase, ligninase, and haloperoxidases such as chloro- or bromo-peroxidase. Peroxidase-containing detergent compositions are disclosed in WO 89099813 A, Oct. 19, 1989 to Novo and WO 8909813 A to Novo.

A range of enzyme materials and means for their incorporation into synthetic detergent compositions is also disclosed in WO 9307263 A and WO 9307260 A to Genencor International, WO 8908694 A to Novo, and U.S. Pat. No. 3,553,139, Jan. 5, 1971 to McCarty et al. Enzymes are further disclosed in U.S. Pat. No. 4,101,457, Place et al, Jul. 18, 1978, and in U.S. Pat. No. 4,507,219, Hughes, Mar. 26, 1985. Enzyme materials useful for liquid detergent formulations, and their incorporation into such formulations, are disclosed in U.S. Pat. No. 4,261,868, Hora et al, Apr. 14, 1981. Enzymes for use in detergents can be stabilized by various techniques. Enzyme stabilization techniques are disclosed and exemplified in U.S. Pat. No. 3,600,319, Aug. 17, 1971, Gedge et al, EP 199,405 and EP 200,586, Oct. 29, 1986, Venegas. Enzyme stabilization systems are also described, for example, in U.S. Pat. No. 3,519,570. A useful Bacillus, sp. AC13 giving proteases, xylanases and cellulases, is described in WO 9401532 A to Novo.

Builders—Detergent builders are preferably included in the compositions herein, for example to assist in controlling mineral, especially Ca and/or Mg, hardness in wash water or to assist in the removal and/or suspension of particulate soils from surfaces and sometimes to provide alkalinity and/or buffering action. In solid formulations, builders sometimes serve as absorbents for surfactants. Alternately, certain compositions can be formulated with completely water-soluble builders, whether organic or inorganic, depending on the intended use.

Suitable silicate builders include water-soluble and hydrous solid types and including those having chain-, layer-, or three-dimensional-structure as well as amorphous-solid silicates or other types, for example especially adapted for use in non-structured-liquid detergents. Preferred are alkali metal silicates, particularly those liquids and solids having a $SiO_2:Na_2O$ ratio in the range 1.6:1 to 3.2:1, including solid hydrous 2-ratio silicates marketed by PQ Corp. under the tradename BRITESIL® (, e.g., BRITESIL H2O; and layered silicates, e.g., those described in U.S. Pat. No. 4,664,839, May 12, 1987, H. P. Rieck. NaSKS-6, sometimes abbreviated "SKS-6", is a crystalline layered aluminum-free $\delta$-$Na_2SiO_5$ morphology silicate marketed by Hoechst and is preferred especially in granular laundry compositions. See preparative methods in German DE-A-3,417,649 and DE-A-3,742,043. Other layered silicates, such as those having the general formula $NaMSi_xO_{2x+1}.yH_2O$ wherein M is sodium or hydrogen, x is a number from 1.9 to 4, preferably 2, and y is a number from 0 to 20, preferably 0, can also or alternately be used herein. Layered silicates from Hoechst also include NaSKS-5, NaSKS-7 and NaSKS-11, as the $\alpha$, $\beta$ and $\gamma$ layer-silicate forms. Other silicates may also be useful, such as magnesium silicate, which can serve as a crisping agent in granules, as a stabilizing agent for bleaches, and as a component of suds control systems.

Also suitable for use herein are synthesized crystalline ion exchange materials or hydrates thereof having chain structure and a composition represented by the following general formula in an anhydride form: $xM_2O.ySiO_2.zM'O$ wherein M is Na and/or K, M' is Ca and/or Mg; y/x is 0.5 to 2.0 and z/x is 0.005 to 1.0 as taught in U.S. Pat. No. 5,427,711, Sakaguchi et al, Jun. 27, 1995.

Aluminosilicate builders, such as zeolites, are especially useful in granular detergents, but can also be incorporated in liquids, pastes or gels. Suitable for the present purposes are those having empirical formula: $[M_z(AlO_2)_z(SiO_2)_v].xH_2O$ wherein z and v are integers of at least 6, the molar ratio of z to v is in the range from 1.0 to 0.5, and x is an integer from 15 to 264. Aluminosilicates can be crystalline or amorphous, naturally-occurring or synthetically derived. An aluminosilicate production method is in U.S. Pat. No. 3,985,669, Krummel, et al, Oct. 12, 1976. Preferred synthetic crystalline aluminosilicate ion exchange materials are available as Zeolite A, Zeolite P (B), Zeolite X and, to whatever extent this differs from Zeolite P, the so-called Zeolite MAP. Natural types, including clinoptilolite, may be used. Zeolite A has the formula: $Na_{12}[(AlO_2)_{12}(SiO_2)_{12}].xH_2O$ wherein x is from 20 to 30, especially 27. Dehydrated zeolites (x=0–10) may also be used. Preferably, the aluminosilicate has a particle size of 0.1–10 microns in diameter.

Builder level can vary widely depending upon end use and physical form of the composition. Built detergents typically comprise at least about 1% builder. Liquid formulations typically comprise about 5% to about 50%, more typically 5% to 35% of builder. Granular formulations typically comprise from about 10% to about 80%, more typically 15% to 50% builder by weight of the detergent composition. Lower or higher levels of builders are not excluded. For example, certain detergent additive or high-surfactant formulations can be unbuilt.

Suitable builders herein can be selected from the group consisting of phosphates and polyphosphates, especially the sodium salts; carbonates, bicarbonates, sesquicarbonates and carbonate minerals other than sodium carbonate or sesquicarbonate; organic mono-, di-, tri-, and tetracarboxylates especially water-soluble nonsurfactant carboxylates in acid, sodium, potassium or alkanolammonium salt form, as well as oligomeric or water-soluble low molecular weight polymer carboxylates including aliphatic and aromatic types; and phytic acid. These may be complemented by borates, e.g., for pH-buffering purposes, or by sulfates, especially sodium sulfate and any other fillers or carriers which may be important to the engineering of stable surfactant and/or builder-containing detergent compositions.

Builder mixtures, sometimes termed "builder systems" can be used and typically comprise two or more conventional builders, optionally complemented by chelants, pH-buffers or fillers, though these latter materials are generally accounted for separately when describing quantities of materials herein. In terms of relative quantities of surfactant and builder in the present detergents, preferred builder systems are typically formulated at a weight ratio of surfactant to builder of from about 60:1 to about 1:80. Certain preferred laundry detergents have said ratio in the range 0.90:1.0 to 4.0:1.0, more preferably from 0.95:1.0 to 3.0:1.0.

P-containing detergent builders often preferred where permitted by legislation include, but are not limited to, the alkali metal, ammonium and alkanolammonium salts of polyphosphates exemplified by the tripolyphosphates, pyrophosphates, glassy polymeric meta-phosphates; and phosphonates.

Suitable carbonate builders include alkaline earth and alkali metal carbonates as disclosed in German Patent Application No. 2,321,001 published on Nov. 15, 1973, although sodium bicarbonate, sodium carbonate, sodium sesquicarbonate, and other carbonate minerals such as trona or any convenient multiple salts of sodium carbonate and calcium carbonate such as those having the composition $2Na_2CO_3.CaCO_3$ when anhydrous, and even calcium carbonates including calcite, aragonite and vaterite, especially forms having high surface areas relative to compact calcite may be useful, for example as seeds or for use in synthetic detergent bars.

Suitable "organic detergent builders", as described herein for use with the alkylarylsulfonate surfactant system include polycarboxylate compounds, including water-soluble non-surfactant dicarboxylates and tricarboxylates. More typically builder polycarboxylates have a plurality of carboxylate groups, preferably at least 3 carboxylates. Carboxylate builders can be formulated in acid, partially neutral, neutral or overbased form. When in salt form, alkali metals, such as sodium, potassium, and lithium, or alkanolammonium salts are preferred. Polycarboxylate builders include the ether polycarboxylates, such as oxydisuccinate, see Berg, U.S. Pat. No. 3,128,287, Apr. 7, 1964, and Lamberti et al, U.S. Pat. No. 3,635,830, Jan. 18, 1972; "TMS/TDS" builders of U.S. Pat. No. 4,663,071, Bush et al, May 5, 1987; and other ether carboxylates including cyclic and alicyclic compounds, such as those described in U.S. Pat. Nos. 3,923,679; 3,835,163; 4,158,635; 4,120,874 and 4,102,903.

Other suitable organic detergent builders are the ether hydroxypolycarboxylates, copolymers of maleic anhydride with ethylene or vinyl methyl ether; 1,3,5-trihydroxy benzene-2,4,6-trisulphonic acid; carboxymethyloxysuccinic acid; the various alkali metal, ammonium and substituted ammonium salts of polyacetic acids such as ethylenediamine tetraacetic acid and nitrilotriacetic acid; as well as mellitic acid, succinic acid, polymaleic acid, benzene 1,3,5-tricarboxylic acid, carboxymethyloxysuccinic acid, and soluble salts thereof.

Citrates, e.g., citric acid and soluble salts thereof are important carboxylate builders e.g., for heavy duty liquid detergents, due to availability from renewable resources and biodegradability. Citrates can also be used in granular compositions, especially in combination with zeolite and/or layered silicates. Oxydisuccinates are also especially useful in such compositions and combinations.

Where permitted, and especially in the formulation of bars used for hand-laundering operations, alkali metal phosphates such as sodium tripolyphosphates, sodium pyrophosphate and sodium orthophosphate can be used. Phosphonate builders such as ethane-1-hydroxy-1,1-diphosphonate and other known phosphonates, e.g., those of U.S. Pat. Nos. 3,159,581; 3,213,030; 3,422,021; 3,400,148 and 3,422,137 can also be used and may have desirable antiscaling properties.

Certain detersive surfactants or their short-chain homologues also have a builder action. For unambiguous formula accounting purposes, when they have surfactant capability, these materials are summed up as detersive surfactants. Preferred types for builder functionality are illustrated by: 3,3-dicarboxy-4-oxa-1,6-hexanedioates and the related compounds disclosed in U.S. Pat. No. 4,566,984, Bush, Jan. 28, 1986. Succinic acid builders include the $C_5$–$C_{20}$ alkyl and alkenyl succinic acids and salts thereof. Succinate builders also include: laurylsuccinate, myristylsuccinate, palmitylsuccinate, 2-dodecenylsuccinate (preferred), 2-pentadecenylsuccinate, and the like. Lauryl-succinates are described in European Patent Application 86200690.5/0, 200,263, published Nov. 5, 1986. Fatty acids, e.g., $C_{12}$–$C_{18}$ monocarboxylic acids, can also be incorporated into the compositions as surfactant/builder materials alone or in combination with the aforementioned builders, especially citrate and/or the succinate builders, to provide additional builder activity. Other suitable polycarboxylates are disclosed in U.S. Pat. No. 4,144,226, Crutchfield et al, Mar. 13, 1979 and in U.S. Pat. No. 3,308,067, Diehl, Mar. 7, 1967. See also Diehl, U.S. Pat. No. 3,723,322.

Other types of inorganic builder materials which can be used have the formula $(M_x)_i Ca_y (CO_3)_z$ wherein x and i are integers from 1 to 15, y is an integer from 1 to 10, z is an integer from 2 to 25, $M_i$ are cations, at least one of which is a water-soluble, and the equation $\Sigma_{i=1-15}(x_i$ multiplied by the valence of $M_i)+2y=2z$ is satisfied such that the formula has a neutral or "balanced" charge. These builders are referred to herein as "Mineral Builders", examples of these builders, their use and preparation can be found in U.S. Pat. No. 5,707,959. Another suitable class of inorganic builders are the Magnesiosilicates, see WO97/0179.

Bleaching Agents—Preferred compositions of the present invention comprise, as part or all of the laundry or cleaning adjunct materials, a bleaching agent. Oxygen bleaching agents useful in the present invention can be any of the oxidizing agents known for laundry, hard surface cleaning, automatic dishwashing or denture cleaning purposes. Oxygen bleaches or mixtures thereof are preferred, though other oxidant bleaches, such as oxygen, an enzymatic hydrogen peroxide producing system, or hypohalites such as chlorine bleaches like hypochlorite, may also be used.

Common oxygen bleaches of the peroxygen type include hydrogen peroxide, inorganic peroxohydrates, organic peroxohydrates and the organic peroxyacids, including hydrophilic and hydrophobic mono- or di-peroxyacids. These can be peroxycarboxylic acids, peroxyimidic acids, amidoperoxycarboxylic acids, or their salts including the calcium, magnesium, or mixed-cation salts. Peracids of various kinds can be used both in free form and as precursors known as "bleach activators" or "bleach promoters" which, when combined with a source of hydrogen peroxide, perhydrolyze to release the corresponding peracid.

Also useful herein as oxygen bleaches are the inorganic peroxides such as $Na_2O_2$, superoxides such as $KO_2$, organic hydroperoxides such as cumene hydroperoxide and t-butyl hydroperoxide, and the inorganic peroxoacids and their salts such as the peroxosulfuric acid salts, especially the potassium salts of peroxodisulfuric acid and, more preferably, of peroxomonosulfuric acid including the commercial triple-salt form sold as OXONE by DuPont and also any equivalent commercially available forms such as CUROX from Akzo or CAROAT from Degussa. Certain organic peroxides, such as dibenzoyl peroxide, may be useful, especially as additives rather than as primary oxygen bleach.

Mixed oxygen bleach systems are generally useful, as are mixtures of any oxygen bleaches with the known bleach activators, organic catalysts, enzymatic catalysts and mixtures thereof; moreover such mixtures may further include brighteners, photobleaches' and dye transfer inhibitors of types well-known in the art.

Preferred oxygen bleaches, as noted, include the peroxohydrates, sometimes known as peroxyhydrates or peroxohydrates. These are organic or, more commonly, inorganic salts capable of releasing hydrogen peroxide readily. Peroxohydrates are the most common examples of "hydrogen peroxide source" materials and include the perborates, percarbonates, perphosphates, and persilicates. Suitable peroxohydrates include sodium carbonate peroxyhydrate and equivalent commercial "percarbonate" bleaches, and any of the so-called sodium perborate hydrates, the "tetrahydrate" and "monohydrate" being preferred; though sodium pyrophosphate peroxyhydrate can be used. Many such peroxohydrates are available in processed forms with coatings, such as of silicate and/or borate and/or waxy materials and/or surfactants, or have particle geometries, such as compact spheres, which improve storage stability. By way of organic peroxohydrates, urea peroxyhydrate can also be useful herein.

Percarbonate bleach includes, for example, dry particles having an average particle size in the range from about 500 micrometers to about 1,000 micrometers, not more than about 10% by weight of said particles being smaller than about 200 micrometers and not more than about 10% by weight of said particles being larger than about 1,250 micrometers. Percarbonates and perborates are widely available in commerce, for example from FMC, Solvay and Tokai Denka.

Organic percarboxylic acids useful herein as the oxygen bleach include magnesium monoperoxyphthalate hexahydrate, available from Interox, m-chloro perbenzoic acid and its salts, 4-nonylamino-4-oxoperoxybutyric acid and diperoxydodecanedioic acid and their salts. Such bleaches are disclosed in U.S. Pat. No. 4,483,781, U.S. patent application Ser. No. 740,446, Burns et al, filed Jun. 3, 1985, EP-A 133,354, published Feb. 20, 1985, and U.S. Pat. No. 4,412,934. Organic percarboxylic acids usable herein include those containing one, two or more peroxy groups, and can be aliphatic or aromatic. Highly preferred oxygen bleaches also include 6-nonylamino-6-oxoperoxycaproic acid (NAPAA) as described in U.S. Pat. No. 4,634,551.

An extensive and exhaustive listing of useful oxygen bleaches, including inorganic peroxohydrates, organic peroxohydrates and the organic peroxyacids, including hydrophilic and hydrophobic mono- or di-peroxyacids, peroxycarboxylic acids, peroxyimidic acids, amidoperoxycarboxylic acids, or their salts including the calcium, magnesium, or mixed-cation salts, can be found in U.S. Pat. Nos. 5,622,646 and 5,686,014.

Other useful peracids and bleach activators herein are in the family of imidoperacids and imido bleach activators.

These include phthaloylimidoperoxycaproic acid and related arylimido-substituted and acyloxynitrogen derivatives. For listings of such compounds, preparations and their incorporation into laundry compositions including both granules and liquids, See U.S. Pat. No. 5,487,818; U.S. Pat. No. 5,470,988, U.S. Pat. No. 5,466,825; U.S. Pat. No. 5,419,846; U.S. Pat. No. 5,415,796; U.S. Pat. No. 5,391,324; U.S. Pat. No. 5,328,634; U.S. Pat. No. 5,310,934; U.S. Pat. No. 5,279,757; U.S. Pat. No. 5,246,620; U.S. Pat. No. 5,245,075; U.S. Pat. No. 5,294,362; U.S. Pat. No. 5,423,998; U.S. Pat. No. 5,208,340; U.S. Pat. No. 5,132,431 and U.S. Pat. No. 5,087,385.

Useful diperoxyacids include, for example, 1,12-diperoxydodecanedioic acid (DPDA); 1,9-diperoxyazelaic acid; diperoxybrassilic acid; diperoxysebasic acid and diperoxyisophthalic acid; 2-decyldiperoxybutane-1,4-dioic acid; and 4,4'-sulphonylbisperoxybenzoic acid.

More generally, the terms "hydrophilic" and "hydrophobic" used herein in connection with any of the oxygen bleaches, especially the peracids, and in connection with bleach activators, are in the first instance based on whether a given oxygen bleach effectively performs bleaching of fugitive dyes in solution thereby preventing fabric graying and discoloration and/or removes more hydrophilic stains such as tea, wine and grape juice—in this case it is termed "hydrophilic". When the oxygen bleach or bleach activator has a significant stain removal, whiteness-improving or cleaning effect on dingy, greasy, carotenoid, or other hydrophobic soils, it is termed "hydrophobic". The terms are applicable also when referring to peracids or bleach activators used in combination with a hydrogen peroxide source. The current commercial benchmarks for hydrophilic performance of oxygen bleach systems are: TAED or peracetic acid, for benchmarking hydrophilic bleaching. NOBS or NAPAA are the corresponding benchmarks for hydrophobic bleaching. The terms "hydrophilic", "hydrophobic" and "hydrotropic" with reference to oxygen bleaches including peracids and here extended to bleach activator have also been used somewhat more narrowly in the literature. See especially Kirk Othmer's Encyclopedia of Chemical Technology, Vol. 4., pages 284–285. This reference provides a chromatographic retention time and critical micelle concentration-based set of criteria, and is useful to identify and/or characterize preferred sub-classes of hydrophobic, hydrophilic and hydrotropic oxygen bleaches and bleach activators that can be used in the present invention.

While not preferred for compositions of the present invention which comprise detersive enzymes, the present invention compositions may also comprise as the bleaching agent a chlorine-type bleaching material. Such agents are well known in the art, and include for example sodium dichloroisocyanurate ("NaDCC"), or sodium hypochlorite (NaOCl).

Bleach Activators

Bleach activators useful herein include amides, imides, esters and anhydrides. Commonly at least one substituted or unsubstituted acyl moiety is present, covalently connected to a leaving group as in the structure R—C(O)—L. In one preferred mode of use, bleach activators are combined with a source of hydrogen peroxide, such as the perborates or percarbonates, in a single product. Conveniently, the single product leads to in situ production in aqueous solution (i.e., during the washing process) of the percarboxylic acid corresponding to the bleach activator. The product itself can be hydrous, for example a powder, provided that water is controlled in amount and mobility such that storage stability is acceptable. Alternately, the product can be an anhydrous solid or liquid. In another mode, the bleach activator or oxygen bleach is incorporated in a pretreatment product, such as a stain stick; soiled, pretreated substrates can then be exposed to further treatments, for example of a hydrogen peroxide source. With respect to the above bleach activator structure RC(O)L, the atom in the leaving group connecting to the peracid-forming acyl moiety R(C)O— is most typically O or N. Bleach activators can have non-charged, positively or negatively charged peracid-forming moieties and/or noncharged, positively or negatively charged leaving groups. One or more peracid-forming moieties or leaving-groups can be present. See, for example, U.S. Pat. No. 5,595,967, U.S. Pat. No. 5,561,235, U.S. Pat. No. 5,560,862 or the bis-(peroxy-carbonic) system of U.S. Pat. No. 5,534,179. Mixtures of suitable bleach activators can also be used. Bleach activators can be substituted with electron-donating or electron-releasing moieties either in the leaving-group or in the peracid-forming moiety or moieties, changing their reactivity and making them more or less suited to particular pH or wash conditions. For example, electron-withdrawing groups such as $NO_2$ improve the efficacy of bleach activators intended for use in mild-pH (e.g., from about 7.5— to about 9.5) wash conditions.

An extensive and exhaustive disclosure of suitable bleach activators and suitable leaving groups, as well as how to determine suitable activators, can be found in U.S. Pat. Nos. 5,686,014 and 5,622,646.

Cationic bleach activators include quaternary carbamate-, quaternary carbonate-, quaternary ester- and quaternary amide-types, delivering a range of cationic peroxyimidic, peroxycarbonic or peroxycarboxylic acids to the wash. An analogous but non-cationic palette of bleach activators is available when quaternary derivatives are not desired. In more detail, cationic activators include quaternary ammonium-substituted activators of WO 96-06915, U.S. Pat. No. 4,751,015 and 4,397,757, EP-A-284292, EP-A-331, 229 and EP-A-03520. Also useful are cationic nitrites as disclosed in EP-A303,520 and in European Patent Specification 458,396 and 464,880. Other nitrile types have electron-withdrawing substituents as described in U.S. Pat. No. 5,591,378.

Other bleach activator disclosures include GB 836,988; 864,798; 907,356; 1,003,310 and 1,519,351; German Patent 3,337,921; EP-A-0185522; EP-A-0174132; EP-A-0120591; U.S. Pat. Nos. 1,246,339; 3,332,882; 4,128,494; 4,412,934 and 4,675,393, and the phenol sulfonate ester of alkanoyl amino acids disclosed in U.S. Pat. No. 5,523,434. Suitable bleach activators include any acetylated diamine types, whether hydrophilic or hydrophobic in character.

Of the above classes of bleach precursors, preferred classes include the esters, including acyl phenol sulfonates, acyl alkyl phenol sulfonates or acyl oxybenzenesulfonates (OBS leaving-group); the acyl-amides; and the quaternary ammonium substituted peroxyacid precursors including the cationic nitriles.

Preferred bleach activators include N,N,N'N'-tetraacetyl ethylene diamine (TAED) or any of its close relatives including the triacetyl or other unsymmetrical derivatives. TAED and the acetylated carbohydrates such as glucose pentaacetate and tetraacetyl xylose are preferred hydrophilic bleach activators. Depending on the application, acetyl triethyl citrate, a liquid, also has some utility, as does phenyl benzoate.

Preferred hydrophobic bleach activators include sodium nonanoyloxybenzene sulfonate (NOBS or SNOBS), N-(alkanoyl)aminoalkanoyloxy benzene sulfonates, such as 4-[N-(nonanoyl)aminohexanoyloxy]-benzene sulfonate or (NACA-OBS) as described in U.S. Pat. No. 5,534,642 and in EPA 0 355 384 A1, substituted amide types described in detail hereinafter, such as activators related to NAPAA, and activators related to certain imidoperacid bleaches, for example as described in U.S. Pat. No. 5,061,807, issued Oct. 29, 1991 and assigned to Hoechst Aktiengesellschaft of Frankfurt, Germany and Japanese Laid-Open Patent Application (Kokai) No. 4-28799.

Another group of peracids and bleach activators herein are those derivable from acyclic imidoperoxycarboxylic acids and salts thereof, See U.S. Pat. No. 5,415,796, and cyclic imidoperoxycarboxylic acids and salts thereof, see U.S. Pat. Nos. 5,061,807, 5,132,431, 5,6542,69, 5,246,620, 5,419,864 and 5,438,147.

Other suitable bleach activators include sodium-4-benzoyloxy benzene sulfonate (SBOBS); sodium-1-methyl-2-benzoyloxy benzene-4-sulphonate; sodium-4-methyl-3-benzoyloxy benzoate (SPCC); trimethyl ammonium toluyloxy-benzene sulfonate; or sodium 3,5,5-trimethyl hexanoyloxybenzene sulfonate (STHOBS).

Bleach activators may be used in an amount of up to 20%, preferably from 0.1–10% by weight, of the composition, though higher levels, 40% or more, are acceptable, for example in highly concentrated bleach additive product forms or forms intended for appliance automated dosing.

Highly preferred bleach activators useful herein are amide-substituted and an extensive and exhaustive disclosure of these activators can be found in U.S. Pat. Nos. 5,686,014 and 5,622,646.

Other useful activators, disclosed in U.S. Pat. No. 4,966,723, are benzoxazin-type, such as a $C_6H_4$ ring to which is fused in the 1,2-positions a moiety —C(O)OC($R^1$)=N—. A highly preferred activator of the benzoxazin-type is:

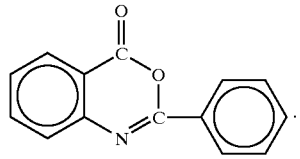

Depending on the activator and precise application, good bleaching results can be obtained from bleaching systems having with in-use pH of from about 6 to about 13, preferably from about 9.0 to about 10.5. Typically, for example, activators with electron-withdrawing moieties are used for near-neutral or sub-neutral pH ranges. Alkalis and buffering agents can be used to secure such pH.

Acyl lactam activators are very useful herein, especially the acyl caprolactams (see for example WO 94-28102 A) and acyl valerolactams (see U.S. Pat. No. 5,503,639). See also U.S. Pat. No. 4,545,784 which discloses acyl caprolactams, including benzoyl caprolactam adsorbed into sodium perborate. In certain preferred embodiments of the invention, NOBS, lactam activators, imide activators or amide-functional activators, especially the more hydrophobic derivatives, are desirably combined with hydrophilic activators such as TAED, typically at weight ratios of hydrophobic activator: TAED in the range of 1:5 to 5:1, preferably about 1:1. Other suitable lactam activators are alpha-modified, see WO 96-22350 A1, Jul. 25, 1996. Lactam activators, especially the more hydrophobic types, are desirably used in combination with TAED, typically at weight ratios of amido-derived or caprolactam activators: TAED in the range of 1:5 to 5:1, preferably about 1:1. See also the bleach activators having cyclic amidine leaving-group disclosed in U.S. Pat. No. 5,552,556.

Nonlimiting examples of additional activators useful herein are to be found in U.S. Pat. No. 4,915,854, U.S. Pat. Nos. 4,412,934 and 4,634,551. The hydrophobic activator nonanoyloxybenzene sulfonate (NOBS) and the hydrophilic tetraacetyl ethylene diamine (TAED) activator are typical, and mixtures thereof can also be used.

Additional activators useful herein include those of U.S. Pat. No. 5,545,349.

Transition Metal Bleach Catalysts

If desired, the bleaching compounds can be catalyzed by means of a manganese compound. Such compounds are well known in the art and include, for example, the manganese-based catalysts disclosed in U.S. Pat. No. 5,246,621, U.S. Pat. No. 5,244,594; U.S. Pat. No. 5,194,416; U.S. Pat. No. 5,114,606; European Pat. App. Pub. Nos. 549,271A1, 549,272A1, 544,440A2, 544,490A1; and PCT applications PCT/IB98/00298, PCT/IB98/00299, PCT/IB98/00300, and PCT/IB98/00302; Preferred examples of these catalysts include $Mn^{IV}{}_2(u$-$O)_3(1,4,7$-trimethyl-$1,4,7$-triazacyclononane$)_2(PF_6)_2$, $Mn^{III}{}_2(u$-$O)_1(u$-$OAc)_2(1,4,7$-trimethyl-$1,4,7$-triazacyclononane$)_2(ClO_4)_2$, $Mn^{IV}{}_4(u$-$O)_6(1,4,7$-triazacyclononane$)_4(ClO_4)_4$, $Mn^{III}$–$Mn^{IV}{}_4(u$-$O)_1(u$-$OAc)_2$-$(1,4,7$-trimethyl-$1,4,7$-triazacyclononane$)_2(ClO_4)_3$, $Mn^{IV}(1,4,7$-trimethyl-$1,4,7$-triazacyclononane$)$-$(OCH_3)_3(PF_6)$, and mixtures thereof. Other metal-based bleach catalysts include those disclosed in U.S. Pat. Nos. 4,430,243, 5,114,611 5,622,646 and 5,686,014. The use of manganese with various complex ligands to enhance bleaching is also reported in the following U.S. Pat. Nos. 4,728,455; 5,284,944; 5,246,612; 5,256,779; 5,280,117; 5,274,147; 5,153,161; and 5,227,084.

Cobalt bleach catalysts useful herein are known, and are described, for example, in M. L. To be, "Base Hydrolysis of Transition-Metal Complexes", Adv. Inorg. Bioinorg. Mech., (1983), 2, pages 1–94. The most preferred cobalt catalyst useful herein are cobalt pentaamine acetate salts having the formula $[Co(NH_3)_5OAc]T_y$, wherein "OAc" represents an acetate moiety and "$T_y$" is an anion, and especially cobalt pentaamine acetate chloride, $[Co(NH_3)_5OAc]Cl_2$; as well as $[Co(NH_3)_5OAc](OAc)_2$; $[Co(NH_3)_5OAc](PF_6)_2$; $[Co(NH_3)_5 OAc](SO_4)$; $[Co(NH_3)_5OAc](BF_4)_2$; and $[Co(NH_3)_5 OAc](NO_3)_2$ (herein "PAC"). These cobalt catalysts are readily prepared by known procedures, such as taught for example in the Tobe article and the references cited therein, and in U.S. Pat. No. 4,810,410, to Diakun et al, issued Mar. 7, 1989.

Compositions herein may also suitably include as a bleach catalyst the class of transition metal complexes of a macropolycyclic rigid ligand. The phrase "macropolycyclic rigid ligand" is sometimes abbreviated as "MRL". One useful MRL is [MnBcyclamCl2], where "Bcyclam" is (5,12-dimethyl-1,5,8,12-tetraaza-bicyclo[6.6.2]hexadecane). See PCT applications PCT/IB98/00298, PCT/IB98/00299, PCT/IB98/00300, and PCT/IB98/00302. The amount used is a catalytically effective amount, suitably about 1 ppb or more, for example up to about 99.9%, more typically about 0.001 ppm or more, preferably from about 0.05 ppm to about 500 ppm (wherein "ppb" denotes parts per billion by weight and "ppm" denotes parts per million by weight).

As a practical matter, and not by way of limitation, the compositions and cleaning processes herein can be adjusted to provide on the order of at least one part per hundred million of the active bleach catalyst species in the aqueous washing medium, and will preferably provide from about 0.01 ppm to about 25 ppm, more preferably from about 0.05 ppm to about 10 ppm, and most preferably from about 0.1 ppm to about 5 ppm, of the bleach catalyst species in the wash liquor. In order to obtain such levels in the wash liquor of an automatic washing process, typical compositions herein will comprise from about 0.0005% to about 0.2%, more preferably from about 0.004% to about 0.08%, of bleach catalyst, especially manganese or cobalt catalysts, by weight of the cleaning compositions.

Enzymatic Sources of Hydrogen Peroxide

On a different track from the bleach activators illustrated hereinabove, another suitable hydrogen peroxide generating system is a combination of a $C_1$–$C_4$ alkanol oxidase and a $C_1$–$C_4$ alkanol, especially a combination of methanol oxidase (MOX) and ethanol. Such combinations are disclosed in WO 94/03003. Other enzymatic materials related to bleaching, such as peroxidases, haloperoxidases, oxidases, superoxide dismutases, catalases and their enhancers or, more commonly, inhibitors, may be used as optional ingredients in the instant compositions.

Oxygen Transfer Agents and Precursors

Also useful herein are any of the known organic bleach catalysts, oxygen transfer agents or precursors therefor. These include the compounds themselves and/or their precursors, for example any suitable ketone for production of dioxiranes and/or any of the hetero-atom containing analogs of dioxirane precursors or dioxiranes, such as sulfonimines $R^1R^2C{=}NSO_2R^3$, see EP 446 982 A, published 1991 and sulfonyloxaziridines, see EP 446,981 A, published 1991. Preferred examples of such materials include hydrophilic or hydrophobic ketones, used especially in conjunction with monoperoxysulfates to produce dioxiranes in situ, and/or the imines described in U.S. Pat. No. 5,576,282 and references described therein. Oxygen bleaches preferably used in conjunction with such oxygen transfer agents or precursors include percarboxylic acids and salts, percarbonic acids and salts, peroxymonosulfuric acid and salts, and mixtures thereof. See also U.S. Pat. No. 5,360,568; U.S. Pat. No. 5,360,569; U.S. Pat. No. 5,370,826 and U.S. Pat. No. 5,442,066.

Although oxygen bleach systems and/or their precursors may be susceptible to decomposition during storage in the presence of moisture, air (oxygen and/or carbon dioxide) and trace metals (especially rust or simple salts or colloidal oxides of the transition metals) and when subjected to light, stability can be improved by adding common sequestrants (chelants) and/or polymeric dispersants and/or a small amount of antioxidant to the bleach system or product. See, for example, U.S. Pat. No. 5,545,349. Antioxidants are often added to detergent ingredients ranging from enzymes to surfactants. Their presence is not necessarily inconsistent with use of an oxidant bleach; for example, the introduction of a phase barrier may be used to stabilize an apparently incompatible combination of an enzyme and antioxidant, on one hand, and an oxygen bleach, on the other. Although commonly known substances can be used as antioxidants, For example see U.S. Pat. Nos. 5,686,014, 5,622,646, 5,055,218, 4,853,143, 4,539,130 and 4,483,778. Preferred antioxidants are 3,5-di-tert-butyl-4-hydroxytoluene, 2,5-di-tert-butylhydroquinone and D,L-alpha-tocopherol.

Polymeric Soil Release Agent—The compositions according to the present invention may optionally comprise one or more soil release agents. Polymeric soil release agents are characterized by having both hydrophilic segments, to hydrophilize the surface of hydrophobic fibers, such as polyester and nylon, and hydrophobic segments, to deposit upon hydrophobic fibers and remain adhered thereto through completion of the laundry cycle and, thus, serve as an anchor for the hydrophilic segments. This can enable stains occurring subsequent to treatment with the soil release agent to be more easily cleaned in later washing procedures.

If utilized, soil release agents will generally comprise from about 0.01% to about 10% preferably from about 0.1% to about 5%, more preferably from about 0.2% to about 3% by weight, of the composition.

The following, all included herein by reference, describe soil release polymers suitable for us in the present invention. U.S. Pat. No. 5,691,298 Gosselink et al., issued Nov. 25, 1997; U.S. Pat. No. 5,599,782 Pan et al., issued Feb. 4, 1997; U.S. Pat. No. 5,415,807 Gosselink et al., issued May 16, 1995; U.S. Pat. No. 5,182,043 Morrall et al., issued Jan. 26, 1993; U.S. Pat. No. 4,956,447 Gosselink et al., issued Sep. 11, 1990; U.S. Pat. No. 4,976,879 Maldonado et al. issued Dec. 11, 1990; U.S. Pat. No. 4,968,451 Scheibel et al., issued Nov. 6, 1990; U.S. Pat. No. 4,925,577 Borcher, Sr. et al., issued May 15, 1990; U.S. Pat. No. 4,861,512 Gosselink, issued Aug. 29, 1989; U.S. Pat. No. 4,877,896 Maldonado et al., issued Oct. 31, 1989; U.S. Pat. No. 4,702,857 Gosselink et al., issued Oct. 27, 1987; U.S. Pat. No. 4,711,730 Gosselink et al., issued Dec. 8, 1987; U.S. Pat. No. 4,721,580 Gosselink issued Jan. 26, 1988; U.S. Pat. No. 4,000,093 Nicol et al., issued Dec. 28, 1976; U.S. Pat. No. 3,959,230 Hayes, issued May 25, 1976; U.S. Pat. No. 3,893,929 Basadur, issued Jul. 8, 1975; and European Patent Application 0 219 048, published Apr. 22, 1987 by Kud et al.

Further suitable soil release agents are described in U.S. Pat. No. 4,201,824 Voilland et al.; U.S. Pat. No. 4,240,918 Lagasse et al.; U.S. Pat. No. 4,525,524 Tung et al.; U.S. Pat. No. 4,579,681 Ruppert et al.; U.S. Pat. No. 4,220,918; U.S. Pat. No. 4,787,989; EP 279,134 A, 1988 to Rhone-Poulenc Chemie; EP 457,205 A to BASF (1991); and DE 2,335,044 to Unilever N.V., 1974; all incorporated herein by reference. Clay Soil Removal/Anti-redeposition Agents—The compositions of the present invention can also optionally contain water-soluble ethoxylated amines having clay soil removal and antiredeposition properties. Granular detergent compositions which contain these compounds typically contain from about 0.01% to about 10.0% by weight of the water-soluble ethoxylated amines; liquid detergent compositions typically contain about 0.01% to about 5%.

A preferred soil release and anti-redeposition agent is ethoxylated tetraethylene pentamine. Exemplary ethoxylated amines are further described in U.S. Pat. No. 4,597,898, VanderMeer, issued Jul. 1, 1986. Another group of preferred clay soil removal-antiredeposition agents are the cationic compounds disclosed in European Patent Application 111,965, Oh and Gosselink, published Jun. 27, 1984. Other clay soil removal/antiredeposition agents which can be used include the ethoxylated amine polymers disclosed in European Patent Application 111,984, Gosselink, published Jun. 27, 1984; the zwitterionic polymers disclosed in European Patent Application 112,592, Gosselink, published Jul. 4, 1984; and the amine oxides disclosed in U.S. Pat. No. 4,548,744, Connor, issued Oct. 22, 1985. Other clay soil removal and/or anti redeposition agents known in the art can also be utilized in the compositions herein. See U.S. Pat. No. 4,891,160, VanderMeer, issued Jan. 2, 1990 and WO 95/32272, published Nov. 30, 1995. Another type of preferred antiredeposition agent includes the carboxy methyl cellulose (CMC) materials. These materials are well known in the art.

Polymeric Dispersing Agents—Polymeric dispersing agents can advantageously be utilized at levels from about 0.1% to about 7%, by weight, in the compositions herein, especially in the presence of zeolite and/or layered silicate builders. Suitable polymeric dispersing agents include polymeric polycarboxylates and polyethylene glycols, although others known in the art can also be used. It is believed, though it is not intended to be limited by theory, that polymeric dispersing agents enhance overall detergent builder performance, when used in combination with other builders (including lower molecular weight polycarboxylates) by crystal growth inhibition, particulate soil release, peptization, and anti-redeposition.

Polymeric polycarboxylate materials can be prepared by polymerizing or copolymerizing suitable unsaturated monomers, preferably in their acid form. Unsaturated monomeric acids that can be polymerized to form suitable polymeric polycarboxylates include acrylic acid, maleic acid (or maleic anhydride), fumaric acid, itaconic acid, aconitic acid, mesaconic acid, citraconic acid and methylenemalonic acid. The presence in the polymeric polycarboxylates herein or monomeric segments, containing no carboxylate radicals such as vinylmethyl ether, styrene, ethylene, etc. is suitable provided that such segments do not constitute more than about 40% by weight.

Particularly suitable polymeric polycarboxylates can be derived from acrylic acid. The average molecular weight of such polymers in the acid form preferably ranges from about 2,000 to 10,000, more preferably from about 4,000 to 7,000 and most preferably from about 4,000 to 5,000. Soluble polymers of this type are known materials. Use of polyacrylates of this type in detergent compositions has been disclosed, for example, in Diehl, U.S. Pat. No. 3,308,067, issued Mar. 7, 1967.

Acrylic/maleic-based copolymers may also be used as a preferred component of the dispersing/anti-redeposition agent. The average molecular weight of such copolymers in the acid form preferably ranges from about 2,000 to 100,000, more preferably from about 5,000 to 75,000, most preferably from about 7,000 to 65,000. The ratio of acrylate to maleate segments in such copolymers will generally range from about 30:1 to about 1:1, more preferably from about 10:1 to 2:1. Soluble acrylate/maleate copolymers of this type are known materials which are described in European Patent Application No. 66915, published Dec. 15, 1982, as well as in EP 193,360, published Sep. 3, 1986, which also describes such polymers comprising hydroxypropylacrylate. Still other useful dispersing agents include the maleic/acrylic/vinyl alcohol terpolymers. Such materials are also disclosed in EP 193,360, including, for example, the 45/45/10 terpolymer of acrylic/maleic/vinyl alcohol.

Another polymeric material which can be included is polyethylene glycol (PEG). PEG can exhibit dispersing agent performance as well as act as a clay soil removal-antiredeposition agent. Typical molecular weight ranges for these purposes range from about 500 to about 100,000, preferably from about 1,000 to about 50,000, more preferably from about 1,500 to about 10,000.

Polyaspartate and polyglutamate dispersing agents may also be used, especially in conjunction with zeolite builders. Dispersing agents such as polyaspartate preferably have a molecular weight (avg.) of about 10,000.

Other polymer types which may be more desirable for biodegradability, improved bleach stability, or cleaning purposes include various terpolymers and hydrophobically modified copolymers, including those marketed by Rohm & Haas, BASF Corp., Nippon Shokubai and others for all manner of water-treatment, textile treatment, or detergent applications.

Brightener—Any optical brighteners or other brightening or whitening agents known in the art can be incorporated at levels typically from about 0.01% to about 1.2%, by weight, into the detergent compositions herein when they are designed for fabric washing or treatment.

Specific examples of optical brighteners which are useful in the present compositions are those identified in U.S. Pat. No. 4,790,856, issued to Wixon on Dec. 13, 1988. These brighteners include the PHORWHITE series of brighteners from Verona. Other brighteners disclosed in this reference include: Tinopal UNPA, Tinopal CBS and Tinopal 5BM; available from Ciba-Geigy; Arctic White CC and Arctic White CWD, the 2-(4-styryl-phenyl)-2H-naptho[1,2-d]triazoles; 4,4'-bis-(1,2,3-triazol-2-yl)-stilbenes; 4,4'-bis (styryl)bisphenyls; and the aminocoumarins. Specific examples of these brighteners include 4-methyl-7-diethyl-amino coumarin; 1,2-bis(benzimidazol-2-yl)ethylene; 1,3-diphenyl-pyrazolines; 2,5-bis(benzoxazol-2-yl)thiophene; 2-styryl-naptho[1,2-d]oxazole; and 2-(stilben-4-yl)-2H-naphtho[1,2-d]triazole. See also U.S. Pat. No. 3,646,015, issued Feb. 29, 1972 to Hamilton.

Polymeric Dye Transfer Inhibiting Agents—The compositions of the present invention may also include one or more materials effective for inhibiting the transfer of dyes from one fabric to another during the cleaning process. Generally, such dye transfer inhibiting agents include polyvinyl pyrrolidone polymers, polyamine N-oxide polymers, copolymers of N-vinylpyrrolidone and N-vinylimidazole, manganese phthalocyanine, peroxidases, and mixtures thereof. If used, these agents typically comprise from about 0.01% to about 10% by weight of the composition, preferably from about 0.01% to about 5%, and more preferably from about 0.05% to about 2%.

The amine N-oxide polymers typically have a ratio of amine to the amine N-oxide of 10:1 to 1:1,000,000. However, the number of amine oxide groups present in the polyamine oxide polymer can be varied by appropriate copolymerization or by an appropriate degree of N-oxidation. The polyamine oxides can be obtained in almost any degree of polymerization. Typically, the average molecular weight is within the range of 500 to 1,000,000; more preferred 1,000 to 500,000; most preferred 5,000 to 100,000. This preferred class of materials can be referred to as "PVNO". See U.S. Pat. No. 5,633,255 to Fredj.

The most preferred polyamine N-oxide useful in the detergent compositions herein is poly(4-vinylpyridine-N-oxide) which as an average molecular weight of about 50,000 and an amine to amine N-oxide ratio of about 1:4.

Copolymers of N-vinylpyrrolidone and N-vinylimidazole polymers (referred to as a class as "PVPVI") are also preferred for use herein. Preferably the PVPVI has an average molecular weight range from 5,000 to 1,000,000, more preferably from 5,000 to 200,000, and most preferably from 10,000 to 20,000. (The average molecular weight range is determined by light scattering as described in Barth, et al., *Chemical Analysis*, Vol. 113. "Modern Methods of Polymer Characterization", the disclosures of which are incorporated herein by reference.) The PVPVI copolymers typically have a molar ratio of N-vinylimidazole to N-vinylpyrrolidone from 1:1 to 0.2:1, more preferably from 0.8:1 to 0.3:1, most preferably from 0.6:1 to 0.4:1. These copolymers can be either linear or branched.

The present invention compositions also may employ a polyvinylpyrrolidone ("PVP") having an average molecular weight of from about 5,000 to about 400,000, preferably from about 5,000 to about 200,000, and more preferably from about 5,000 to about 50,000. PVP's are known to persons skilled in the detergent field; see, for example, EP-A-262,897 and EP-A-256,696, incorporated herein by reference. Compositions containing PVP can also contain polyethylene glycol ("PEG") having an average molecular weight from about 500 to about 100,000, preferably from about 1,000 to about 10,000. Preferably, the ratio of PEG to PVP on a ppm basis delivered in wash solutions is from about 2:1 to about 50:1, and more preferably from about 3:1 to about 10:1.

The detergent compositions herein may also optionally contain from about 0.005% to 5% by weight of certain types of hydrophilic optical brighteners which also provide a dye transfer inhibition action. If used, the compositions herein will preferably comprise from about 0.01% to 1% by weight of such optical brighteners.

The hydrophilic optical brighteners useful in the present invention include, for example 4,4',-bis[(4-anilino-6-(N-2-bis-hydroxyethyl)-s-triazine-2-yl)amino]-2,2'-stilbenedisulfonic acid and disodium salt (Tinopal-UNPA-GX), 4,4'-bis[(4-anilino-6-(N-2-hydroxyethyl-N-methylamino)-s-triazine-2-yl)amino]2,2'-stilbenedisulfonic acid di-sodium salt (Tinopal 5BM-GX) and 4,4'-bis[(4-anilino-6-morphilino-s-triazine-2-yl)amino]2,2'-stilbenedisulfonic acid, sodium salt (Tinopal AMS-GX) all by Ciba Geigy Corporation.

The specific optical brightener species selected for use in the present invention provide especially effective dye transfer inhibition performance benefits when used in combination with the selected polymeric dye transfer inhibiting agents hereinbefore described. The combination of such selected polymeric materials (e.g., PVNO and/or PVPVI) with such selected optical brighteners (e.g., Tinopal UNPA-GX, Tinopal 5BM-GX and/or Tinopal AMS-GX) provides significantly better dye transfer inhibition in aqueous wash solutions than does either of these two detergent composition components when used alone. Without being bound by theory the extent to which brighteners deposit on fabrics in the wash solution can be defined by a parameter called the "exhaustion coefficient". The exhaustion coefficient is in general defined as the ratio of a) the brightener material deposited on fabric to b) the initial brightener concentration in the wash liquor. Brighteners with relatively high exhaustion coefficients are the most suitable for inhibiting dye transfer in the context of the present invention.

Other, conventional optical brightener types can optionally be used in the present compositions to provide conventional fabric "brightness" benefits, rather than a dye transfer inhibiting effect. Such usage is conventional and well-known to detergent formulations.

Chelating Agents—The detergent compositions herein may also optionally contain one or chelating agents, particularly chelating agents for adventitious transition metals. Those commonly found in wash water include iron and/or manganese in water-soluble, colloidal or particulate form, and may be associated as oxides or hydroxides, or found in association with soils such as humic substances. Preferred chelants are those which effectively control such transition metals, especially including controlling deposition of such transition-metals or their compounds on fabrics and/or controlling undesired redox reactions in the wash medium and/or at fabric or hard surface interfaces. Such chelating agents include those having low molecular weights as well as polymeric types, typically having at least one, preferably two or more donor heteroatoms such as O or N, capable of co-ordination to a transition-metal, Common chelating agents can be selected from the group consisting of aminocarboxylates, aminophosphonates, polyfunctionally-substituted aromatic chelating agents and mixtures thereof, all as hereinafter defined.

Aminocarboxylates useful as optional chelating agents include ethylenediaminetetraacetates, N-hydroxyethyl-ethylenediaminetriacetates, nitrilotriacetates, ethylenediamine tetrapropionates, triethylenetetraaminehexaacetates, diethylenetriaminepentaacetates, and ethanoldiglycines, their alkali metal, ammonium, and substituted ammonium salts, and mixtures thereof.

Aminophosphonates are also suitable for use as chelating agents in the compositions of the invention when at least low levels of total phosphorus are permitted in detergent compositions, and include ethylenediaminetetrakis (methylenephosphonates) such as DEQUEST. Preferably, these amino phosphonates do not contain alkyl or alkenyl groups having more than about 6 carbon atoms.

Polyfunctionally-substituted aromatic chelating agents are also useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A preferred biodegradable chelator for use herein is ethylenediamine disuccinate ("EDDS"), especially the [S,S] isomer as described in U.S. Pat. No. 4,704,233, Nov. 3, 1987, to Hartman and Perkins.

The compositions herein may also contain water-soluble methyl glycine diacetic acid (MGDA) salts (or acid form) as a chelant or co-builder useful with, for example, insoluble builders such as zeolites, layered silicates and the like.

If utilized, chelating agents will generally comprise from about 0.001% to about 15% by weight of the detergent compositions herein. More preferably, if utilized, chelating agents will comprise from about 0.01% to about 3.0% by weight of such compositions.

Suds Suppressors—Compounds for reducing or suppressing the formation of suds can be incorporated into the compositions of the present invention when required by the intended use, especially washing of laundry in washing appliances. Other compositions, such as those designed for hand-washing, may desirably be high-sudsing and may omit such ingredients Suds suppression can be of particular importance in the so-called "high concentration cleaning process" as described in U.S. Pat. Nos. 4,489,455 and 4,489,574 and in front-loading European-style washing machines.

A wide variety of materials may be used as suds suppressors and are well known in the art. See, for example, Kirk Othmer Encyclopedia of Chemical Technology, Third Edition, Volume 7, pages 430–447 (Wiley, 1979).

The compositions herein will generally comprise from 0% to about 10% of suds suppressor. When utilized as suds suppressors, monocarboxylic fatty acids, and salts thereof, will be present typically in amounts up to about 5%, preferably 0.5%–3% by weight, of the detergent composition, although higher amounts may be used. Preferably from about 0.01% to about 1% of silicone suds suppressor is used, more preferably from about 0.25% to about 0.5%. These weight percentage values include any silica that may be utilized in combination with polyorganosiloxane, as well as any suds suppressor adjunct materials that may be utilized. Monostearyl phosphate suds suppressors are generally utilized in amounts ranging from about 0.1% to about 2%, by weight, of the composition. Hydrocarbon suds suppressors are typically utilized in amounts ranging from about 0.01% to about 5.0%, although higher levels can be used. The alcohol suds suppressors are typically used at 0.2%–3% by weight of the finished compositions.

Alkoxylated Polycarboxylates—Alkoxylated polycarboxylates such as those prepared from polyacrylates are useful herein to provide additional grease removal performance.

Such materials are described in WO 91/08281 and PCT 90/01815 at p. 4 et seq., incorporated herein by reference. Chemically, these materials comprise polyacrylates having one ethoxy side-chain per every 7–8 acrylate units. The side-chains are of the formula —$(CH_2CH_2O)_m(CH_2)_nCH_3$ wherein m is 2–3 and n is 6–12. The side-chains are ester-linked to the polyacrylate "backbone" to provide a "comb" polymer type structure. The molecular weight can vary, but is typically in the range of about 2000 to about 50,000. Such alkoxylated polycarboxylates can comprise from about 0.05% to about 10%, by weight, of the compositions herein.

Fabric Softeners—Various through-the-wash fabric softeners, especially the impalpable smectite clays of U.S. Pat. No. 4,062,647, Storm and Nirschl, issued Dec. 13, 1977, as well as other softener clays known in the art, can optionally be used typically at levels of from about 0.5% to about 10% by weight in the present compositions to provide fabric softener benefits concurrently with fabric cleaning. Clay softeners can be used in combination with amine and cationic softeners as disclosed, for example, in U.S. Pat. No. 4,375,416, Crisp et al, Mar. 1, 1983 and U.S. Pat. No. 4,291,071, Harris et al, issued Sep. 22, 1981. Moreover, in laundry cleaning methods herein, known fabric softeners, including biodegradable types, can be used in pretreat, mainwash, post-wash and dryer-added modes.

Perfumes—Perfumes and perfumery ingredients useful in the present compositions and processes comprise a wide variety of natural and synthetic chemical ingredients, including, but not limited to, aldehydes, ketones, esters, and the like. Also included are various natural extracts and essences which can comprise complex mixtures of ingredients, such as orange oil, lemon oil, rose extract, lavender, musk, patchouli, balsamic essence, sandalwood oil, pine oil, cedar, and the like. Finished perfumes can comprise extremely complex mixtures of such ingredients. Finished perfumes typically comprise from about 0.01% to about 2%, by weight, of the detergent compositions herein, and individual perfumery ingredients can comprise from about 0.0001% to about 90% of a finished perfume composition.

Non-limiting examples of perfume ingredients useful herein include: 7-acetyl-1,2,3,4,5,6,7,8-octahydro-1,1,6,7-tetramethyl naphthalene; ionone methyl; ionone gamma methyl; methyl cedrylone; methyl dihydrojasmonate; methyl 1,6,10-trimethyl-2,5,9-cyclododecatrien-1-yl ketone; 7-acetyl-1,1,3,4,4,6-hexamethyl tetralin; 4-acetyl-6-tert-butyl-1,1-dimethyl indane; para-hydroxy-phenyl-butanone; benzophenone; methyl beta-naphthyl ketone; 6-acetyl-1,1,2,3,3,5-hexamethyl indane; 5-acetyl-3-isopropyl-1,1,2,6-tetramethyl indane; 1-dodecanal, 4-(4-hydroxy-4-methylpentyl)-3-cyclohexene-1-carboxaldehyde; 7-hydroxy-3,7-dimethyl ocatanal; 10-undecen-1-al; iso-hexenyl cyclohexyl carboxaldehyde; formyl tricyclodecane; condensation products of hydroxy-citronellal and methyl anthranilate, condensation products of hydroxycitronellal and indol, condensation products of phenyl acetaldehyde and indol; 2-methyl-3-(para-tert-butylphenyl)-propionaldehyde; ethyl vanillin; heliotropin; hexyl cinnamic aldehyde; amyl cinnamic aldehyde; 2-methyl-2-(para-iso-propylphenyl)-propionaldehyde; coumarin; decalactone gamma; cyclopentadecanolide; 16-hydroxy-9-hexadecenoic acid lactone; 1,3,4,6,7,8-hexahydro-4,6,6,7,8,8-hexamethylcyclopenta-gamma-2-benzo-pyrane; beta-naphthol methyl ether; ambroxane; dodecahydro-3a,6,6,9a-tetramethyl-naphtho[2,1b]furan; cedrol, 5-(2,2,3-trimethylcyclopent-3-enyl)-3-methylpentan-2-ol; 2-ethyl-4-(2,2,3-trimethyl-3-cyclopenten-1-yl)-2-buten-1-ol; caryophyllene alcohol; tricyclodecenyl propionate; tricyclodecenyl acetate; benzyl salicylate; cedryl acetate; and para-(tert-butyl)cyclohexyl acetate.

Particularly preferred perfume materials are those that provide the largest odor improvements in finished product compositions containing cellulases. These perfumes include but are not limited to: hexyl cinnamic aldehyde; 2-methyl-3-(para-tert-butylphenyl)-propionaldehyde; 7-acetyl-1,2,3,4,5,6,7,8-octahydro-1,1,6,7-tetramethyl naphthalene; benzyl salicylate; 7-acetyl-1,1,3,4,4,6-hexamethyl tetralin; para-tert-butyl cyclohexyl acetate; methyl dihydro jasmonate; beta-napthol methyl ether; methyl beta-naphthyl ketone; 2-methyl-2-(para-iso-propylphenyl)-propionaldehyde; 1,3,4,6,7,8-hexahydro-4,6,6,7,8,8-hexamethyl-cyclopenta-gamma-2-benzopyrane; dodecahydro-3a,6,6,9a-tetramethylnaphtho[2,1b]furan; anisaldehyde; coumarin; cedrol; vanillin; cyclopentadecanolide; tricyclodecenyl acetate; and tricyclodecenyl propionate.

Other perfume materials include essential oils, resinoids, and resins from a variety of sources including, but not limited to: Peru balsam, Olibanum resinoid, styrax, labdanum resin, nutmeg, cassia oil, benzoin resin, coriander and lavandin. Still other perfume chemicals include phenyl ethyl alcohol, terpineol, linalool, linalyl acetate, geraniol, nerol, 2-(1,1-dimethylethyl)-cyclohexanol acetate, benzyl acetate, and eugenol. Carriers such as diethylphthalate can be used in the finished perfume compositions.

Other Detergent Ingredients—A wide variety of other ingredients useful in detergent compositions can be included in the compositions herein, including other active ingredients, carriers, hydrotropes, processing aids, dyes or pigments, solvents for liquid formulations, solid fillers for bar compositions, etc. If high sudsing is desired, suds boosters such as the $C_{10}$–$C_{16}$ alkanolamides can be incorporated into the compositions, typically at 1%–10% levels. The $C_{10}$–$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, water-soluble magnesium and/or calcium salts such as $MgCl_2$, $MgSO_4$, $CaCl_2$, $CaSO_4$ and the like, can be added at levels of, typically, 0.1%–2%, to provide additional suds and to enhance grease removal performance, especially for liquid dishwashing purposes.

Various detersive ingredients employed in the present compositions optionally can be further stabilized by absorbing said ingredients onto a porous hydrophobic substrate, then coating said substrate with a hydrophobic coating. Preferably, the detersive ingredient is admixed with a surfactant before being absorbed into the porous substrate. In use, the detersive ingredient is released from the substrate into the aqueous washing liquor, where it performs its intended detersive function.

Liquid detergent compositions can contain water and other solvents as carriers. Low molecular weight primary or secondary alcohols exemplified by methanol, ethanol, propanol, and isopropanol are suitable. Monohydric alcohols are preferred for solubilizing surfactant, but polyols such as those containing from 2 to about 6 carbon atoms and from 2 to about 6 hydroxy groups (e.g., 1,3-propanediol, ethylene glycol, glycerine, and 1,2-propanediol) can also be used. The compositions may contain from 5% to 90%, typically 10% to 50% of such carriers.

The detergent compositions herein will preferably be formulated such that, during use in aqueous cleaning operations, the wash water will have a pH of between about 6.5 and about 11, preferably between about 7.0 and 10.5, more preferably between about 7.0 to about 9.5. Liquid dishwashing product formulations preferably have a pH between about 6.8 and about 9.0. Laundry products are typically at pH 9–11. Techniques for controlling pH at recommended usage levels include the use of buffers, alkalis, acids, etc., and are well known to those skilled in the art.

Conventional Skin Care Additives

The skin care compositions of the present invention may contain a variety of other ingredients such as are conventionally used in a given product type provided they do not unacceptably alter the benefits of the invention. These optional components should be suitable for application to human skin, that is, when incorporated into the composition they are suitable for use in contact with human skin without undue toxicity, incompatibility, instability, allergic response, and the like within the scope of sound medical or formulator's judgment. The CTFA Cosmetic Ingredient Handbook, Second Edition (1992) describes a wide variety of nonlimiting cosmetic and pharmaceutical ingredients commonly used in the skin care industry, which are suitable for use in the compositions of the present invention. Examples of these ingredient classes include: abrasives, absorbents, aesthetic components such as perfumes, pigments, colorings/colorants, essential oils, skin sensates, astringents, etc. (e.g., clove oil, menthol, camphor, eucalyptus oil, eugenol, menthyl lactate, witch hazel distillate), anti-acne agents (e.g., resorcinol, sulfur, salicylic acid, erythromycin, zinc, etc.), anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), humectants, opacifying agents, pH adjusters, propellants, reducing agents, sequestrants, skin bleaching agents (or lightening agents) (e.g., hydroquinone, kojic acid, ascorbic acid, magnesium ascorbyl phosphate, ascorbyl glucosamine), skin-conditioning agents (humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents including agents for preventing, retarding, arresting, and/or reversing skin wrinkles (e.g., alpha-hydroxy acids such as lactic acid and glycolic acid and beta-hydroxy acids such as salicylic acid), thickeners, and vitamins and derivatives thereof (e.g. tocopherol, tocopherol acetate, retinoic acid, retinol, retinoids, retinyl palmitate, niacin, niacinamide, and the like).

The skin care compositions of the present invention may contain one or more of such optional components. Preferred skin care compositions optionally contain one or more materials selected from UVB sunscreen actives, anti-acne actives, artificial tanning agents, humectants, moisturizers, skin conditioners, and thickening/structuring agents.

UVB Sunscreen Active

The skin care compositions of the present invention can comprise a UVB sunscreen active which absorbs UV radiation having a wavelength of from about 290 nm to about 320 nm. As used herein, the UVB sunscreen active means an active other than the dibenzoylmethane sunscreen active which itself may possess UVB absorption properties. The skin care compositions should comprise an amount of the UVB active effective to provide UVB protection either independently or in combination with other UV protective actives which may be present in the skin care composition, preferably from about 0.1% to about 10%, more preferably from about 0.1% to about 4%, and most preferably from about 0.5% to about 2.5% by weight of the composition.

A wide variety of UVB sunscreen actives, including both organic sunscreen actives and inorganic physical sunblocks, are suitable for use herein. Nonlimiting examples of such sunscreen actives are described in U.S. Pat. No. 5,087,445 issued Feb. 11, 1992 to Haffey et al.; and U.S. Pat. Nos. 5,073,371 and 5,073,372, both issued on Dec. 17, 1991 to Turner et al. Nonlimiting examples of suitable physical sunblocks are described in CTFA International Cosmetic Ingredient Dictionary, Sixth edition, 1995, pp. 1026–28, and 1103.

Preferred UVB sunscreen actives are selected from group consisting of 2-phenyl-benzimidazole-5-sulfonic acid, octocrylene, TEA salicylate, octyl dimethyl PABA, zinc oxide, titanium dioxide, and mixtures thereof. A preferred organic sunscreen active is 2-phenyl-benzimidazole-5-sulfonic acid while preferred inorganic physical sunblocks are zinc oxide, titanium dioxide, and mixtures thereof. Salt and acid-neutralized forms of the acidic sunscreens are also contemplated herein.

When used, the physical sunblocks are present in an amount such that the present skin care compositions are transparent on the skin (i.e., non-whitening), preferably less than or equal to about 5%. When titanium dioxide is used, it can have an anatase, rutile, or amorphous structure. Physical sunblock particles, e.g., titanium dioxide and zinc oxide, can be uncoated or coated with a variety of materials including, but not limited to, amino acids; aluminum compounds such as alumina, aluminum stearate, aluminum laurate, and the like; carboxylic acids and their salts, e.g., stearic acid and its salts; phospholipids such as lecithin; organic silicone compounds; inorganic silicone compounds such as silica and silicates; and mixtures thereof. A preferred titanium dioxide is commercially available from Tayca (Japan) and is distributed by Tri-K Industries (Emerson, N.J.) under the MT micronized series (e.g., MT 100SAS).

Anti-Acne Actives

The skin care compositions of the present invention may comprise one or more anti-acne actives. Examples of useful anti-acne actives are described in further detail in U.S. Pat. No. 5,607,980, issued to McAtee et al., on Mar. 4, 1997.

Artificial Tanning Agents

The skin care compositions of the present invention can comprise one or more artificial tanning agents. Suitable tanning agents include dihydroxyacetone, tyrosine, tyrosine esters and phopho-pho-DOPA. See The Merck Index, Tenth Edition, entry 3167, p. 463 (1983), and "Dihydroxyacetone for Cosmetics", E. Merck Technical Bulletin, 03-304 110, 319 897, 180 588.

Structuring Agent

The skin care compositions of the present invention may contain a structuring agent. Structuring agents are particularly preferred in the oil-in-water emulsions of the present invention. Without being limited by theory, it is believed that the structuring agent assists in providing rheological characteristics to the skin care composition which contribute to the stability of the composition. For example, the structuring agent tends to assist in the formation of the liquid crystalline gel network structures. The structuring agent may also function as an emulsifier or surfactant. Preferred skin care compositions of this invention comprise from about 0.5% to about 20%, more preferably from about 1% to about 10%, most preferably from about 1% to about 5%, of one or more structuring agents.

The preferred structuring agents for use in the skin care compositions of the present invention are selected from the group consisting of stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof. More preferred structuring agents for use in the skin care compositions of the present invention are selected from the group consisting of stearyl alcohol, cetyl alcohol, behenyl alcohol, the polyethylene glycol ether of stearyl alcohol having an average of about 2 ethylene oxide units (steareth-2), the polyethylene glycol ether of stearyl alcohol having an average of about 21 ethylene oxide units (steareth-21), the polyethylene glycol ether of cetyl alcohol having an average of about 2 ethylene oxide units, and mixtures thereof. Even more preferred structuring agents are selected from the group consisting of stearic acid, palmitic acid, stearyl alcohol, cetyl alcohol, behenyl alcohol, steareth-2, steareth-21, and mixtures thereof.

Thickening Agent (Including Thickeners and Gelling Agents)

The skin care compositions of the present invention can comprise one or more thickening agents, preferably from about 0.1% to about 5%, more preferably from about 0.1% to about 3%, and most preferably from about 0.25% to about 2%, by weight of the composition.

Nonlimiting classes of thickening agents include those selected from the group consisting of:

Carboxylic Acid Polymers—These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Polymers useful in the present invention are more fully described in U.S. Pat. No. 5,087,445, to Haffey et al., issued Feb. 11, 1992; U.S. Pat. No. 4,509,949, to Huang et al., issued Apr. 5, 1985; U.S. Pat. No. 2,798,053, to Brown, issued Jul. 2, 1957; and in CTFA International Cosmetic Ingredient Dictionary, Fourth edition, 1991, pp. 12 and 80.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B. F. Goodrich (e.g., Carbopol® 954). In addition, other suitable carboxylic acid polymeric agents include copolymers of $C_{10-30}$ alkyl acrylates with one or more monomers of acrylic acid, methacrylic acid, or one of their short chain (i.e. $C_{1-4}$ alcohol) esters, wherein the crosslinking agent is an allyl ether of sucrose or pentaerytritol. These copolymers are known as acrylates/$C_{10-30}$ alkyl acrylate crosspolymers and are commercially available as Carbopol® 1342, Carbopol® 1382, Pemulen TR-1, and Pemulen TR-2, from B. F. Goodrich. In other words, examples of carboxylic acid polymer thickeners useful herein are those selected from the group consisting of carbomers, acrylates/$C_{10}$–$C_{30}$ alkyl acrylate crosspolymers, and mixtures thereof.

Crosslinked Polyacrylate Polymers—The skin care compositions of the present invention can optionally comprise crosslinked polyacrylate polymers useful as thickeners or gelling agents including both cationic and nonionic polymers, with the cationics being generally preferred. Examples of useful crosslinked nonionic polyacrylate polymers and crosslinked cationic polyacrylate polymers are those described in U.S. Pat. No. 5,100,660, to Hawe et al., issued Mar. 31, 1992; U.S. Pat. No. 4,849,484, to Heard, issued Jul. 18, 1989; U.S. Pat. No. 4,835,206, to Farrar et al., issued May 30, 1989; U.S. Pat. No. 4,628,078 to Glover et al. issued Dec. 9, 1986; U.S. Pat. No. 4,599,379 to Flesher et al. issued Jul. 8, 1986; and EP 228,868, to Farrar et al., published Jul. 15, 1987.

Polyacrylamide Polymers—The skin care compositions of the present invention can optionally comprise polyacrylamide polymers, especially nonionic polyacrylamide polymers including substituted branched or unbranched polymers. Most preferred among these polyacrylamide polymers is the nonionic polymer given the CTFA designation polyacrylamide and isoparaffin and laureth-7, available under the Tradename Sepigel 305 from Seppic Corporation (Fairfield, N.J.).

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc., (Patterson, N.J.).

Polysaccharides—A wide variety of polysaccharides are useful herein. "Polysaccharides" refer to gelling agents which contain a backbone of repeating sugar (i.e. carbohydrate) units. Nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers, the hydroxy groups of the cellulose polymer is hydroxyalkylated (preferably hydroxyethylated or hydroxypropylated) to form a hydroxyalkylated cellulose which is then further modified with a $C_{10}$–$C_{30}$ straight chain or branched chain alkyl group through an ether linkage. Typically these polymers are ethers of $C_{10}$–$C_{30}$ straight or branched chain alcohols with hydroxyalkylcelluloses. Examples of alkyl groups useful herein include those selected from the group consisting of stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation (Wilmington, Del.).

Other useful polysaccharides include scleroglucans comprising a linear chain of (1–3) linked glucose units with a (1–6) linked glucose every three units, a commercially available example of which is Clearogel™ CS11 from Michel Mercier Products Inc. (Mountainside, N.J.).

Gums—Other thickening and gelling agents useful herein include materials which are primarily derived from natural sources. Nonlimiting examples of these gelling agent gums include materials selected from the group consisting of acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

Preferred skin care compositions of the present invention include a thickening agent selected from the group consisting of carboxylic acid polymers, crosslinked polyacrylate polymers, polyacrylamide polymers, and mixtures thereof, more preferably selected from the group consisting of carboxylic acid polymers, polyacrylamide polymers, and mixtures thereof.

Humectants, Moisturizers, and Skin Conditioners

Preferred skin care compositions optionally comprise one or more humectants, moisturizers, or skin conditioners. A variety of these materials can be employed and each can be present at a level of from about 0.01% to about 20%, more preferably from about 0.1% to about 10%, and most preferably from about 0.5% to about 7%. These materials include, but are not limited to, guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy alcohols such as sorbitol, glycerol, hexanetriol, propylene glycol, butylene glycol, hexylene glycol and the like; polyethylene glycols; sugars and starches; sugar and starch derivatives (e.g., alkoxylated glucose); hyaluronic acid; lactamide monoethanolamine; acetamide monoethanolamine; and mixtures thereof. Also useful herein are the propoxylated glycerols described in U.S. Pat. No. 4,976,953, to Orr et al., issued Dec. 11, 1990.

Also useful are various $C_1$–$C_{30}$ monoesters and polyesters of sugars and related materials. These esters are derived from a sugar or polyol moiety and one or more carboxylic acid moieties. Such ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985.

Emulsifiers

The skin care compositions of the present invention can also comprise one or more emulsifiers. Emulsifiers generally serve to reduce the in interfacial tension between phases and improve the formulation and stability of an emulsion. Suitable emulsifiers include a wide variety of nonionic, cationic, anionic, and zwitterionic emulsifiers. See McCutcheon's, Detergents and Emulsifiers, North American Edition (1986), published by Allured Publishing Corporation; U.S. Pat. No. 5,011,681 issued to Ciotti et al. on Apr. 30, 1991; U.S. Pat. No. 4,421,769 issued to Dixon et al. on Dec. 20, 1983; and U.S. Pat. No. 3,755,560 issued to Dickert et al. on Aug. 28, 1973.

Suitable emulsifier types include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps and mixtures thereof.

Suitable emulsifiers can include, but are not limited to, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof. Preferred emulsifiers are steareth-2, steareth-21, TEA stearate, diethanolamine cetyl phosphate, potassium cetyl phosphate, and mixtures thereof. The emulsifier can be used individually or as a mixture of two or more and comprises from about 0.1% to about 10%, more preferably from about 0.15% to about 7%, and most preferably from about 0.25% to about 5% of the compositions of the present invention.

Conventional Personal Cleansing Additive

These are additives which are conventionally used in personal cleansing compositions, such as toilet soaps, body washes, shampoos and medicated wipes. Examples of these are conditioning agents, conventional personal care polymer, antidandruff agent, surfactant; and mixtures thereof. These conventional personal cleansing additives are just some of the possible ingredients which can be conventionally added to personal cleansing compositions.

The conditioning agents, useful in the present invention can be further selected from the group comprising nonvolatile hydrocarbons conditioning agents, silicone conditioning agents and mixtures thereof.

The conventional personal care polymers useful in the present invention can be further selected from the group comprising deposition polymers, styling polymers and solvent, dispersed phase polymers, and mixtures thereof.

The personal cleansing compositions of the present invention is in the form of a liquid or a liquid gel. It can contain for example, suspended ingredients, more than one phase etc. Effectively the personal cleansing compositions of the present invention can be in the form of any type of liquid or liquid gel and contain any additive conventionally added to personal cleansing compositions, such as shampoos, body wash gels, bath gels etc.

For more information and additional examples of conventional personal cleansing additives see copending U.S. Patent Application No. 60/061,916, filed on Oct. 14, 1997 and U.S. Patent Application No. 60/061,975, filed on Oct. 14, 1997, both assigned to Procter & Gamble.

Suitable conventional personal cleansing additives include anti static agents, dyes, diluents, emollient oils (such as polyisobutylene, mineral oil, petrolatum and isocetyl stearyl stearate), pearlescent aids, foam boosters, styling polymer, pediculocides, dispersed phase polymers, hydrotropes, hair or skin conditioning agents such as nonvolatile silicone conditioning agents and nonvolatile organic conditioning agents, solvent pH adjusting agents, perfumes, preservatives, low viscosity surfactant soluble conditioning oil, electrolytes, amphiphiles, proteins, phase separation initiator, cationic spreading agents, such as cationic surfactants, antioxidants; chelators and sequestrants, surfactants, antidandruff agent such as platelet pyridinethione salt crystal, sulfur, octopirox, selenium sulfide, ketoconazole and pyridinethione salts, organic deposition polymers and aesthetic components such as fragrances, colorings, essential oils, skin sensates, astringents, suspending agent skin soothing agents, aqueous liquid carrier, skin healing agents and the like, nonlimiting examples of these aesthetic components include panthenol and derivatives (e.g. ethyl panthenol), pantothenic acid and its derivatives, clove oil, menthol, camphor, eucalyptus oil, eugenol, menthyl lactate, witch hazel distillate, allantoin, (?)bisabolol, dipotassium glycyrrhizinate and the like, sunscreens, thickeners, vitamins and derivatives thereof (e.g., ascorbic acid, vitamin E, tocopheryl acetate, retinoic acid, retinol, retinoids, and the like), and viscosity adjusting agents. This list of conventional personal cleansing additives is not meant to be exclusive, and other conventional personal cleansing additives can be used.

For more information and additional examples of conditioning agents see copending U.S. patent application Ser. No. 08/733,046, filed on Oct. 16, 1996 and U.S. patent application Ser. No. 08/738,156, filed on Oct. 25, 1996. See also U.S. Pat. No. 4,741,855. All three of these references are incorporated herein by reference.

Suitable suspending agents are described in U.S. Pat. Nos. 4,741,855, 4,788,006, 2,798,053, and 4,704,272, which description is incorporated herein by reference.

For suitable deposition polymers see copending U.S. patent application Ser. No. 08/852,166, filed May 6, 1997, Ser. No. 08/738,156 filed on Oct. 25, 1996; and 60/053,319 filed on Jul. 21, 1997 (above), all of which are incorporated herein by reference.

See copending U.S. patent applications Ser. No. 08/738, 211, filed on Oct. 25, 1996 and No. 60/053,319, filed on Jul. 21, 1997, both of which are incorporated herein by reference.

Examples of some suitable styling polymers are described in U.S. Pat. No. 5,120,531, to Wells et al., issued Jun. 9, 1992; U.S. Pat. No. 5,120,532, to Wells et al., issued Jun. 9, 1992; U.S. Pat. No. 5,104,642, to Wells et al., issued Apr. 14, 1992; U.S. Pat. No. 4,272,511, to Papantoniou et al., issued Jun. 9, 1981; U.S. Pat. No. 4,963,348, to Bolich et al., issued Oct. 16, 1990, EPO Application 90307528.1, published as EPO Application 0 408 311 A2 on Jan. 11, 1991, Hayama, et al.; U.S. Pat. No. 5,061,481, issued Oct. 29, 1991, Suzuki et al.; U.S. Pat. No. 5,106,609, Bolich et al., issued Apr. 21, 1992; U.S. Pat. No. 5,100,658, Bolich et al., issued Mar. 31, 1992; U.S. Pat. No. 5,100,657, Ansher-Jackson, et al., issued Mar. 31, 1992; U.S. Pat. No. 5,104,646, Bolich et al., issued Apr. 14, 1992; U.S. Ser. No. 07/758,319, Bolich et al, filed Aug. 27, 1991, U.S. Ser. No. 07/758,320, Torgerson et al., filed Aug. 27, 1991, and U.S. Pat. No. 4,196,190, to Gehman et al., issued Apr. 1, 1980, which descriptions are incorporated herein by reference.

For suitable dispersed phase polymer see also copending U.S. patent application Ser. No. 08/786,521, filed on Jan. 21, 1997, which is incorporated herein by reference.

For suitable phase separation initiators see copending U.S. Patent applications No. 60/061,916, filed on Oct. 14, 1997 and U.S. Patent applications No. 60/061,975, filed on Oct. 14, 1996, both assigned to Procter & Gamble.

For suitable antidandruff agents see also U.S. Pat. No. 4,948,576 to Verdicchio et al, and copending U.S. patent application Ser. No. 08/738,211, filed on Oct. 25, 1996, Ser. No. 08/622,222, filed on Mar. 27, 1996, Ser. No. 08/975,210, filed Nov. 20, 1997, U.S. Pat. Nos. 4,379,753, 2,694,668, 3,152,046, 4,089,945, 4,885,107, 2,809,971, 3,236,733, 3,753,196, 3,761,418, 4,345,080, 4,323,683, 4,379,753 and 4,470,982 all of which are incorporated herein by reference.

Optional Fabric Softener Ingredients

The fabric softening composition of the invention can also contain optional ingredients. A comprehensive list of possible optional ingredients can be found in U.S. Pat. No. 5,747,443, which is incorporated herein by reference.

Low molecular weight water soluble solvents—can also be used at levels of from 0% to about 12%, preferably from about 1% to about 10%, more preferably from about 2% to about 8%. The water soluble solvents cannot provide a clear product at the same low levels of the principal solvents described hereinbefore but can provide clear product when the principal solvent is not sufficient to provide completely clear product. The presence of these water soluble solvents is therefore highly desirable. Such solvents include: ethanol; isopropanol; 1,2-propanediol; 1,3-propanediol; propylene carbonate; etc. but do not include any of the principal solvents (B). These water soluble solvents have a greater affinity for water in the presence of hydrophobic materials like the softener active than the principal solvents.

Brighteners—The fabric softening compositions herein can also optionally contain from about 0.005% to 5% by weight of certain types of hydrophilic optical brighteners which also provide a dye transfer inhibition action. If used, the compositions herein will preferably comprise from about 0.001% to 1% by weight of such optical brighteners.

The hydrophilic optical brighteners useful in the present invention are those having the structural formula:

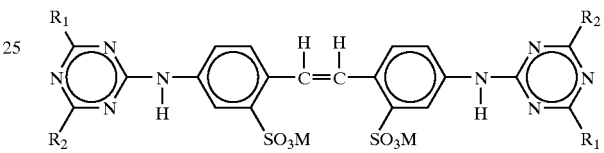

wherein $R_1$ is selected from anilino, N-2-bis-hydroxyethyl and NH-2-hydroxyethyl; $R_2$ is selected from N-2-bis-hydroxyethyl, N-2-hydroxyethyl-N-methylamino, morphilino, chloro and amino; and M is a salt-forming cation such as sodium or potassium.

When in the above formula, $R_1$ is anilino, $R_2$ is N-2-bis-hydroxyethyl and M is a cation such as sodium, the brightener is 4,4',-bis[(4-anilino-6-(N-2-bis-hydroxyethyl)-s-triazine-2-yl)amino]-2,2'-stilbenedisulfonic acid and disodium salt. This particular brightener species is commercially marketed under the tradename Tinopal-UNPA-GX® by Ciba-Geigy Corporation. Tinopal-UNPA-GX is the preferred hydrophilic optical brightener useful in the rinse added compositions herein.

When in the above formula, $R_1$ is anilino, $R_2$ is N-2-hydroxyethyl-N-2-methylamino and M is a cation such as sodium, the brightener is 4,4'-bis[(4-anilino-6-(N-2-hydroxyethyl-N-methylamino)-s-triazine-2-yl)amino]2,2'-stibenedisulfonic acid disodium salt. This particular brightener species is commercially marketed under the tradename Tinopal 5BM-GX® by Ciba-Geigy Corporation.

When in the above formula, $R_1$ is anilino, $R_2$ is morphilino and M is a cation such as sodium, the brightener is 4,4'-bis[(4-anilino-6-morphilino-s-triazine-2-yl)amino]2,2'-stilbenedisulfonic acid, sodium salt. This particular brightener species is commercially marketed under the tradename Tinopal AMS-GX® by Ciba Geigy Corporation.

Dispersibility Aids

Optional Viscosity/Dispersibility Modifiers—Relatively concentrated fabric softening compositions containing both saturated and unsaturated diester quaternary ammonium compounds can be prepared that are stable without the addition of concentration aids. However, the fabric softening compositions of the present invention may require organic and/or inorganic concentration aids to go to even higher concentrations and/or to meet higher stability standards depending on the other ingredients. These concentration aids which typically can be viscosity modifiers may be needed, or preferred, for ensuring stability under extreme conditions when particular softener active levels are used. The surfactant concentration aids are typically selected from the group consisting of (1) single long chain alkyl cationic surfactants; (2) nonionic surfactants; (3) amine oxides; (4) fatty acids; and (5) mixtures thereof. These aids are described in P&G Copending application Ser. No. 08/461,207, filed Jun. 5, 1995, Wahl et al., specifically on page 14, line 12 to page 20, line 12, which is herein incorporated by reference.

When said dispersibility aids are present, the total level is from about 2% to about 25%, preferably from about 3% to about 17%, more preferably from about 4% to about 15%, and even more preferably from 5% to about 13% by weight of the composition. These materials can either be added as part of the active softener raw material e.g., the mono-long chain alkyl cationic surfactant and/or the fatty acid which are reactants used to form the biodegradable fabric softener active as discussed hereinbefore, or added as a separate component.

Mono-Alkyl Cationic Quaternary Ammonium Compound—When the mono-alkyl cationic quaternary ammonium compound is present, it is typically present at a level of from about 2% to about 25%, preferably from about 3% to about 17%, more preferably from about 4% to about 15%, and even more preferably from 5% to about 13% by weight of the composition, the total mono-alkyl cationic quaternary ammonium compound being at least at an effective level.

Such mono-alkyl cationic quaternary ammonium compounds useful in the present invention are, preferably, quaternary ammonium salts of the general formula:

$$[R^4N^+(R^5)_3]X^-$$

wherein $R^4$ is $C_8$–$C_{22}$ alkyl or alkenyl group, preferably $C_{10}$–$C_{18}$ alkyl or alkenyl group; more preferably $C_{10}$–$C_{14}$ or $C_{16}$–$C_{18}$ alkyl or alkenyl group; each $R^5$ is a $C_1$–$C_6$ alkyl or substituted alkyl group (e.g., hydroxy alkyl), preferably $C_1$–$C_3$ alkyl group, e.g., methyl (most preferred), ethyl, propyl, and the like, a benzyl group, hydrogen, a polyethoxylated chain with from about 2 to about 20 oxyethylene units, preferably from about 2.5 to about 13 oxyethylene units, more preferably from about 3 to about 10 oxyethylene units, and mixtures thereof; and $X^-$ is as defined hereinbefore.

Especially preferred dispersibility aids are monolauryl trimethyl ammonium chloride and monotallow trimethyl ammonium chloride available from Witco under the trade name Varisoft® 471 and monooleyl trimethyl ammonium chloride available from Witco under the tradename Varisoft® 417.

The $R^4$ group can also be attached to the cationic nitrogen atom through a group containing one, or more, ester, amide, ether, amine, etc., linking groups which can be desirable for increased concentratability of fabric softening compositions components. Such linking groups are preferably within from about one to about three carbon atoms of the nitrogen atom.

Mono-alkyl cationic quaternary ammonium compounds also include $C_8$–$C_{22}$ alkyl choline esters. The preferred dispersibility aids of this type have the formula:

$$R^1C(O)\text{—}O\text{—}CH_2CH_2N^+(R)_3X^-$$

wherein $R^1$, R and $X^-$ are as defined previously.

Highly preferred dispersibility aids include $C_{12}$–$C_{14}$ coco choline ester and $C_{16}$–$C_{18}$ tallow choline ester.

Suitable biodegradable single-long-chain alkyl dispersibility aids containing an ester linkage in the long chains are described in U.S. Pat. No. 4,840,738, Hardy and Walley, issued Jun. 20, 1989, said patent being incorporated herein by reference.

When the dispersibility aid comprises alkyl choline esters, preferably the compositions also contain a small amount, preferably from about 2% to about 5% by weight of the composition, of organic acid. Organic acids are described in European Patent Application No. 404,471, Machin et al., published on Dec. 27, 1990, supra, which is herein incorporated by reference. Preferably the organic acid is selected from the group consisting of glycolic acid, acetic acid, citric acid, and mixtures thereof.

Ethoxylated quaternary ammonium compounds which can serve as the dispersibility aid include ethylbis (polyethoxy ethanol)alkylammonium ethyl-sulfate with 17 moles of ethylene oxide, available under the trade name Variquat® 66 from Sherex Chemical Company; polyethylene glycol (15) oleammonium chloride, available under the trade name Ethoquad® O/25 from Akzo; and polyethylene glycol (15) cocomonium chloride, available under the trade name Ethoquad® C/25 from Akzo.

Although the main function of the dispersibility aid is to increase the dispersibility of the ester softener, preferably the dispersibility aids of the present invention also have some softening properties to boost softening performance of the composition. Therefore, preferably the compositions of the present invention are essentially free of non-nitrogenous ethoxylated nonionic dispersibility aids which will decrease the overall softening performance of the compositions.

Also, quaternary compounds having only a single long alkyl chain, can protect the cationic softener from interacting with anionic surfactants and/or detergent builders that are carried over into the rinse from the wash solution.

Amine Oxides—Suitable amine oxides include those with one alkyl or hydroxyalkyl moiety of about 8 to about 22 carbon atoms, preferably from about 10 to about 18 carbon atoms, more preferably from about 8 to about 14 carbon atoms, and two alkyl moieties selected from the group consisting of alkyl groups and hydroxyalkyl groups with about 1 to about 3 carbon atoms.

Examples include dimethyloctylamine oxide, diethyldecylamine oxide, bis-(2-hydroxyethyl)dodecyl-amine oxide, dimethyldodecylamine oxide, dipropyltetradecylamine oxide, methylethylhexadecylamine oxide, dimethyl-2-hydroxyoctadecylamine oxide, and coconut fatty alkyl dimethylamine oxide.

Stabilizers—Stabilizers can be present in the fabric softening compositions of the present invention. The term "stabilizer," as used herein, includes antioxidants and reductive agents. These agents are present at a level of from 0% to about 2%, preferably from about 0.01% to about 0.2%, more preferably from about 0.035% to about 0.1% for antioxidants, and more preferably from about 0.01% to about 0.2% for reductive agents. These assure good odor stability under long term storage conditions. Antioxidants and reductive agent stabilizers are especially critical for unscented or low scent products (no or low perfume).

Examples of antioxidants that can be added to the compositions of this invention include a mixture of ascorbic acid, ascorbic palmitate, propyl gallate, available from Eastman Chemical Products, Inc., under the trade names Tenox® PG and Tenox® S-1; a mixture of BHT (butylated hydroxytoluene), BHA (butylated hydroxyanisole), propyl gallate, and citric acid, available from Eastman Chemical Products, Inc., under the trade name Tenox®-6; butylated hydroxytoluene, available from UOP Process Division under the trade name Sustane® BHT; tertiary butylhydroquinone, Eastman Chemical Products, Inc., as Tenox® TBHQ; natural tocopherols, Eastman Chemical Products, Inc., as Tenox® GT-1/GT-2; and butylated hydroxyanisole, Eastman Chemical Products, Inc., as BHA; long chain esters (C8–C22) of gallic acid, e.g., dodecyl gallate; Irganox® 1010; Irganox® 1035; Irganox® B 1171; Irganox® 1425; Irganox® 3114; Irganox® 3125; and mixtures thereof; preferably Irganox® 3125, Irganox® 1425, Irganox® 3114, and mixtures thereof; more preferably Irganox® 3125 alone or mixed with citric acid and/or other chelators such as isopropyl citrate, Dequest® 2010, available from Monsanto with a chemical name of 1-hydroxyethylidene-1,1-diphosphonic acid (etidronic acid), and Tiron®, available from Kodak with a chemical name of 4,5-dihydroxy-m-benzenesulfonic acid/sodium salt, and DTPA®, available from Aldrich with a chemical name of diethylenetriaminepentaacetic acid.

Soil Release Agent—In the present fabric softening compositions, an optional soil release agent can be added. The addition of the soil release agent can occur in combination with the premix, in combination with the acid/water seat, before or after electrolyte addition, or after the final composition is made. The softening composition prepared by the process of the present invention herein can contain from 0% to about 10%, preferably from 0.2% to about 5%, of a soil release agent. Suitable soil release agents are described hereinbefore.

Examples of suitable soil release agents include the commercially available materials Zelcon 4780® (from Dupont) and Milease T® (from ICI).

A more complete disclosure of soil release agents is contained in U.S. Pat. No. 4,661,267, Decker, Konig, Straathof, and Gosselink, issued Apr. 28, 1987; U.S. Pat. No. 4,711,730, Gosselink and Diehl, issued Dec. 8, 1987; U.S. Pat. No. 4,749,596, Evans, Huntington, Stewart, Wolf, and Zimmerer, issued Jun. 7, 1988; U.S. Pat. No. 4,818,569, Trinh, Gosselink, and Rattinger, issued Apr. 4, 1989; U.S. Pat. No. 4,877,896, Maldonado, Trinh, and Gosselink, issued Oct. 31, 1989; U.S. Pat. No. 4,956,447, Gosselink et al., issues Sep. 11, 1990; and U.S. Pat. No. 4,976,879, Maldonado, Trinh, and Gosselink, issued Dec. 11, 1990, all of said patents being incorporated herein by reference.

These soil release agents can also act as scum dispersants.

Scum Dispersant—In the present invention, the premix can be combined with an optional scum dispersant, other than the soil release agent, and heated to a temperature at or above the melting point(s) of the components.

The preferred scum dispersants herein are formed by highly ethoxylating hydrophobic materials. The hydrophobic material can be a fatty alcohol, fatty acid, fatty amine, fatty acid amide, amine oxide, quaternary ammonium compound, or the hydrophobic moieties used to form soil release polymers. The preferred scum dispersants are highly ethoxylated, e.g., more than about 17, preferably more than about 25, more preferably more than about 40, moles of ethylene oxide per molecule on the average, with the polyethylene oxide portion being from about 76% to about 97%, preferably from about 81% to about 94%, of the total molecular weight.

The level of scum dispersant is sufficient to keep the scum at an acceptable, preferably unnoticeable to the consumer, level under the conditions of use, but not enough to adversely affect softening. For some purposes it is desirable that the scum is nonexistent. Depending on the amount of anionic or nonionic detergent, etc., used in the wash cycle of a typical laundering process, the efficiency of the rinsing steps prior to the introduction of the compositions herein, and the water hardness, the amount of anionic or nonionic detergent surfactant and detergency builder (especially phosphates and zeolites) entrapped in the fabric (laundry) will vary. Normally, the minimum amount of scum dispersant should be used to avoid adversely affecting softening properties. Typically scum dispersion requires at least about 2%, preferably at least about 4% (at least 6% and preferably at least 10% for maximum scum avoidance) based upon the level of softener active. However, at levels of about 10% (relative to the softener material) or more, one risks loss of softening efficacy of the product especially when the fabrics contain high proportions of nonionic surfactant which has been absorbed during the washing operation.

Preferred scum dispersants are: Brij 700®; Varonic U-250®; Genapol T-500®, Genapol T-800®; Plurafac A-79®; and Neodol 25–50®.

Bactericides—Examples of bactericides used in the compositions of this invention include glutaraldehyde, formaldehyde, 2-bromo-2-nitro-propane-1,3-diol sold by Inolex Chemicals, located in Philadelphia, Pa., under the trade name Bronopol®, and a mixture of 5-chloro-2-methyl-4-isothiazoline-3-one and 2-methyl-4-isothiazoline-3-one sold by Rohm and Haas Company under the trade name Kathon about 1 to about 1,000 ppm by weight of the agent.

Perfume—The present invention can contain any softener compatible perfume. Suitable perfumes are disclosed in U.S. Pat. No. 5,500,138, Bacon et al., issued Mar. 19, 1996, said patent being incorporated herein by reference.

As used herein, perfume includes fragrant substance or mixture of substances including natural (i.e., obtained by extraction of flowers, herbs, leaves, roots, barks, wood, blossoms or plants), artificial (i.e., a mixture of different nature oils or oil constituents) and synthetic (i.e., synthetically produced) odoriferous substances. Such materials are often accompanied by auxiliary materials, such as fixatives, extenders, stabilizers and solvents. These auxiliaries are also included within the meaning of "perfume", as used herein. Typically, perfumes are complex mixtures of a plurality of organic compounds. Other suitable perfumes are described hereinbefore.

Examples of perfume ingredients useful in the perfumes of the present invention compositions include, but are not limited to, hexyl cinnamic aldehyde; amyl cinnamic aldehyde; amyl salicylate; hexyl salicylate; terpineol; 3,7-dimethyl-cis-2,6-octadien-1-ol; 2,6-dimethyl-2-octanol; 2,6-dimethyl-7-octen-2-ol; 3,7-dimethyl-3-octanol; 3,7-dimethyl-trans-2,6-octadien-1-ol; 3,7-dimethyl-6-octen-1-ol; 3,7-dimethyl-1-octanol; 2-methyl-3-(para-tert-butylphenyl)-propionaldehyde; 4-(4-hydroxy-4-methylpentyl)-3-cyclohexene-1-carboxaldehyde; tricyclodecenyl propionate; tricyclodecenyl acetate; anisaldehyde; 2-methyl-2-(para-iso-propylphenyl)-propionaldehyde; ethyl-3-methyl-3-phenyl glycidate; 4-(para-hydroxyphenyl)-butan-2-one; 1-(2,6,6-trimethyl-2-cyclohexen-1-yl)-2-buten-1-one; para-methoxyacetophenone; para-methoxy-alpha-phenylpropene; methyl-2-n-hexyl-3-oxo-cyclopentane carboxylate; undecalactone gamma.

Additional examples of fragrance materials include, but are not limited to, orange oil; lemon oil; grapefruit oil; bergamot oil; clove oil; dodecalactone gamma; methyl-2-(2-pentyl-3-oxo-cyclopentyl)acetate; beta-naphthol methylether; methyl-beta-naphthylketone; coumarin; decylaldehyde; benzaldehyde; 4-tert-butylcyclohexyl acetate; alpha, alpha-dimethylphenethyl acetate; methylphenylcarbinyl acetate; Schiff's base of 4-(4-hydroxy-4-methylpentyl)-3-cyclohexene-1-carboxaldehyde and methyl anthranilate;

cyclic ethyleneglycol diester of tridecandioic acid; 3,7-dimethyl-2,6-octadiene-1-nitrile; ionone gamma methyl; ionone alpha; ionone beta; petitgrain; methyl cedrylone; 7-acetyl-2,3,4,5,6,7,8-octahydro-1,1,6,7-tetramethyl-naphthalene; ionone methyl; methyl-1,6,10-trimethyl-2,5,9-cyclododecatrien-1-yl ketone; 7-acetyl-1,1,3,4,4,6-hexamethyl tetralin; 4-acetyl-6-tert-butyl-1,1-dimethyl indane; benzophenone; 6-acetyl-1,1,2,3,3,5-hexamethyl indane; 5-acetyl-3-isopropyl-1,1,2,6-tetramethyl indane; 1-dodecanal; 7-hydroxy-3,7-dimethyl octanal; 10-undecen-1-al; iso-hexenyl cyclohexyl carboxaldehyde; formyl tricyclodecan; cyclopentadecanolide; 16-hydroxy-9-hexadecenoic acid lactone; 1,3,4,6,7,8-hexahydro-4,6,6,7,8,8-hexamethylcyclopenta-gamma-2-benzopyrane; ambroxane; dodecahydro-3a,6,6,9a-tetramethylnaphtho-[2,1b]furan; cedrol; 5-(2,2,3-trimethylcyclopent-3-enyl)-3-methylpentan-2-ol; 2-ethyl-4-(2,2,3-trimethyl-3-cyclopenten-1-yl)-2-buten-1-ol; caryophyllene alcohol; cedryl acetate; para-tert-butylcyclohexyl acetate; patchouli; olibanum resinoid; labdanum; vetivert; copaiba balsam; fir balsam; and condensation products of: hydroxycitronellal and methyl anthranilate; hydroxycitronellal and indol; phenyl acetaldehyde and indol; 4-(4-hydroxy-4-methyl pentyl)-3-cyclohexene-1-carboxaldehyde and methyl anthranilate.

More examples of perfume components are geraniol; geranyl acetate; linalool; linalyl acetate; tetrahydrolinalool; citronellol; citronellyl acetate; dihydromyrcenol; dihydromyrcenyl acetate; tetrahydromyrcenol; terpinyl acetate; nopol; nopyl acetate; 2-phenylethanol; 2-phenylethyl acetate; benzyl alcohol; benzyl acetate; benzyl salicylate; benzyl benzoate; styrallyl acetate; dimethylbenzylcarbinol; trichloromethylphenylcarbinyl methylphenylcarbinyl acetate; isononyl acetate; vetiveryl acetate; vetiverol; 2-methyl-3-(p-tert-butylphenyl)-propanal; 2-methyl-3-(p-isopropylphenyl)-propanal; 3-(p-tert-butylphenyl)-propanal; 4-(4-methyl-3-pentenyl)-3-cyclohexenecarbaldehyde; 4-acetoxy-3-pentyltetrahydropyran; methyl dihydrojasmonate; 2-n-heptylcyclopentanone; 3-methyl-2-pentyl-cyclopentanone; n-decanal; n-dodecanal; 9-decenol-1; phenoxyethyl isobutyrate; phenylacetaldehyde dimethylacetal; phenylacetaldehyde diethylacetal; geranonitrile; citronellonitrile; cedryl acetal; 3-isocamphylcyclohexanol; cedryl methylether; isolongifolanone; aubepine nitrile; aubepine; heliotropine; eugenol; vanillin; diphenyl oxide; hydroxycitronellal ionones; methyl iononess; isomethyl ionones; irones; cis-3-hexenol and esters thereof; indane musk fragrances; tetralin musk fragrances; isochroman musk fragrances; macrocyclic ketones; macrolactone musk fragrances; ethylene brassylate.

The perfumes useful in the present invention compositions are substantially free of halogenated materials and nitromusks.

Suitable solvents, diluents or carriers for perfumes ingredients mentioned above are for examples, ethanol, isopropanol, diethylene glycol, monoethyl ether, dipropylene glycol, diethyl phthalate, triethyl citrate, etc. The amount of such solvents, diluents or carriers incorporated in the perfumes is preferably kept to the minimum needed to provide a homogeneous perfume solution.

Perfume can be present at a level of from 0% to about 10%, preferably from about 0.1% to about 5%, and more preferably from about 0.2% to about 3%, by weight of the finished composition. Fabric softener compositions of the present invention provide improved fabric perfume deposition.

Chelating Agents—The compositions and processes herein can optionally employ one or more copper and/or nickel chelating agents ("chelators"). Such water-soluble chelating agents can be selected from the group consisting of amino carboxylates, amino phosphonates, polyfunctionally-substituted aromatic chelating agents and mixtures thereof, all as hereinafter defined. The whiteness and/or brightness of fabrics are substantially improved or restored by such chelating agents and the stability of the materials in the compositions are improved. Suitable chelating agents are described hereinbefore.

Amino carboxylates useful as chelating agents herein include ethylenediaminetetraacetates (EDTA), N-hydroxyethylethylenediaminetriacetates, nitrilotriacetates (NTA), ethylenediamine tetraprorionates, ethylenediamine-N,N'-diglutamates, 2-hyroxypropylenediamine-N,N'-disuccinates, triethylenetetraamine-hexacetates, diethylenetriaminepentaacetates (DETPA), and ethanoldiglycines, including their water-soluble salts such as the alkali metal, ammonium, and substituted ammonium salts thereof and mixtures thereof.

Amino phosphonates are also suitable for use as chelating agents in the compositions of the invention when at least low levels of total phosphorus are permitted in detergent compositions, and include ethylenediaminetetrakis (methylenephosphonates), diethylenetriamine-N,N,N',N", N"-pentakis(methane phosphonate) (DETMP) and 1-hydroxyethane-1,1-diphosphonate (HEDP). Preferably, these amino phosphonates to not contain alkyl or alkenyl groups with more than about 6 carbon atoms.

The chelating agents are typically used in the present rinse process at levels from about 2 ppm to about 25 ppm, for periods from 1 minute up to several hours' soaking.

The preferred EDDS chelator used herein (also known as ethylenediamine-N,N'-disuccinate) is the material described in U.S. Pat. No. 4,704,233, cited hereinabove.

As can be seen from the foregoing, a wide variety of chelators can be used herein. Indeed, simple polycarboxylates such as citrate, oxydisuccinate, and the like, can also be used, although such chelators are not as effective as the amino carboxylates and phosphonates, on a weight basis. Accordingly, usage levels may be adjusted to take into account differing degrees of chelating effectiveness. The chelators herein will preferably have a stability constant (of the fully ionized chelator) for copper ions of at least about 5, preferably at least about 7. Typically, the chelators will comprise from about 0.5% to about 10%, more preferably from about 0.75% to about 5%, by weight of the compositions herein. Preferred chelators include DETMP, DETPA, NTA, EDDS and mixtures thereof.

Other Optional Ingredients—The present invention can include optional components conventionally used in textile treatment compositions, for example: colorants; preservatives; surfactants; anti-shrinkage agents; fabric crisping agents; spotting agents; germicides; fungicides; antioxidants such as butylated hydroxy toluene, anti-corrosion agents, and the like.

Particularly preferred ingredients include water soluble calcium and/or magnesium compounds, which provide additional stability. The chloride salts are preferred, but acetate, nitrate, etc. salts can be used. The level of said calcium and/or magnesium salts is from 0% to about 2%, preferably from about 0.05% to about 0.5%, more preferably from about 0.1% to about 0.25%.

The present invention can also include other compatible ingredients, including those as disclosed in copending application Ser. No. 08/372,068, filed Jan. 12, 1995, Rusche, et al.; Ser. No. 08/372,490, filed Jan. 12, 1995, Shaw, et al.; and Ser. No. 08/277,558, filed Jul. 19, 1994, Hartman, et al., incorporated herein by reference.

Form of the Cleaning Compositions

The cleaning compositions in accordance with the invention can take a variety of physical forms including granular, gel, tablet, bar, paste, cream and liquid forms. The form can be dependent upon the end use of the composition. The compositions include the so-called concentrated granular detergent compositions adapted to be added to a washing machine by means of a dispensing device placed in the machine drum with the soiled fabric load.

The mean particle size of the components of granular compositions in accordance with the invention should preferably be such that no more that 5% of particles are greater than 1.7 mm in diameter and not more than 5% of particles are less than 0.15 mm in diameter.

The term mean particle size as defined herein is calculated by sieving a sample of the composition into a number of fractions (typically 5 fractions) on a series of Tyler sieves. The weight fractions thereby obtained are plotted against the aperture size of the sieves. The mean particle size is taken to be the aperture size through which 50% by weight of the sample would pass.

Certain preferred granular detergent compositions in accordance with the present invention are the high-density types, now common in the marketplace; these typically have a bulk density of at least 600 g/liter, more preferably from 650 g/liter to 1200 g/liter.

Surfactant Agglomerate Particles

One of the preferred methods of delivering surfactant in consumer products is to make surfactant agglomerate particles, which may take the form of flakes, prills, marumes, noodles, ribbons, but preferably take the form of granules. A preferred way to process the particles is by agglomerating powders (e.g. aluminosilicate, carbonate) with high active surfactant pastes and to control the particle size of the resultant agglomerates within specified limits. Such a process involves mixing an effective amount of powder with a high active surfactant paste in one or more agglomerators such as a pan agglomerator, a Z-blade mixer or more preferably an in-line mixer such as those manufactured by Schugi (Holland) BV, 29 Chroomstraat 8211 AS, Lelystad, Netherlands, and Gebruder Lödige Maschinenbau GmbH, D-4790 Paderborn 1, Elsenerstrasse 7–9, Postfach 2050, Germany. Most preferably a high shear mixer is used, such as a Lödige CB (Trade Name).

A high active surfactant paste comprising from 50% by weight to 95% by weight, preferably 70% by weight to 85% by weight of surfactant is typically used. The paste may be pumped into the agglomerator at a temperature high enough to maintain a pumpable viscosity, but low enough to avoid degradation of the anionic surfactants used. An operating temperature of the paste of 50° C. to 80° C. is typical.

Laundry Washing Method

Machine laundry methods herein typically comprise treating soiled laundry with an aqueous wash solution in a washing machine having dissolved or dispensed therein an effective amount of a machine laundry detergent composition in accord with the invention. By an effective amount of the detergent composition it is here meant from 40 g to 300 g of product dissolved or dispersed in a wash solution of volume from 5 to 65 liters, as are typical product dosages and wash solution volumes commonly employed in conventional machine laundry methods.

As noted, surfactants are used herein in detergent compositions, preferably in combination with other detersive surfactants, at levels which are effective for achieving at least a directional improvement in cleaning performance. In the context of a fabric laundry composition, such "usage levels" can vary widely, depending not only on the type and severity of the soils and stains, but also on the wash water temperature, the volume of wash water and the type of washing machine.

In a preferred use aspect a dispensing device is employed in the washing method. The dispensing device is charged with the detergent product, and is used to introduce the product directly into the drum of the washing machine before the commencement of the wash cycle. Its volume capacity should be such as to be able to contain sufficient detergent product as would normally be used in the washing method.

Once the washing machine has been loaded with laundry the dispensing device containing the detergent product is placed inside the drum. At the commencement of the wash cycle of the washing machine water is introduced into the drum and the drum periodically rotates. The design of the dispensing device should be such that it permits containment of the dry detergent product but then allows release of this product during the wash cycle in response to its agitation as the drum rotates and also as a result of its contact with the wash water.

Alternatively, the dispensing device may be a flexible container, such as a bag or pouch. The bag may be of fibrous construction coated with a water impermeable protective material so as to retain the contents, such as is disclosed in European published Patent Application No. 0018678. Alternatively it may be formed of a water-insoluble synthetic polymeric material provided with an edge seal or closure designed to rupture in aqueous media as disclosed in European published Patent Application Nos. 0011500, 0011501, 0011502, and 0011968. A convenient form of water frangible closure comprises a water soluble adhesive disposed along and sealing one edge of a pouch formed of a water impermeable polymeric film such as polyethylene or polypropylene.

Machine Dishwashing Method

Any suitable methods for machine washing or cleaning soiled tableware, particularly soiled silverware are envisaged.

A preferred machine dishwashing method comprises treating soiled articles selected from crockery, glassware, hollowware, silverware and cutlery and mixtures thereof, with an aqueous liquid having dissolved or dispensed therein an effective amount of a machine dishwashing composition in accord with the invention. By an effective amount of the machine dishwashing composition it is meant from 8 g to 60 g of product dissolved or dispersed in a wash solution of volume from 3 to 10 liters, as are typical product dosages and wash solution volumes commonly employed in conventional machine dishwashing methods.

Packaging for the Compositions

Commercially marketed executions of the bleaching compositions can be packaged in any suitable container including those constructed from paper, cardboard, plastic materials and any suitable laminates. A preferred packaging execution is described in European Application No. 94921505.7.

Form of the Skin Care Compositions

The skin care compositions in accordance with the invention can take a variety of physical forms including powder, gel, tablet, bar, paste, cream and liquid forms. The form can be dependent upon the end use of the composition. The skin care composition can also be in a tissue, baby wipe, or other similar articles.

Form of the Personal Cleansing Compositions

The personal cleansing compositions in accordance with the invention can take a variety of physical forms including powder, gel, tablet, bar, paste, cream and liquid forms. The form can be dependent upon the end use of the composition.

Form of the Fabric Softener Compositions

Solid particulate compositions—The invention also comprises solid particulate composition comprising:

from about 50% to about 95%, preferably from about 60% to about 90%, of said biodegradable fabric softening active;

optionally, from 0% to about 30%, preferably from about 3% to about 15%, of dispersibility modifier; and from 0% to about 10% of a pH modifier.

Optional pH Modifier

Since the biodegradable ester fabric softener actives are somewhat labile to hydrolysis, it is preferable to include optional pH modifiers in the solid particulate fabric softener compositions to which water is to be added, to form stable dilute or concentrated liquid softener compositions. Said stable liquid fabric softener compositions should have a pH (neat) of from about 2 to about 5, preferably from about 2 to about 4.5, more preferably from about 2 to about 4.

The pH can be adjusted by incorporating a solid, water soluble Bronsted acid. Examples of suitable Bronsted acids include inorganic mineral acids, such as boric acid, sodium bisulfate, potassium bisulfate, sodium phosphate monobasic, potassium phosphate monobasic, and mixtures thereof; organic acids, such as citric acid, fumaric acid, maleic acid, malic acid, tannic acid, gluconic acid, glutamic acid, tartaric acid, glycolic acid, chloroacetic acid, phenoxyacetic acid, 1,2,3,4-butane tetracarboxylic acid, benzene sulfonic acid, benzene phosphonic acid, ortho-toluene sulfonic acid, para-toluene sulfonic acid, phenol sulfonic acid, naphthalene sulfonic acid, oxalic acid, 1,2,4,5-pyromellitic acid, 1,2,4-trimellitic acid, adipic acid, benzoic acid, phenylacetic acid, salicylic acid, succinic acid, and mixtures thereof; and mixtures of mineral inorganic acids and organic acids. Preferred pH modifiers are citric acid, gluconic acid, tartaric acid, 1,2,3,4-butane tetracarboxylic acid, malic acid, and mixtures thereof.

Optionally, materials that can form solid clathrates such as cyclodextrins and/or zeolites, etc., can be used as adjuvants in the solid particulate composition as host carriers of concentrated liquid acids and/or anhydrides, such as acetic acid, HCl, sulfuric acid, phosphoric acid, nitric acid, carbonic acid, etc. An example of such solid clathrates is carbon dioxide adsorbed in zeolite A, as disclosed in U.S. Pat. No. 3,888,998, Whyte and Samps, issued Jun. 10, 1975 and U.S. Pat. No. 4,007,134, Liepe and Japikse, issued Feb. 8, 1977, both of said patents being incorporated herein by reference. Examples of inclusion complexes of phosphoric acid, sulfuric acid, and nitric acid, and process for their preparation are disclosed in U.S. Pat. No. 4,365,061, issued Dec. 21, 1982 to Szejtli et al., said patent being incorporated herein by reference.

When used, the pH modifier is typically used at a level of from about 0.01% to about 10%, preferably from about 0.1% to about 5%, by weight of the composition.

Preparation of Solid Particulate Granular Fabric Softener

The granules can be formed by preparing a melt, solidifying it by cooling, and then grinding and sieving to the desired size. In a three-component mixture, e.g., nonionic surfactant, single-long-chain cationic, and DEQA, it is more preferred, when forming the granules, to pre-mix the nonionic surfactant and the more soluble single-long-chain alkyl cationic compound before mixing in a melt of the diester quaternary ammonium cationic compound.

It is highly preferred that the primary particles of the granules have a diameter of from about 50 to about 1,000, preferably from about 50 to about 400, more preferably from about 50 to about 200, microns. The granules can comprise smaller and larger particles, but preferably from about 85% to about 95%, more preferably from about 95% to about 100%, are within the indicated ranges. Smaller and larger particles do not provide optimum emulsions/dispersions when added to water. Other methods of preparing the primary particles can be used including spray cooling of the melt. The primary particles can be agglomerated to form a dust-free, non-tacky, free-flowing powder. The agglomeration can take place in a conventional agglomeration unit (i.e., Zig-Zag Blender, Lodige) by means of a water-soluble binder. Examples of water-soluble binders useful in the above agglomeration process include glycerol, polyethylene glycols, polymers such as PVA, polyacrylates, and natural polymers such as sugars.

The flowability of the granules can be improved by treating the surface of the granules with flow improvers such as clay, silica or zeolite particles, water-soluble inorganic salts, starch, etc.

Method of Use

Water can be added to the particulate, solid, granular compositions to form dilute or concentrated liquid softener compositions for later addition to the rinse cycle of the laundry process with a concentration of said biodegradable cationic softening compound of from about 0.5% to about 50%, preferably from about 1% to about 35%, more preferably from about 4% to about 32%. The particulate, rinse-added solid composition (1) can also be used directly in the rinse bath to provide adequate usage concentration (e.g., from about 10 to about 1,000 ppm, preferably from about 50 to about 500 ppm, of total softener active ingredient). The liquid compositions can be added to the rinse to provide the same usage concentrations.

The water temperature for preparation should be from about 20° C. to about 90° C., preferably from about 25° C. to about 80° C. Single-long-chain alkyl cationic surfactants as the viscosity/dispersibility modifier at a level of from 0% to about 15%, preferably from about 3% to about 15%, more preferably from about 5% to about 15%, by weight of the composition, are preferred for the solid composition. Nonionic surfactants at a level of from about 5% to about 20%, preferably from about 8% to about 15%, as well as mixtures of these agents can also serve effectively as the viscosity/dispersibility modifier.

The emulsified/dispersed particles, formed when the said granules are added to water to form aqueous concentrates, typically have an average particle size of less than about 10 microns, preferably less than about 2 microns, and more preferably from about 0.2 to about 2 microns, in order that effective deposition onto fabrics is achieved. The term "average particle size," in the context of this specification, means a number average particle size, i.e., more than 50% of the particles have a diameter less than the specified size.

Particle size for the emulsified/dispersed particles is determined using, e.g., a Malvern particle size analyzer.

Depending upon the particular selection of nonionic and cationic surfactant, it may be desirable in certain cases, when using the solids to prepare the liquid, to employ an efficient means for dispersing and emulsifying the particles (e.g., blender).

Solid particulate compositions used to make liquid compositions can, optionally, contain electrolytes, perfume, antifoam agents, flow aids (e.g., silica), dye, preservatives, and/or other optional ingredients described hereinbefore.

The benefits of adding water to the particulate solid composition to form aqueous compositions to be added later to the rinse bath include the ability to transport less weight thereby making shipping more economical, and the ability to form liquid compositions similar to those that are normally sold to consumers, e.g., those that are described herein, with lower energy input (i.e., less shear and/or lower temperature). Furthermore, the particulate granular solid fabric softener compositions, when sold directly to the consumers, have less packaging requirements and smaller, more disposable containers. The consumers will then add the compositions to available, more permanent, containers, and add water to pre-dilute the compositions, which are then ready for use in the rinse bath, just like the liquid compositions herein. The liquid form is easier to handle, since it simplifies measuring and dispensing.

Dryer Activated compositions—The present invention also relates to improved solid dryer-activated fabric softener compositions which are either incorporated into articles of manufacture, e.g., on a substrate, or, are in the form of particles similar to those disclosed above. (including, where appropriate, agglomerates, pellets, and tablets of said particles). Such compositions typically contain from about 10% to about 95% of fabric softening agent.

Substrate Articles—In preferred embodiments, the present invention encompasses articles of manufacture. Representative articles are those that are adapted for use to provide unique perfume benefits and to soften fabrics in an automatic laundry dryer, of the types disclosed in U.S. Pat. No. 3,989,631 Marsan, issued Nov. 2, 1976; U.S. Pat. No. 4,055,248, Marsan, issued Oct. 25, 1977; U.S. Pat. No. 4,073,996, Bedenk et al., issued Feb. 14, 1978; U.S. Pat. No. 4,022,938, Zaki et al., issued May 10, 1977; U.S. Pat. No. 4,764,289, Trinh, issued Aug. 16, 1988; U.S. Pat. No. 4,808,086, Evans et al., issued Feb. 28, 1989; U.S. Pat. No. 4,103,047, Zaki et al., issued Jul. 25, 1978; U.S. Pat. No. 3,736,668, Dillarstone, issued Jun. 5, 1973; U.S. Pat. No. 3,701,202, Compa et al., issued Oct. 31, 1972; U.S. Pat. No. 3,634,947, Furgal, issued Jan. 18, 1972; U.S. Pat. No. 3,633,538, Hoeflin, issued Jan. 11, 1972; and U.S. Pat. No. 3,435,537, Rumsey, issued Apr. 1, 1969; and U.S. Pat. No. 4,000,340, Murphy et al., issued Dec. 28, 1976, all of said patents being incorporated herein by reference.

Typical articles of manufacture of this type include articles comprising:

I. a fabric conditioning composition comprising from about 30% to about 95% of normally solid, dryer softenable fabric softening agent comprising said biodegradable fabric softening active; and II. a dispensing means which provides for release of an effective amount of said composition including an effective amount of ii, sufficient to provide odor control, to fabrics in an automatic laundry dryer at automatic laundry dryer operating temperatures, e.g., from about 35° C. to 115° C.

When the dispensing means is a flexible substrate, e.g., in sheet configuration, the fabric conditioning composition is releasably affixed on the substrate to provide a weight ratio of conditioning composition to dry substrate ranging from about 10:1 to about 0.5:1, preferably from about 5:1 to about 1:1.

The solid fabric softener compositions herein can include cationic and nonionic fabric softener actives used in combination with each other.

In the following Examples, the abbreviations for the various ingredients used for the compositions have the following meanings.

| | |
|---|---|
| MBFA | Mid-chain branched fatty acid |
| MBFS | Salt of Mid-chain branched fatty acid |
| MES | Alkyl methyl ester sulfonate |
| SAS | Secondary alkyl sulfate |
| NaPS | Sodium paraffin sulfonate |
| C45AS | Sodium $C_{14}$–$C_{15}$ linear alkyl sulfate |
| CxyAS | Sodium $C_{1x}$–$C_{1y}$ alkyl sulfate (or other salt if specified) |
| CxyEzS | Sodium $C_{1x}$–$C_{1y}$ alkyl sulfate condensed |
| LAS | Sodium linear alkyl benzene sulfonate |
| Citric acid | Anhydrous citric acid |
| LMFAA | C12-14 alkyl N-methyl glucamide |
| CxyFA | $C_{1x}$–$C_{1y}$ fatty acid |
| CxyEz | A $C_{1x}$–$C_{1y}$ branched primary alcohol condensed with an average of z moles of ethylene oxide |
| Carbonate | Anhydrous sodium carbonate with a particle size between 200 μm and 900 μm |
| Citrate | Tri-sodium citrate dihydrate of activity 86.4% with a particle size distribution between 425 μm and 850 μm |
| TFAA | C16–18 alkyl N-methyl glucamide |
| Fatty Acid (C12/14) | C12–C14 fatty acid |
| Fatty Acid (TPK) | Topped palm kernel fatty acid |
| Fatty Acid (RPS) | Rapeseed fatty acid |
| Borax | Na tetraborate decahydrate |
| PAA | Polyacrylic Acid (mw = 4500) |
| PEG | Polyethylene glycol (mw = 4600) with z moles of ethylene oxide (or other salt if specified) |
| CxyEz | A $C_{1x}$–$C_{1y}$ branched primary alcohol condensed with an average of z moles of ethylene oxide |
| AQA | $R_2.N^+(CH_3)_x((C_2H_4O)yH)z$ with $R_2 = C_8$–$C_{18}$ x + z = 3, x = 0 to 3, z = 0 to 3, y = 1 to 15. |
| STPP | Anhydrous sodium tripolyphosphate |
| Zeolite A | Hydrated Sodium Aluminosilicate of formula $Na_{12}(AlO_2SiO_2)_{12}.27H_2O$ having a primary particle size in the range from 0.1 to 10 micrometers |
| NaSKS-6 | Crystalline layered silicate of formula δ —$Na_2Si_2O_5$ |
| Carbonate | Anhydrous sodium carbonate with a particle size between 200 μm and 900 μm |
| Bicarbonate | Anhydrous sodium bicarbonate with a particle size distribution between 400 μm and 1200 μm |
| Silicate | Amorphous Sodium Silicate ($SiO_2$:$Na_2O$; 2.0 ratio) |
| Sulfate | Anhydrous sodium sulfate |
| PAE | ethoxylated tetraethylene pentamine |
| PIE | ethoxylated polyethylene imine |
| PAEC | methyl quaternized ethoxylated dihexylene triamine |
| MA/AA | Copolymer of 1:4 maleic/acrylic acid, average molecular weight about 70,000. |
| CMC | Sodium carboxymethyl cellulose |
| Protease | Proteolytic enzyme of activity 4KNPU/g sold by NOVO Industries A/S under the tradename Savinase |
| Cellulase | Cellulytic enzyme of activity 1000 CEVU/g sold by NOVO Industries A/S under the tradename Carezyme |
| Amylase | Amylolytic enzyme of activity 60 KNU/g sold by NOVO Industries A/S under the tradename Termamyl 60T |
| Lipase | Lipolytic enzyme of activity 100 kLU/g sold by NOVO Industries A/S under the tradename Lipolase |
| PB1 | Anhydrous sodium perborate bleach of nominal formula $NaBO_2.H_2O_2$ |
| Percarbonate | Sodium Percarbonate of nominal formula $2Na_2CO_3.3H_2O_2$ |
| NaDCC | Sodium dichloroisocyanurate |
| NOBS | Nonanoyloxybenzene sulfonate, sodium salt |
| TAED | Tetraacetylethylenediamine |

-continued

| | |
|---|---|
| DTPMP | Diethylene triamine penta (methylene phosphonate), marketed by Monsanto under Trade name Dequest 2060 |
| Photoactivated bleach | Sulfonated Zinc Phthalocyanine bleach encapsulated in dextrin soluble polymer |
| Brightener 1 | Disodium 4,4'-bis(2-sulphostyryl)biphenyl |
| Brightener 2 | Disodium 4,4'-bis(4-anilino-6-morpholino-1.3.5-triazin-2-yl)amino) stilbene-2:2'-disulfonate. |
| HEDP | 1,1-hydroxyethane diphosphonic acid |
| SRP 1 | Sulfobenzoyl end capped esters with oxyethylene oxy and terephthaloyl backbone |
| SRP 2 | sulfonated ethoxylated terephthalate polymer |
| SRP 3 | methyl capped ethoxylated terephthalate polymer |
| Silicone antifoam | Polydimethylsiloxane foam controller with siloxane-oxyalkylene copolymer as dispersing agent with a ratio of said foam controller to said dispersing agent of 10:1 to 100:1. |
| DTPA | Diethylene triamine pentaacetic acid |
| Endolase | Endoglunase enzyme of activity 3000 CEVU/g sold by NOVO Industries A/S |
| MEA | Monoethanolamine |
| PG | Propanediol |
| BPP | Butoxy - propoxy - propanol |
| EtOH | Ethanol |
| NaOH | Solution of sodium hydroxide |
| NaTS | Sodium toluene sulfonate |
| TFAA | C16–18 alkyl N-methyl glucamide |
| LMFAA | C12–14 alkyl N-methyl glucamide |
| APA | C8–C10 amido propyl dimethyl amine |
| Isofol 16 | Condea trademark for C16 (average) Guerbet alcohols |

In the following Examples all levels are quoted as % by weight of the composition. The following examples are illustrative of the present invention, but are not meant to limit or otherwise define its scope. All parts, percentages and ratios used herein are expressed as percent weight unless otherwise specified.

EXAMPLE I

The following laundry detergent compositions A to D are prepared in accord with the invention:

| | A | B | C | D |
|---|---|---|---|---|
| MBFS[1] | 2 | 4.0 | 4.0 | 8.0 |
| C45AS | 6 | 4.0 | 2.8 | — |
| LAS | — | — | 1.2 | — |
| C25E3 | 3.4 | 3.4 | 3.4 | 3.4 |
| AQA | 0.4 | 0.5 | 0.6 | 0.8 |
| Zeolite A | 18.1 | 18.1 | 18.1 | 18.1 |
| Carbonate | 13.0 | 13.0 | 13.0 | 27.0 |
| Silicate | 1.4 | 1.4 | 1.4 | 3.0 |
| Sulfate | 26.1 | 26.1 | 26.1 | 26.1 |
| PB1 | 9.0 | 9.0 | 9.0 | 9.0 |
| TAED | 1.5 | 1.5 | 1.5 | 1.5 |
| DTPMP | 0.25 | 0.25 | 0.25 | 0.25 |
| HEDP | 0.3 | 0.3 | 0.3 | 0.3 |
| Protease | 0.26 | 0.26 | 0.26 | 0.26 |
| Amylase | 0.1 | 0.1 | 0.1 | 0.1 |
| MA/AA | 0.3 | 0.3 | 0.3 | 0.3 |
| CMC | 0.2 | 0.2 | 0.2 | 0.2 |
| Photoactivated bleach | 15 ppm | 15 ppm | 15 ppm | 15 ppm |
| Brightener 1 | 0.09 | 0.09 | 0.09 | 0.09 |
| Perfume | 0.3 | 0.3 | 0.3 | 0.3 |
| Silicone antifoam | 0.5 | 0.5 | 0.5 | 0.5 |
| Misc/minors to 100% | | | | |
| Density in g/liter | 850 | 850 | 850 | 850 |

[1]Mid-branched fatty soaps are selected according to the invention as exemplified by Example 78

EXAMPLE II

The following laundry detergent compositions E to I are prepared in accord with the invention:

| | E | F | G | H | I |
|---|---|---|---|---|---|
| MBFS[1] | 22 | 16.5 | 11 | 1–5.5 | 10–25 |
| Any Combination of: | 0 | 1–5.5 | 11 | 16.5 | 0–5 |
| C45 AS | | | | | |
| C45E1S | | | | | |
| LAS | | | | | |
| C16 SAS | | | | | |
| C14–17 NaPS | | | | | |
| C14–18 MES | | | | | |
| AQA | 0–2 | 0–2 | 0–2 | 0–2 | 0–4 |
| C23E6.5 or C45E7 | 1.5 | 1.5 | 1.5 | 1.5 | 0–4 |
| Zeolite A | 27.8 | 27.8 | 27.8 | 27.8 | 20–30 |
| PAA | 2.3 | 2.3 | 2.3 | 2.3 | 0–5 |
| Carbonate | 27.3 | 27.3 | 27.3 | 27.3 | 20–30 |
| Silicate | 0.6 | 0.6 | 0.6 | 0.6 | 0–2 |
| PB1 | 1.0 | 1.0 | 1.0 | 1.0 | 0–3 |
| Protease | 0–0.5 | 0–0.5 | 0–0.5 | 0–0.5 | 0–0.5 |
| Cellulase | 0–0.3 | 0–0.3 | 0–0.3 | 0–0.3 | 0–0.5 |
| Amylase | 0–0.5 | 0–0.5 | 0–0.5 | 0–0.5 | 0–1 |
| SRP 1 | 0.4 | 0.4 | 0.4 | 0.4 | 0–1 |
| Brightener 1 or 2 | 0.2 | 0.2 | 0.2 | 0.2 | 0–0.3 |
| PEG | 1.6 | 1.6 | 1.6 | 1.6 | 0–2 |
| Sulfate | 5.5 | 5.5 | 5.5 | 5.5 | 0–6 |
| Silicone Antifoam | 0.42 | 0.42 | 0.42 | 0.42 | 0–0.5 |
| Moisture & Minors | | | Balance | | |
| Density (g/L) | 663 | 663 | 663 | 663 | 600–700 |

[1]Mid-branched fatty soaps are selected according to the invention as exemplified by example 78

EXAMPLE III

The following laundry detergent compositions J to N are prepared in accord with the invention:

| | J | K | L | M | N |
|---|---|---|---|---|---|
| MBFS[1] | 16.5 | 12.5 | 8.5 | 4 | 1–25 |
| Any Combination of: | 0–6 | 10 | 14 | 18.5 | 0–20 |
| C45 AS | | | | | |
| C45E1S | | | | | |
| LAS | | | | | |
| C16 SAS | | | | | |
| C14–17 NaPS | | | | | |
| C14–18 MES | | | | | |
| AQA | 0–2 | 0–2 | 0–2 | 0–2 | 0–4 |
| TFAA | 1.6 | 1.6 | 1.6 | 1.6 | 0–4 |
| C24E3, C23E6.5 | 5 | 5 | 5 | 5 | 0–6 |
| Zeolite A | 15 | 15 | 15 | 15 | 10–30 |
| NaSKS-6 | 11 | 11 | 11 | 11 | 5–15 |
| Citrate | 3 | 3 | 3 | 3 | 0–8 |
| MA/AA | 4.8 | 4.8 | 4.8 | 4.8 | 0–8 |
| HEDP | 0.5 | 0.5 | 0.5 | 0.5 | 0–1 |
| Carbonate | 8.5 | 8.5 | 8.5 | 8.5 | 0–15 |
| Percarbonate or PB1 | 20.7 | 20.7 | 20.7 | 20.7 | 0–25 |
| TAED | 4.8 | 4.8 | 4.8 | 4.8 | 0–8 |
| Protease | 0.9 | 0.9 | 0.9 | 0.9 | 0–1 |
| Lipase | 0.15 | 0.15 | 0.15 | 0.15 | 0–0.3 |
| Cellulase | 0.26 | 0.26 | 0.26 | 0.26 | 0–0.5 |
| Amylase | 0.36 | 0.36 | 0.36 | 0.36 | 0–0.5 |
| SRP 1 | 0.2 | 0.2 | 0.2 | 0.2 | 0–0.5 |
| Brightener 1 or 2 | 0.2 | 0.2 | 0.2 | 0.2 | 0–0.4 |
| Sulfate | 2.3 | 2.3 | 2.3 | 2.3 | 0–25 |
| Silicone Antifoam | | 0.4 | 0.4 | 0.4 | 0–1 |
| Moisture & Minors | | | Balance | | |
| Density (g/L) | 850 | 850 | | 850 | 850 |

[1]Mid-branched fatty soaps are selected according to the invention as exemplified by example 78

EXAMPLE IV

The following laundry detergent compositions O to T are prepared in accord with the invention:

|  | O | P | Q | R | S | T |
|---|---|---|---|---|---|---|
| MBFS[1] | 32 | 24 | 16 | 8 | 4 | 1–35 |
| Any Combination of: | 0 | 8 | 16 | 24 | 28 | 0–35 |
| C45 AS |  |  |  |  |  |  |
| C45E1S |  |  |  |  |  |  |
| LAS |  |  |  |  |  |  |
| C16 SAS |  |  |  |  |  |  |
| C14–17 NaPS |  |  |  |  |  |  |
| C14–18 MES |  |  |  |  |  |  |
| C23E6.5 or C45E7 | 3.6 | 3.6 | 3.6 | 3.6 | 3.6 | 0–6 |
| AQA | 0–1 | 0–1 | 0–1 | 0–1 | 0–1 | 0–4 |
| Zeolite A | 9.0 | 9.0 | 9.0 | 9.0 | 9.0 | 0–20 |
| PAA or MA/AA | 7.0 | 7.0 | 7.0 | 7.0 | 7.0 | 0–10 |
| Carbonate | 18.4 | 18.4 | 18.4 | 18.4 | 18.4 | 5–25 |
| Silicate | 11.3 | 11.3 | 11.3 | 11.3 | 11.3 | 5–25 |
| PB1 | 3.9 | 3.9 | 3.9 | 3.9 | 3.9 | 1–6 |
| NOBS | 4.1 | 4.1 | 4.1 | 4.1 | 4.1 | 0–6 |
| Protease | 0.9 | 0.9 | 0.9 | 0.9 | 0.9 | 0–1.3 |
| Amylase | 0–0.5 | 0–0.5 | 0–0.5 | 0–0.5 | 0–0.5 | 0–0.5 |
| Cellulase | 0–0.3 | 0–0.3 | 0–0.3 | 0–0.3 | 0–0.3 | 0–0.3 |
| SRP1 | 0.5 | 0.5 | 0.5 | 0.5 | 0.5 | 0–1 |
| Brightener 1 or 2 | 0.3 | 0.3 | 0.3 | 0.3 | 0.3 | 0–0.5 |
| PEG | 0.2 | 0.2 | 0.2 | 0.2 | 0.2 | 0–0.5 |
| Sulfate | 5.1 | 5.1 | 5.1 | 5.1 | 5.1 | 0–10 |
| Silicone Antifoam | 0.2 | 0.2 | 0.2 | 0.2 | 0.2 | 0–0.5 |
| Moisture & Minors |  |  | Balance |  |  |  |
| Density (g/L) | 810 | 810 | 810 | 810 | 810 | 810 |

[1]Mid-branched fatty soaps are selected according to the invention as exemplified by example 78

EXAMPLE V

The following high density detergent formulations U to X, according to the present invention, are prepared:

|  | U | V | W | X |
|---|---|---|---|---|
| Agglomerate |  |  |  |  |
| C45AS | 11.0 | 7.0 | 4 | 14.0 |
| MBFS[1] | 3.0 | 10.0 | 17.0 | 3.0 |
| Zeolite A | 15.0 | 12.0 | 10.0 | 10.0 |
| Carbonate | 4.0 | 4.0 | 4.0 | 8.0 |
| PAA or MA/AA | 4.0 | 4.0 | 4.0 | 2.0 |
| CMC | 0.5 | 0.5 | 0.5 | 0.5 |
| DTPMP | 0.4 | 0.4 | 0.4 | 0.4 |
| Spray On |  |  |  |  |
| C23E6.5 | 5.0 | 5.0 | 5.0 | 5.0 |
| Perfume | 0.5 | 0.5 | 0.5 | 0.5 |
| Dry Adds |  |  |  |  |
| C45AS | 6.0 | 6.0 | 3.0 | 3.0 |
| HEDP | 0.5 | 0.5 | 0.5 | 0.3 |
| SKS-6 | 13.0 | 13.0 | 13.0 | 6.0 |
| Citrate | 3.0 | 3.0 | 3.0 | 1.0 |
| TAED | 5.0 | 5.0 | 5.0 | 7.0 |
| Percarbonate | 20.0 | 20.0 | 20.0 | 20.0 |
| SRP 1 | 0.3 | 0.3 | 0.3 | 0.3 |
| Protease | 1.4 | 1.4 | 1.4 | 1.4 |
| Lipase | 0.4 | 0.4 | 0.4 | 0.4 |
| Cellulase | 0.6 | 0.6 | 0.6 | 0.6 |
| Amylase | 0.6 | 0.6 | 0.6 | 0.6 |
| Silicone antifoam | 5.0 | 5.0 | 5.0 | 5.0 |
| Brightener 1 | 0.2 | 0.2 | 0.2 | 0.2 |
| Brightener 2 | 0.2 | 0.2 | 0.2 | — |
| Balance (Water/Miscellaneous) | 100 | 100 | 100 | 100 |
| Density (g/liter) | 850 | 850 | 850 | 850 |

[1]Mid-branched fatty soaps are selected according to the invention as exemplified by example 78

EXAMPLE VI

The following laundry detergent compositions Y to BB suitable for hand-washing soiled fabrics are prepared in accord with the invention:

|  | Y | Z | AA | BB |
|---|---|---|---|---|
| MBFS[1] | 5 | 10 | 18 | 22 |
| LAS | 20 | 10 | 11 | - |
| STPP | 15 | 30 | 11 | 28 |
| Carbonate | 15 | 8 | 20 | 15 |
| Silicates | 15 | 10 | 15 | 10 |
| Protease | 0 | 0 | 0.3 | 0.3 |
| Perborate | 0 | 0 | 0 | 10 |
| Sodium Chloride | 25 | 15 | 20 | 10 |
| Brightener, perfume | 0-0.3 | 0.2 | 0.2 | 0.2 |
| Moisture & Minors[2] |  | Balance |  |  |

[1]Mid-branched fatty soaps are selected according to the invention as exemplified by example 78
[2]Can be selected from convenient materials such as $CaCO_3$, talc, clay, sulfates, silicates, and the like.

EXAMPLE VII

The following laundry detergent compositions CC to FF suitable for hand-washing soiled fabrics are prepared in accord with the invention:

|  | CC | DD | EE | FF |
|---|---|---|---|---|
| MBFS[1] | 22 | 16 | 11 | 1–6 |
| Any Combination of: | 0 | 0–5 | 5–15 | 10–20 |
| C45 AS |  |  |  |  |
| C45E1S |  |  |  |  |
| C45E3S |  |  |  |  |
| LAS |  |  |  |  |
| AQA | 0–5 | 0–1 | 0–5 | 0–3 |
| Any Combination of: | 0–2 | 0–4 | 0–2 | 0–2 |
| C23E6.5 |  |  |  |  |
| C45E7 |  |  |  |  |
| STPP | 5–45 | 5–45 | 5–45 | 5–45 |
| PAA | 0–2 | 0–2 | 0–2 | 0–2 |
| CMC | 0–0.5 | 0–0.5 | 0–0.5 | 0–0.5 |
| Protease | 0–0.5 | 0–0.5 | 0–0.5 | 0–0.5 |
| Cellulase | 0–0.3 | 0–0.3 | 0–0.3 | 0–0.3 |
| Amylase | 0–0.5 | 0–0.5 | 0–0.5 | 0–0.5 |
| SRP | 0–0.5 | 0.4 | 0–0.5 | 0–0.5 |
| Brightener, perfume | 0–0.3 | 0–0.2 | 0–0.3 | 0–0.2 |
| Photobleach | 0–0.1 | 0–0.1 | 0–0.1 | 0–0.1 |
| Carbonate | 15 | 10 | 20 | 15 |
| Silicate | 7 | 15 | 10 | 8 |
| Sulfate | 5 | 5 | 5 | 5 |
| Moisture & Minors[2] |  | Balance |  |  |

[1]Mid-branched fatty soaps are selected according to the invention as exemplified by example 78
[2]Can be selected from convenient materials such as $CaCO_3$, NaCl, talc, clay, sulfates, silicates, and the like.

EXAMPLE VIII

Light-duty liquid dishwashing detergent compositions comprising the mid-chain branched soaps of the present claims are prepared:

| Ingredient | Wt. % GG | Wt. % HH | Wt. % II | Wt. % JJ |
|---|---|---|---|---|
| C23E0.6S | 25 | 20 | 15 | 0 |
| C23E9 | 1 | 1 | 1 | 1 |
| MBFS[1] | 5 | 10 | 15 | 30 |
| LMFAA | 4 | 4 | 4 | 4 |
| Coconut amine oxide | 4 | 4 | 4 | 4 |
| EO/PO Block Co-polymer-Tetronic® 704 | 0.5 | 0.5 | 0.5 | 0.5 |
| EtOH | 6 | 6 | 6 | 6 |
| Calcium xylene sulfonate | 5 | 5 | 5 | 5 |
| Magnesium++ (added as chloride) | 3.0 | 3.0 | 3.0 | 3.0 |
| Water, thickeners and minors | to 100% | to 100% | to 100% | to 100% |
| pH @ 10% (as made) | 7.5 | 7.5 | 7.5 | 7.5 |

[1]Mid-branched fatty soaps are selected according to the invention as exemplified by example 78

EXAMPLE IX

This example illustrates the preparation and performance advantages of the mid-chain branched fatty acid containing non-aqueous liquid detergent compositions of the instant invention. Such examples, however, are not necessarily meant to limit or otherwise define the scope of the invention herein. All parts, percentages and ratios used herein are expressed as percent weight unless otherwise specified.

Preparation of LAS Powder for Use as a Structurant

Sodium $C_{12}$ linear alkyl benzene sulfonate (NaLAS) is processed into a powder containing two phases. One of these phases is soluble in the non-aqueous liquid detergent compositions herein and the other phase is insoluble. It is the insoluble fraction which serves to add structure and particle suspending capability to the non-aqueous phase of the compositions herein.

NaLAS powder is produced by taking a slurry of NaLAS in water (approximately 40–50% active) combined with dissolved sodium sulfate (3–15%) and hydrotrope, sodium sulfosuccinate (1–3%). The hydrotrope and sulfate are used to improve the characteristics of the dry powder. A drum dryer is used to dry the slurry into a flake. When the NaLAS is dried with the sodium sulfate, two distinct phases are created within the flake. The insoluble phase creates a network structure of aggregate small particles (0.4–2 um) which allows the finished non-aqueous detergent product to stably suspend solids.

The NaLAS powder prepared according to this example has the following makeup shown in Table I.

TABLE 1

| Component | Wt. % |
|---|---|
| NaLAS | 85% |
| Sulfate | 11% |
| Sulfosuccinate | 2% |
| Water | 2.5% |
| Unreacted, etc. | balance to 100% |
| % insoluble LAS | 17% |
| # of phase (via X-ray diffraction) | 2 |

TABLE II

Non-aqueous based heavy duty liquid laundry detergent compositions (KK to OO) which comprise the mid-chain branched acids of the present invention are presented below.

Non-Aqueous Liquid Detergent Composition with Bleach

| Component | Wt % KK | Wt % LL | Wt % MM | Wt % NN | Wt % OO |
|---|---|---|---|---|---|
| LAS, From Above | 16 | 13 | 8 | 8 | 2 |
| MBFA[1] | 22 | 25 | 28 | 30 | 34 |
| BPP | 19 | 19 | 19 | 19 | 19 |
| Citrate | 3 | 3 | 3 | 3 | 3 |
| Bleach activator | 5.9 | 5.9 | 5.9 | 5.9 | 5.9 |
| Carbonate | 9 | 9 | 9 | 9 | 9 |
| MA/AA | 3 | 3 | 3 | 3 | 3 |
| Colored speckles | 0.4 | 0.4 | 0.4 | 0.4 | 0.4 |
| EDDS | 1 | 1 | 1 | 1 | 1 |
| Cellulase Prills | 0.1 | 0.1 | 0.1 | 0.1 | 0.1 |
| Amylase Prills | 0.4 | 0.4 | 0.4 | 0.4 | 0.4 |
| Ethoxylated diamine quat | 1.3 | 1.3 | 1.3 | 1.3 | 1.3 |
| Perborate | 15 | 15 | 15 | 15 | 15 |
| Optionals including: brightener, colorant, perfume, thickener, suds suppressor, colored speckles etc. | balance | balance | balance | balance | balance |
|  | 100% | 100% | 100% | 100% | 100% |

[1]Mid-branched fatty acids are selected according to the invention as exemplified by any of examples 1–78 or mixtures thereof.

The resulting Table II composition is a stable, anhydrous heavy-duty liquid laundry detergent which provides excellent stain and soil removal performance when used in normal fabric laundering operations.

EXAMPLE X

Aqueous based heavy duty liquid laundry detergent compositions PP to TT which comprise the mid-chain branched soaps of the present invention are presented below.

| Ingredient | PP | QQ | RR | SS | TT |
|---|---|---|---|---|---|
| MBFS | 10 | 8 | 6 | 4 | 2 |
| Na C25AE1.8S | 10 | 12 | 14 | 16 | 18 |
| C23E9 | 2 | 2 | 2 | 2 | 2 |
| LMFAA | 5 | 5 | 5 | 5 | 0 |
| Citric acid builder | 3 | 3 | 3 | 3 | 3 |
| Fatty acid builder | 0 | 1 | 2 | 4 | 5 |
| PAE | 1 | 1 | 1.2 | 1.2 | 0.5 |
| PG | 8 | 8 | 8 | 8 | 4.5 |
| EtOH | 4 | 4 | 4 | 4 | 2 |
| Boric acid | 3.5 | 3.5 | 3.5 | 3.5 | 2 |
| Sodium Cumene Sulfonate | 3 | 3 | 3 | 3 | 0 |
|  | 8.0 | 8.0 | 8.0 | 7.0 |  |
| Enzymes, dyes, water | balance | balance | balance | balance | balance |
|  | 100% | 100% | 100% | 100% | 100% |

1) Mid-branched fatty soaps are selected according to the invention as exemplified by example 78

EXAMPLE XI

The following aqueous liquid laundry detergent compositions UU to YY are prepared in accord with the invention:

| | UU | VV | WW | XX | YY |
|---|---|---|---|---|---|
| MBFS | 1–7 | 7–12 | 12–17 | 17–22 | 1–35 |
| Any combination of: | 15–21 | 10–15 | 5–10 | 0–5 | 0–25 |
| C25 AExS*Na (x = 1.8–2.5) | | | | | |
| C25 AS (linear to high 2-alkyl) | | | | | |
| C14–17 NaPS | | | | | |
| C12–16 SAS | | | | | |
| C18 1,4 disulfate | | | | | |
| LAS | | | | | |
| C12–16 MES | | | | | |
| LMFAA | 0–3.5 | 0–3.5 | 0–3.5 | 0–3.5 | 0–8 |
| C23E9 or C23E6.5 | 0–2 | 0–2 | 0–2 | 0–2 | 0–8 |
| APA | 0.5 | 0.5 | 0.5 | 0.5 | 0.5–2 |
| Citric Acid | 5 | 5 | 3 | 3 | 0–8 |
| Fatty Acid (TPK or C12/14) | 4 | 3 | 2 | 1 | 0–14 |
| EtOH | 4 | 4 | 4 | 4 | 0–8 |
| PG | 6 | 6 | 6 | 6 | 0–10 |
| MEA | 1 | 1 | 1 | 1 | 0–3 |
| NaOH | 3 | 3 | 3 | 3 | 0–7 |
| Na TS | 2.3 | 2.3 | 2.3 | 2.3 | 0–4 |
| Na formate | 0.1 | 0.1 | 0.1 | 0.1 | 0–1 |
| Borax | 2.5 | 2.5 | 2.5 | 2.5 | 0–5 |
| Protease | 0.9 | 0.9 | 0.9 | 0.9 | 0–1.3 |
| Lipase | 0.06 | 0.06 | 0.06 | 0.06 | 0–0.3 |
| Amylase | 0.15 | 0.15 | 0.15 | 0.15 | 0–0.4 |
| Cellulase | 0.05 | 0.05 | 0.05 | 0.05 | 0–0.2 |
| PAE | 0–0.6 | 0–0.6 | 0–0.6 | 0–0.6 | 0–2.5 |
| PIE | 1.2 | 1.2 | 1.2 | 1.2 | 0–2.5 |
| PAEC | 0–0.4 | 0–0.4 | 0–0.4 | 0–0.4 | 0–2 |
| SRP 2 | 0.2 | 0.2 | 0.2 | 0.2 | 0–0.5 |
| Brightener 1 or 2 | 0.15 | 0.15 | 0.15 | 0.15 | 0–0.5 |
| Silicone antifoam | 0.12 | 0.12 | 0.12 | 0.12 | 0–0.3 |
| Fumed Silica | 0.0015 | 0.0015 | 0.0015 | 0.0015 | 0–0.003 |
| Perfume | 0.3 | 0.3 | 0.3 | 0.3 | 0–0.6 |
| Dye | 0.0013 | 0.0013 | 0.0013 | 0.0013 | 0–0.003 |
| Moisture/minors | Balance | Balance | Balance | Balance | Balance |
| Product pH (10% in DI water) | 7.7 | 7.7 | 7.7 | 7.7 | 6–9.5 |

1) Mid-branched fatty soaps are selected according to the invention as exemplified by example 78

EXAMPLE XII

Clear Fabric Softener Compositions with Various Fabric Softener Levels and Solvent Systems

| Component (Wt %) | A1 | B1 | C1 | D1 | E1 | F1 | G1 | H1 | I1 |
|---|---|---|---|---|---|---|---|---|---|
| TEA Diester Quat[1] | 30 | 35 | 30 | 30 | 30 | 35 | 30 | 35 | 30 |
| Ethanol (from active) | 2.47 | 2.88 | 2.47 | 2.47 | 2.47 | 2.88 | 2.47 | 2.88 | 2.47 |
| Hexylene Glycol (from active) | 2.7 | 3.1 | 2.7 | 2.7 | 2.7 | 3.1 | 2.7 | 3.1 | 2.7 |
| TMPD | 4 | 5 | — | 5 | 5 | — | — | — | 5.5 |
| Hexylene Glycol | — | — | 6 | — | — | 10 | — | 2 | — |
| 2-Ethyl-1,3-Hexanediol | — | — | — | — | — | — | 6 | — | — |
| Neodol 91-8 | 5 | 6 | 4 | 6 | 6 | 5 | 5 | 5 | 6 |
| Pluronic L-35O | 1 | 1 | 1 | 1 | 1 | 1 | 1 | 1 | 1 |
| HC1 | 0–0.25 | 0–0.25 | 0–0.25 | 0–0.25 | 0–0.25 | 0–0.25 | 0–0.25 | 0–0.25 | 0–0.25 |
| MgC12 | 1.75 | 1.75 | 2.00 | 1.75 | 1.75 | 2.20 | 1.50 | 1.75 | 1.75 |
| Perfume | 2.2 | 2.5 | 2.5 | 2 | 2.5 | 3 | 2 | 2 | 2 |
| DTPA | 0.01 | 0.01 | 0.01 | 0.01 | 0.01 | 0.01 | 0.01 | 0.01 | 0.01 |

-continued

| Component (Wt %) | A1 | B1 | C1 | D1 | E1 | F1 | G1 | H1 | I1 |
|---|---|---|---|---|---|---|---|---|---|
| Blue Dye | 0.0003 | 0.0003 | 0.0003 | 0.0003 | 0.0003 | 0.0003 | 0.0003 | 0.0003 | 0.0003 |
| Deionized Water & Minors | Bal. | Bal. | Bal. | Bal. | Bal. | Bal. | Bal. | Bal. | Bal. |

[1]Di(acyloxyethyl)(2-hydroxyethyl)methyl ammonium methyl sulfate where the acyl group is derived from a mixture of partially hydrogenated canola fatty acid and the branched acid of example 1.

EXAMPLE XIII

Clear Fabric Softener Compositions with Low Solvent Levels and Various Principal Solvents

| Component Wt % | J1 | K1 | L1 | M1 | N1 | O1 |
|---|---|---|---|---|---|---|
| TEA Diester Quat[1]. | 30 | 30 | 45 | 40 | 45 | 30 |
| Ethanol from softener active | 2.47 | 2.47 | 3.71 | 3.29 | 3.71 | 2.47 |
| Hexylene Glycol from softener active | 2.65 | 2.65 | 3.97 | 3.53 | 3.97 | 2.65 |
| Principal Solvent: | | | | | | |
| TMPD | 5 | 5 | — | — | — | 4 |
| 1,2-Hexanediol | — | — | 1 | — | — | — |
| 1,2-Pentanediol | — | — | — | 1 | — | — |
| 1,2-Butanediol | — | — | — | — | 3 | — |
| Phase Stabilizer: | | | | | | |
| Neodol 91-8 | 5 | 5 | — | — | — | 5 |
| Rewopal C6 | — | — | 2.9 | 2.9 | 2.9 | — |
| Pluronic L35 | 1 | 1 | 0.5 | 1 | — | 1 |
| MgCl2 | 1.75 | — | — | — | — | 1.75 |
| CaCl2 | — | 1.75 | — | — | — | — |
| Perfume | 1.8 | 2.0 | 1.5 | 1.5 | 1.5 | 2.2 |
| De-ionized Water & minors | Bal. | Bal. | Bal. | Bal. | Bal. | Bal. |

[1]Di(acyloxyethyl)(2-hydroxyethyl)methyl ammonium methyl sulfate where the acyl group is derived from a mixture of partially hydrogenated canola fatty acid and the branched acid of example 2.

Clear Fabric Softening Compositions with 45% Fabric Softening Active and Various Electrolytes and Solvent Systems

| Component Wt % | P1 | Q1 | R1 | S1 | T1 | U1 | V1 | W1 |
|---|---|---|---|---|---|---|---|---|
| TEA Diester Quat.[1] | 45 | 45 | 45 | 45 | 45 | 45 | 45 | 45 |
| Ethanol (from active) | 7 | — | 3.71 | 3.71 | 3.71 | 3.71 | 3.71 | 3.71 |
| Hexylene Glycol (from active) | — | 3.97 | 3.97 | 3.97 | 3.97 | 3.97 | 3.97 | 3.97 |
| Hexylene Glycol | — | 2.03 | — | — | — | — | — | — |
| Pinacol | — | — | 3 | — | — | — | — | — |
| Neopentyl Glycol | — | — | — | 3 | — | — | — | — |
| Isopropanol | — | — | — | — | — | — | 3 | — |
| Butyl Carbitol | — | — | — | — | — | — | — | 3.1 |
| 1,5-Hexanediol | — | — | — | — | — | 3 | — | — |
| Rewopal C6 | 3 | 3 | 3 | 3 | 3 | 3 | 3 | 3.6 |
| Electrolyte | KCl | CaCl2 | KCl | CaCl2 | K Citrate | K Citrate | CaCl2 | CaCl2 |
| % of Electrolyte | 1 | 1 | 1 | 1 | 2 | 2 | 1 | 1.2 |
| Perfume | 1.5 | 1.5 | 1.5 | 1.5 | 1.5 | 1.5 | 1.5 | 2 |
| De-ionized Water | Bal. | Bal. | Bal. | Bal. | Bal. | Bal. | Bal. | Bal. |

[1]Di(acyloxyethyl)(2-hydroxyethyl)methyl ammonium methyl sulfate where the acyl group is derived from a mixture of partially hydrogenated canola fatty acid, the branched acid of example 1 and the branched acid of example 3.

Clear Fabric Softening Compositions with
Hexylene Glycol as Principal Solvent

| Component Wt % | X1 | Y1 | Z1 | A2 | B2 | C2 | D2 | E2 | F2 | G2 | H2 |
|---|---|---|---|---|---|---|---|---|---|---|---|
| TEA Diester Quat.[1] | 45 | 45 | 45 | 45 | 45 | 30 | 28 | 32 | 32 | 36 | 36 |
| Ethanol (from active) | 3.7 | 3.7 | 3.7 | 3.7 | 3.7 | 2.5 | 2.3 | 2.6 | 2.6 | 3.3 | 3.3 |
| Hexylene Glycol (from active) | 4 | 4 | 4 | 4 | 4 | 2.7 | 2.5 | 2.8 | 2.8 | — | — |
| Hexylene Glycol | 3 | 6 | 9 | 7.3 | 3 | 9 | 3 | 3.3 | 6.1 | 6.5 | 6.5 |
| Rewopal C6 | 3.5 | 2.5 | 1.5 | 3.1 | 2.9 | 3 | — | — | — | 1.8 | 1.8 |
| Neodol 91-8 | — | — | — | — | — | — | 3.1 | 3.0 | 4.9 | — | — |
| CaCl2 | 1.1 | 1.1 | 0.8 | 2 | 1 | 0.95 | 2.1 | 2 | 1 | — | 1.2 |
| Sodium Cumene Sulfonate | — | — | — | — | — | — | — | — | — | 1 | — |
| Perfume | 2.0 | 2.0 | 2.0 | 2.0 | 1.5 | 1.5 | 1.0 | 1.1 | 3.2 | 1.2 | 1.2 |
| De-ionized Water | Bal. | Bal. | Bal. | Bal. | Bal. | Bal. | Bal. | Bal. | Bal. | Bal. | Bal. |

[1]Di(acyloxyethyl)(2-hydroxyethyl)methyl ammonium methyl sulfate where the acyl group is derived from a mixture of partially hydrogenated canola fatty acid and a mixture of the branched acids of examples 6, 9 and 11–13.

EXAMPLE XIV

Dispersion Examples

The compositions of Example XIV are made at ambient temperature by the following process:

1. Prepare the water seat containing HCl.
2. Separately, mix perfume and Tenox antioxidant to the diester softener active.
3. Add the diester active blend into the water seat with mixing.
4. Add about 10–20% of the CaCl2 solution at approximately halfway through the diester addition.
5. Add the remainder of the CaCl2 solution after the diester addition is complete with mixing.

| Ingredients Wt. % | I2 | J2 | K2 | L2 | M2 | N2 |
|---|---|---|---|---|---|---|
| DEQA2 (85% active in ethanol) | 18 | — | 15 | — | — | — |
| DEQA8 (85% active in ethanol) | — | 18 | — | 12 | — | — |
| DEQA10 (85% active in ethanol) | 9.2 | 9.2 | 15 | 12 | — | — |
| DEQA24 (85% active in ethanol) | — | — | — | — | — | 20.8 |
| DEQA25 (85% active in ethanol) | — | — | — | — | 28 | — |
| Perfume | 1.35 | 1.35 | 1.35 | 1.35 | 1.35 | 1.35 |
| Tenox 6 | 0.04 | 0.04 | 0.04 | 0.04 | 0.04 | 0.04 |
| CaCl2 (25% solution) | 2 | 2 | 2 | 2 | 2 | 2 |
| HCl 1N | 0.30 | 0.30 | 0.30 | 0.30 | 0.30 | 0.30 |
| Distilled Water | Bal. | Bal. | Bal. | Bal. | Bal. | Bal. |

DEQA2 is Di(acyloxyethyl)(2-hydroxyethyl)methyl ammonium methyl sulfate where the acyl group is derived from a partially hydrogenated canola fatty acid 85% active.

DEQA8 is Di(acyloxyethyl)(2-hydroxyethyl)methyl ammonium methyl sulfate where the acyl group is derived from a mixture of partially hydrogenated canola fatty acid and a mixture of the branched acids of examples 16–23, 85% active.

DEQA10 is Di(acyloxyethyl)(2-hydroxyethyl)methyl ammonium methyl sulfate where the acyl group is derived from a mixture of partially hydrogenated canola fatty acid and a mixture of the branched acids of examples 24 to 30, 85% active.

DEQA24 is Di(acyloxyethyl)(2-hydroxyethyl)methyl ammonium methyl sulfate where the acyl group is derived from a mixture of partially hydrogenated canola fatty acid and the branched acid of example 13, 85% active.

DEQA25 is Di(acyloxyethyl)(2-hydroxyethyl)methyl ammonium methyl sulfate where the acyl group is derived from a mixture of partially hydrogenated canola fatty acid and a mixture of the branched acids of examples 30–35, 38–42, 62–65 and 73, 85% active.

The above Examples show dispersion compositions with good stability and performance.

What is claimed is:

1. A fabric softening active selected from the group consisting of:

2)

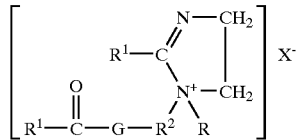

wherein each R is hydrogen or a short chain $C_1$–$C_6$ alkyl or hydroxyalkyl, benzyl, or mixtures thereof; each $R^2$ is a $C_{1-6}$ alkylene group; G is an oxygen atom or an —NR— group; the counterion, $X^-$, can be any softener-compatible anion; each $R^1$ being derived from the group consisting of:
  (i) a long chain $C_5$–$C_{21}$ alkyl;
  (ii) a long chain $C_5$–$C_2$ alkenyl; and
  (iii) a branched carboxylic acid;
with no more than one $R^1$ having less than about 11 carbons, with at least one $R^1$ comprising either a 17 or 19 carbon chain total length, wherein:

A. said 17 carbon chain total length is selected from:
   (a) 2,3-, 2,5-, 2,7-, 2,9- and 2,11-dimethylpentadecanoic acid; and mixtures thereof;
   (b) 3,4-, 3,8-, 3,10-, 3,12-, 3,14-, 4,5-, 4,7-, 4,9-, 4,11-, 4,13-, 5,6-, 5,7-, 5,8-, 5 10-, 5,11-, 5,12-, 5,13-, 5,14-, 6,7-, 6,9-, 6,11-, 6,13-, 6,14-, 7,8-, 7,9-, 7,10-, 7,11-, 7,12-, 7,13-, 7,14-, 8,9-, 8,11-, 8,13-, 8,14-, 9,10-, 9,11-, 9,12-, 9,13-, 9,14-, 10,11-, 10,13-, 11,12-, 11,13-, 11,14-, 12,13-, 12,14-, 13,14-, dimethylpentadecanoic acid; and mixtures thereof;
   (c) 3-, 4-, 5-, 6-, 7-, 8-, 9-, 10-, 11-, 12- and 13-methyl-2-ethyltetradecanoic acid; and mixtures thereof;
   (d) 3-, 5-, 6-, 7-, 8-, 9-, and 11-ethylpentadecanoic acid; and mixtures thereof;
   (e) 4-, 5-, 6-, 7-, 8-, 9-, 10- and 11-propyltetradecanoic acid; and mixtures thereof;
   (f) 3,4-, 3,5-, 3,6-, 3,7-, 3,8-, 3,9-, 3,10-, 3,11-, 3,12-, 4,5-, 4,6-, 4,7-, 4,8-, 4,9-, 4,10-, 4,11-, 4,12-, 5,6-, 5,7-, 5,8-, 5,9-, 5,10-, 5,11-, 5,12-, 6,7-, 6,8-, 6,9-, 6,10-, 6,11-, 6,12-, 7,8-, 7,9-, 7,10-, 7,11-, 7,12-, 8,9-, 8,10-, 8,11-, 8,12-, 9,10-, 9,11-, 9,12-, 10,11-, 10,12- and 11,12-dimethyl-2-ethyltridecanoic acid; and mixtures thereof;
   (g) 3-, 4-, 5-, 6-, 7-, 8-, 9-, 10-, 11- and 12-methyl-2-propyltridecanoic acid; and mixtures thereof;
   (h) 2,3,4-, 2,3,5-, 2,3,6-, 2,3,7-, 2,3,8-, 2,39-, 2,3,10-, 2,3,11-, 2,3,12-, 2,3,13-, 2,4,5-, 2,4,7-, 2,4,9-, 2,4,10-, 2,4,11-, 2,4,12-, 2,4,13-, 2,5,6-, 2,5,7-, 2,5,8-, 2,5,9-, 2,5,10-, 2,5,11-, 2,5,12-, 2,5,13-, 2,6,7-, 2,6,9-, 2,6,11-, 2,6,13-, 2,7,8-, 2,7,9-, 2,7,10-, 2,7,11-, 2,7,12-, 2,7,13-, 2,8,9-, 2,8,10-, 2,8,11-, 2,8,12-, 2,8,13-, 2,9,10-, 2,9,11-, 2,9,12-, 2,9,13-, 2,10,11-, 2,10,12-, 2,10,13-, 2,11,12-, 2,11,13-, 2,12,13-, 3,4,5-, 3,4,6-, 3,4,7-, 3,4,8-, 3,4,9-, 3,4,10-, 3,4,11-, 3,4,12-, 3,4,13-, 3,5,6-, 3,5,7-, 3,5,8-, 3,5,9-, 3,5,10-, 3,5,11-, 3,5,12-, 3,5,13-, 3,6,7-, 3,6,8-, 3,6,9-, 3,6,10-, 3,6,11-, 3,6,12-, 3,7,8-, 3,7,10-, 3,7,12-, 3,7,13-, 3,8,9-, 3,8,10-, 3,8,11-, 3,8,12-, 3,8,13-, 3,9,10-, 3,9,11-, 3,9,12-, 3,913-, 3,10,11-, 3,10,12-, 3,10,13-, 3,11,12-, 3,11,13-, 3,12,13-, 4,5,6-, 5,7-, 4,5,8-, 4,5,9-, 4,5,10-, 4,5,11-, 4,5,12-, 4,5,13-, 4,6,7-, 4,6,9-, 4,6,10-, 4,6,11-, 4,6,13-, 4,7,8-, 4,7,9-, 4,7,10-, 4,7,11-, 4,7,12-, 4,7,13-, 4,8,9-, 4,8,11-, 4,8,123-, 4,9,10-, 4,9,11-, 4,9,12-, 4,9,13-, 4,10,11-, 4,10,12-, 4,10,13-, 4,11,12-, 4,11,13-, 4,12,13-, 5,6,7-, 5,6,8-, 5,6,9-, 5,6,10-, 5,6,11-, 5,6,12-, 5,6,13-, 5,7,8-, 5,7,9-, 5,7,10-, 5,7,11-, 5,7,12-, 5,7,13-, 5,8,9-, 5,8,10-, 5,8,11-, 5,8,12-, 5,8,13-, 5,9,10-, 5,9,11-, 5,9,12-, 5,10,11-, 5,10,12-, 5,10,13-, 5,11,12-, 5,11,13-, 5,12,13-, 6,7,8-, 6,7,9-, 6,7,10-, 6,7,11-, 6,7,12-, 6,7,13-, 6,8,9-, 6,8,10-, 6,8,11-, 6,8,12-, 6,8,13-, 6,9,10-, 6,9,11-, 6,9,12-, 6,9,13-, 6,10,11-, 6,10,12-, 6,10,13-, 6,11,12-, 6,11,13-, 6,12,13-, 7,8,9-, 7,8,10-, 7,8,11-, 7,8,12-, 7,8,13-, 7,9,10-, 7,9,11-, 7,9,12-, 7,9,13-, 7,10,11-, 7,10,12-, 7,10,13-, 7,11,12-, 7,11,13-, 7,12,13-, 8,9,10-, 8,9,11-, 8,9,12-, 8,9,13-, 8,10,11-, 8,10,12-, 8,10,13-, 8,11,12-, 8,11,13-, 8,12,13-, 9,10,11-, 9,10,12-, 9,10,13-, 9,11,12-, 9,11,13-, 9,12,13-, 10,11,12-, 10,11,13-, 10,12,13- and 11,12,13-trimethyletradecanoic acid; and mixtures thereof;
   (i) 3-hexyl-4-propyloctanoic acid; 3-hexyl-4-ethylnonanoic acid; 4-pentyl-5-ethyl, 5-butyl-6-propyl, and 3-hexyl-4-methyldecanoic acid; 4-pentyl-5-methyl, 5-butyl-6-ethyl, and 6,7-dipropyl, undecanoic acid; 5-butyl-6-methyl, 7-ethyl-8-propyl, and 6-propyl-7-ethyldodecanoic acid; 7,8-ethyl, 8-methyl-9-propyl, and 6-propyl,-7-methyltridecanoic acid; 7-ethyl-8-methyl, and 8-methyl-9-ethyl, tetradecanoic acid; and mixtures thereof; and,
   (j) mixtures of (a) to (f); and B. said 19 carbon chain total length is selected from; and
   (a) 2,3-, 2,7-, 2,8-, 2,9-, 2,11-, 2,12-, 2,13-, 2,15- and 2,16-dimethylheptadecanoic acid; and mixtures thereof:
   (b) 3,4-, 3,5-, 3,6-, 3,7-, 3,8-, 3,10-, 3,12-, 3,13-, 3,14-, 3,15-, 3,16-, 4,5-, 4,7-, 4,9-, 4,11-, 4,13-, 4,15-, 4,16-, 5,6-, 5,7-, 5,8-, 5,10-, 5,11-, 5,12-, 5,13-, 5,14-, 5,15-, 5,16-, 6,7-, 6,8-, 6,9-, 6,10-, 6,11-, 6,12-, 6,13-, 6,15-, 6,16-, 7,8-, 7,9-, 7,10-, 7,11-, 7,12-, 7,13-, 7,14-, 7,15-, 7,16-, 8,9-, 8,11-, 8,12-, 8,13-, 8,15-, 8,16-, 9,10-, 9,11-, 9,12-, 9,13-, 9,14-, 9,15-, 10,16-, 10,11-, 10,12-, 10,13-, 10,15-, 10,16-, 11,12-, 11,13-, 11,14-, 11,15-, 11,16-, 12,13-, 12,14-, 12,15-, 13,14-, 13,15-, 13,16- 14,15-, 14,16-, 15,16-, dimethylheptadecanoic acid; and mixtures thereof; and
   (c) 2,3,5-, 2,3,6-, 2,3,7-, 2,3,8-, 2,3,9-, 2,3,10-, 2,3,11-, 2,3,12-, 2,3,13-, 2,3,14-, 2,3,15-, 2,4,5-, 2,4,6-, 2,4,7-, 2,4,9-, 2,4,10-, 2,4,11-, 2,4,12-, 2,4,13-, 2,4,14-, 2,4,15-, 2,5,6-, 2,5,7-, 2,5,8-, 2,5,9-, 25,10-, 2,5,11-, 2,5,12-, 2,5,13-, 2,5,14-, 2,5,15-, 2,6,7-, 2,6,9-, 2,6,11-, 2,6,12-, 2,6,13-, 2,6,14-, 2,6,15-, 2,7,8-, 2,7,9-, 2,7,10-, 2,7,11-, 2,7,12-, 2,7,13-, 2,7,14-, 2,7,15-, 2,8,9-, 2,8,11-, 2,8,12-, 2,8,13-, 2,8,14-, 2,8,15-, 2,9,10-, 2,9,11-, 2,9,12-, 2,9,13-, 2,9,14-, 2,9,15-, 2,10,11-, 2,10,13-, 2,10,14-, 2,10,15-, 2,11,12-, 2,11,13-, 2,11,14-, 2,11,15-, 2,12,13-, 2,12,14-, 2,12,15-, 2,13,14-, 2,13,15-, 2,14,15-, 3,4,5-, 3,4,6-, 3,4,7-, 3,4,8-, 3,4,9-, 3,4,10-, 3,4,11-, 3,4,12-, 3,4,13-, 3,4,14-, 3,4,15-, 3,5,6-, 3,5,7-, 3,5,8-, 3,5,9-, 3,5,10-, 3,5,11-, 3,5,12-, 3,5,13-, 2,5,14-, 3,5,15-, 3,6,7-, 3,6,8-, 3,6,9-, 3,6,10-, 3,6,11-, 3,6,12-, 3,6,13-, 3,6,14-, 3,615-, 3,7,8-, 3,7,9-, 3,7,10-, 3,7,11-, 3,7,12-, 3,7,13-, 3,7,14-, 3,7,15-, 3,8,9-, 3,8,10-, 3,8,11-, 3,8,12-, 3,8,13-, 3,8,14-, 3,8,15-, 3,9,10-, 3,9,11-, 3,9,12-, 3,9,13-, 3,9,14-, 3,9,15-, 3,10,11-, 3,10,12-, 3,10,13-, 3,10,14-, 3,10,15-, 3,11,12-, 3,11,13-, 3,11,14-, 3,11,15-, 3,12,13-, 3,13,14-, 3,12,15-, 3,13,14-, 3,13,15-, 3,14,15-, 4,5,6-, 4,5,7-, 4,5,8-, 4,5,9-, 4,5,10-, 4,5,11-, 4,5,12-, 4,5,13-, 4,5,14-, 4,5,15-, 4,6,7-, 4,6,8-, 4,6,9-, 4,6,10-, 4,6,11-, 4,6,12-, 4,6,13-, 4,6,14-, 4,6,15-, 4,7,8-, 4,7,9-, 4,7,10-, 4,7,11-, 4,7,12-, 4,7,13-, 4,7,14-, 4,7,15-, 4,8,9-, 4,8,10-, 4,8,11-, 4,8,13-, 4,8,15-, 4,9,10-, 4,9,11-, 4,9,12-, 4,9,13-, 4,9,14-, 4,9,15-, 4,10,11-, 4,10,12-, 4,10,13-, 4,10,14-, 4,10,15-, 4,11,12-, 4,11,13-, 4,11,14-, 4,11,15-, 4,12,13-, 4,12,15-, 4,13,14-, 4,13,15-, 4,14,15-, 5,6,7-, 5,6,8-, 5,6,9-, 5,6,10-, 5,6,11-, 5,6,12-, 5,6,13-, 5,6,14-, 5,6,15-, 5,7,8-, 5,7,9-, 5,7,10-, 5,7,11-, 5,7,12-, 5,7,13-, 5,7,14-, 5,7,15-, 5,8,9-, 5,8,10-, 5,8,11-, 5,8,12-, 5,8,13-, 5,8,14-, 5,8,15-, 5,9,10-, 5,9,11-, 5,9,12-, 5,9,13-, 5,9,14-, 5,9,15-, 5,10,11-, 5,10,12-, 5,10,13-, 5,10,14-, 5,10,15-, 5,11,12-, 5,11,13-, 5,11,14-, 5,11,15-, 5,12,13-, 5,12,14-, 5,12,15-, 5,13,14-, 5,13,15-, 5,14,15-, 6,7,8-, 6,7,9-, 6,7,10-, 6,7,11-, 6,7,12-, 6,7,13-, 6,7,14-, 6,7,15-, 6,8,9-, 6,8,10-, 6,8,11-, 6,8,12-, 6,8,13-, 6,8,14-, 6,8,15-, 6,9,10-, 6,9,11-, 6,9,12-, 6,9,13-, 6,9,14-, 6,9,15-, 6,10,11-, 6,10,13-, 6,10,14-, 6,10,15-, 6,11,12-, 6,11,13-, 6,11,14-, 6,11,15-, 6,12,13-, 6,12,14-, 6,12,15-, 6,13,14-, 6,13,15-, 6,14,15-, 7,8,9-, 7,8,10-, 7,8,11-, 7,8,12-, 7,8,13-, 7,8,14-, 7,8,15-, 7,9,10-, 7,9,11-, 7,9,12-, 7,9,13-, 7,9,14-, 7,9,15-, 7,10,11-, 7,10,12-, 7,10,13-, 7,10,14-, 7,10,15-, 7,11,12-, 7,11,13-, 7,11,14-, 7,11,15-, 7,12,13-, 7,12,14-, 7,12,15-, 7,13,14-, 7,13,15-, 7,14,15-, 8,9,10-, 8,9,13-, 8,9,12-, 8,9,13-, 8,9,14-, 8,9,15-, 8,10,11-, 8,10,13-, 8,10,14-, 8,10,15-, 8,11,12-, 8,11,13-, 8,11,14-, 8,11,15-, 8,12,13-, 8,12,14-, 8,12,15-, 8,13,14-, 8,13,15-, 9,14,15-, 8,14,15-, 9,10,11-, 9,10,12-, 9,10,13-, 9,10,14-, 9,10,15-, 9,11,12-, 9,11,13-, 9,11,14-, 9,11,15-, 9,12,13-, 9,12,14-, 9,12,15-, 9,13,14-, 9,13,15-, 9,14,15-, 10,11,12-, 10,31,13-, 10,11,14-, 10,11,15-, 10,12,13-, 10,12,14-, 10,12,15-, 10,13,14-, 10,13,15-, 10,14,15-, 11,12,13-, 11,12,14-, 11,12,15-, 11,13,14-, 11,13,15-, 11,14,15-, 12,13,14-, 12,13,15-, 12,14,15- and 13,14,15-trimethylhexadecanoic acid; and mixtures thereof:

(d) mixtures of (a) to (c).

2. The fabric softening active of claim 1 wherein $R^1$ comprises an unsaturated alkyl group having an Iodine Value of from about 20 about 140.

3. The fabric softening active of claim 2 wherein said unsaturated alkyl group is derived from a fatty acid with the same Iodine Value.

4. The fabric softening active of claim 1 having a phase transition temperature of less than about 50° C.

5. The fabric softening active of claim 4 having a phase transition ,temperature of less than about 35° C.

6. The fabric softening active of claim 5 having a phase transition temperature of less than about 20° C.

7. A fabric softening composition comprising:
A) from about 2% to about 80%, by weight of the composition, of said fabric softener active according to claim 1;
B) optionally, an effective amount to improve clarity, but less than bout 40%, by weight of the composition of principal solvent having a ClogP of from about 2.0 to about 2.6;
C) optionally, an effective amount, sufficient to improve clarity, of low molecular weight water soluble solvent selected from the group consisting of ethanol, isopropanol, propylene glycol, 1,3-propanediol, propylene carbonate, and mixture thereof, said water soluble solvents being at a level that will not form clear compositions by themselves;
D) optionally, an effective amount to improve clarity, of water soluble calcium and/or magnesium salt; and
E) optionally, the balance being water.

8. The fabric softening composition according to claim 7, wherein the principle solvent has a ClogP of from about −1.0 to about 1.0.

9. The fabric softening composition according to claim 8, wherein the principle solvent has a ClogP of from about 0.15 to about 0.64.

* * * * *